US011510901B2

(12) United States Patent
Oronsky et al.

(10) Patent No.: US 11,510,901 B2
(45) Date of Patent: Nov. 29, 2022

(54) METHODS AND COMPOSITIONS UTILIZING RRX-001 COMBINATION THERAPY FOR RADIOPROTECTION

(71) Applicant: EpicentRx, Inc., La Jolla, CA (US)

(72) Inventors: Bryan T. Oronsky, La Jolla, CA (US); Arnold Oronsky, La Jolla, CA (US); Tony R. Reid, La Jolla, CA (US)

(73) Assignee: EpicentRx, Inc., La Jolla, CA (US)

(*) Notice: Subject to any disclaimer, the term of this patent is extended or adjusted under 35 U.S.C. 154(b) by 133 days.

(21) Appl. No.: 16/960,444

(22) PCT Filed: Jan. 8, 2019

(86) PCT No.: PCT/US2019/012696
§ 371 (c)(1),
(2) Date: Jul. 7, 2020

(87) PCT Pub. No.: WO2019/164593
PCT Pub. Date: Aug. 29, 2019

(65) Prior Publication Data
US 2020/0345690 A1 Nov. 5, 2020

Related U.S. Application Data

(60) Provisional application No. 62/737,096, filed on Sep. 26, 2018, provisional application No. 62/614,595, filed on Jan. 8, 2018.

(51) Int. Cl.
*A61K 31/66* (2006.01)
*A61K 31/397* (2006.01)
*A61K 31/19* (2006.01)
*A61K 33/24* (2019.01)
*A61K 33/26* (2006.01)
*A61K 9/00* (2006.01)
*A61K 45/06* (2006.01)

(52) U.S. Cl.
CPC .......... *A61K 31/397* (2013.01); *A61K 9/0014* (2013.01); *A61K 9/0019* (2013.01); *A61K 9/0053* (2013.01); *A61K 45/06* (2013.01)

(58) Field of Classification Search
CPC ...... A61K 31/66; A61K 31/397; A61K 31/19; A61K 33/24; A61K 33/26
USPC ............. 514/210.17, 114, 562; 424/646, 647
See application file for complete search history.

(56) References Cited

U.S. PATENT DOCUMENTS

| | | |
|---|---|---|
| 2,978,453 A | 4/1961 | Milton |
| 3,845,770 A | 11/1974 | Theeuwes et al. |
| 3,916,899 A | 11/1975 | Theeuwes et al. |
| 4,584,130 A | 4/1986 | Bucci et al. |
| 4,765,539 A | 8/1988 | Noakes et al. |
| 5,112,598 A | 5/1992 | Biesalski |
| 5,336,784 A | 8/1994 | Hiskey et al. |
| 5,521,203 A | 5/1996 | Adams et al. |
| 5,556,611 A | 9/1996 | Biesalski |
| 5,579,458 A | 11/1996 | Yokosuka et al. |
| 5,580,988 A | 12/1996 | Dave |
| 5,607,830 A | 3/1997 | Biesel et al. |
| 5,679,777 A | 10/1997 | Anderson et al. |
| 5,693,794 A | 12/1997 | Nielsen |
| 5,698,155 A | 12/1997 | Grosswald et al. |
| 5,950,619 A | 9/1999 | van der Linden et al. |
| 5,954,047 A | 9/1999 | Armer et al. |
| 5,970,974 A | 10/1999 | Van Der Linden et al. |
| 6,133,320 A | 10/2000 | Yallampalli et al. |
| 6,245,799 B1 | 6/2001 | Asselin et al. |
| 6,391,911 B1 | 5/2002 | Bases |
| 6,407,236 B1 | 6/2002 | Baraldi et al. |
| 7,163,958 B2 | 1/2007 | Earl et al. |
| 7,507,842 B2 | 3/2009 | Knox et al. |
| 7,745,643 B2 | 6/2010 | Cannizzo et al. |
| 8,178,698 B2 | 5/2012 | Cannizzo et al. |
| 8,299,053 B2 | 10/2012 | Bednarski et al. |
| 8,664,247 B2 | 3/2014 | Scicinski et al. |
| 8,927,527 B2 | 1/2015 | Bednarski et al. |
| 9,139,519 B2 | 9/2015 | Scicinski et al. |
| 9,226,915 B2 | 1/2016 | Bednarski et al. |
| 9,468,625 B2 | 10/2016 | Scicinski et al. |
| 9,987,270 B1 | 6/2018 | Oronsky et al. |

(Continued)

FOREIGN PATENT DOCUMENTS

| | | |
|---|---|---|
| DE | 10111049 A1 | 9/2002 |
| EP | 412211 A1 | 2/1991 |

(Continued)

OTHER PUBLICATIONS

ClinicalTrials.gov, "Safety and Efficacy of RRx-001 in the Attenuation of Oral Mucositis in Patients Receiving Chemoradiation for the Treatment of Oral Cancers (PREVLAR)," May 3, 2018, 12 pages, retrieved from the internet URL:https://clinicaltrials.gov/ct2/show/NCT03515538 on Aug. 27, 2018.
International Preliminary Report on Patentability dated Jul. 23, 2020 in PCT/US2019/012696.
International Search Report and Written Opinion dated Sep. 6, 2019 in PCT/US2019/012696.
Kamran et al., "Radioprotective Agents: Strategies and Translational Advances," Medicinal Research Reviews, 2016, 36(3):461-493.
Kim et al., "Whole Brain Radiotherapy and RRx-001: Two Partial Responses in Radioresistant Melanoma Brain Metastases from a Phase I/II Clinical Trial: A TITE-CRM Phase I/II Clinical Trial," Translational Oncology, Apr. 2016, 9(2):108-113.

(Continued)

Primary Examiner — Raymond J Henley, III
(74) Attorney, Agent, or Firm — Morrison & Foerster LLP

(57) ABSTRACT

Provided herein are therapeutic methods, kits, and pharmaceutical compositions for protecting a subject from radiation using a therapeutic agent selected from the group consisting of RRx-OO1 and a pharmaceutically acceptable salt thereof. One exemplary therapeutic method involves administering RRx-OO1 to the subject prior to the subject being exposed to the radiation, in order to protect the subject against radiation, such as ionizing radiation containing α-rays, β-rays, γ-rays, neutron radiation, or a combination thereof.

20 Claims, 31 Drawing Sheets

(56) References Cited

U.S. PATENT DOCUMENTS

| | | |
|---|---|---|
| 10,149,832 B2 | 12/2018 | Bednarski et al. |
| 10,342,778 B1 | 7/2019 | Oronsky et al. |
| 10,543,208 B2 | 1/2020 | Oronsky et al. |
| 11,008,287 B2 | 5/2021 | Oronsky et al. |
| 11,160,784 B1 | 11/2021 | Oronsky et al. |
| 2002/0137770 A1 | 9/2002 | Nara et al. |
| 2003/0092684 A1 | 5/2003 | Fredekinq et al. |
| 2004/0024057 A1 | 2/2004 | Earl et al. |
| 2004/0167212 A1 | 8/2004 | Bednarski et al. |
| 2005/0070872 A1 | 3/2005 | Sato et al. |
| 2006/0111272 A1 | 5/2006 | Roberts et al. |
| 2006/0211639 A1 | 9/2006 | Bratzler et al. |
| 2007/0135384 A1 | 6/2007 | Bednarski et al. |
| 2008/0255149 A1 | 10/2008 | Dobler et al. |
| 2008/0256149 A1 | 10/2008 | Bansal et al. |
| 2009/0093644 A1 | 4/2009 | Cannizzo et al. |
| 2009/0163466 A1 | 6/2009 | Bednarski et al. |
| 2009/0192085 A1 | 7/2009 | Robson et al. |
| 2010/0247682 A1 | 9/2010 | Gladwin et al. |
| 2010/0260719 A1 | 10/2010 | Zeldis |
| 2011/0130572 A1 | 6/2011 | Cannizzo et al. |
| 2011/0195947 A1 | 8/2011 | Straessler et al. |
| 2012/0149678 A1 | 6/2012 | Oronsky et al. |
| 2013/0053418 A1 | 2/2013 | Scicinski et al. |
| 2013/0123216 A1 | 5/2013 | Bednarski et al. |
| 2014/0220163 A1 | 8/2014 | Babadi et al. |
| 2014/0308260 A1 | 10/2014 | Oronsky et al. |
| 2014/0349988 A1 | 11/2014 | Scicinski et al. |
| 2015/0190465 A1 | 7/2015 | Faivre et al. |
| 2015/0246020 A1 | 9/2015 | Bednarski et al. |
| 2016/0081981 A1 | 3/2016 | Scicinski et al. |
| 2016/0199346 A1 | 7/2016 | Bednarski et al. |
| 2018/0085346 A1 | 3/2018 | Bednarski et al. |
| 2019/0125742 A1 | 5/2019 | Oronsky et al. |
| 2019/0307723 A1 | 10/2019 | Oronsky et al. |
| 2020/0022952 A1 | 1/2020 | Oronsky et al. |
| 2020/0046682 A1 | 2/2020 | Bednarski et al. |
| 2020/0157047 A1 | 5/2020 | Oronsky et al. |
| 2020/0254016 A1 | 8/2020 | Oronsky |
| 2020/0345689 A1 | 11/2020 | Oronsky et al. |
| 2020/0375982 A1 | 12/2020 | Oronsky et al. |
| 2022/0016077 A1 | 1/2022 | Bednarski et al. |
| 2022/0054480 A1 | 2/2022 | Oronsky et al. |

FOREIGN PATENT DOCUMENTS

| | | |
|---|---|---|
| JP | S48030376 B | 9/1973 |
| JP | S5511509 A | 1/1980 |
| JP | H05155847 A | 6/1993 |
| JP | 2001506974 A | 5/2011 |
| JP | 2014530811 A | 11/2014 |
| WO | WO-1995032715 A1 | 12/1995 |
| WO | WO-1996036602 A1 | 11/1996 |
| WO | WO-1998016485 A1 | 4/1998 |
| WO | WO-1998016502 A1 | 4/1998 |
| WO | WO-1999016436 A1 | 4/1999 |
| WO | WO-1999059575 A1 | 11/1999 |
| WO | WO-2000006143 A1 | 2/2000 |
| WO | WO-2001077100 A2 | 10/2001 |
| WO | WO-2004032864 A2 | 4/2004 |
| WO | WO-2004098538 A2 | 11/2004 |
| WO | WO-2004113281 A1 | 12/2004 |
| WO | WO-2005046661 A2 | 5/2005 |
| WO | WO-2006102760 A1 | 10/2006 |
| WO | WO-2007/022225 A2 | 2/2007 |
| WO | WO-2007022121 A2 | 2/2007 |
| WO | WO-2012078992 A1 | 6/2012 |
| WO | WO-2013052164 A1 | 4/2013 |
| WO | WO-2013052803 A2 | 4/2013 |
| WO | WO-2017123593 A1 | 7/2017 |

OTHER PUBLICATIONS

Ning et al., "Dinitroazetidines Are a Novel Class of Anticancer Agents and Hypoxia-Activated Radiation Sensitizers Developed from Highly Energetic Materials," Cancer Research, May 15, 2012, 72(10):2600-2608.

Oronsky et al., "RRx-001, A novel dinitroazetidine radiosensitizer," Invest. New Drugs, Feb. 3, 2016, 34(3):371-377.

Oronsky et al., "RRx-001: a systemically non-toxic M2-to-M1 macrophage stimulating and prosensitizing agent in Phase II clinical trials," Expert Opinion on Investigational Drugs, Dec. 21, 2016, 26(1):109-119.

Scicinski et al., "NO to cancer: The complex and multifaceted role of nitric oxide and the epigenetic nitric oxide donor, RRx-001," Redox Biology, Dec. 1, 2015, 6:1-8.

Akhavan (2004). "Explosives and Propellants," Kirk-Othmer Encyclopedia of Chemical Technology, pp. 719-744.

Aiderman, (1984). "A Review of Cellulose Ethers in Hydrophilic Matrices for Oral Controlled-Release Dosage Forms," Int. J. Pharm. Tech. & Prod. Mfr., 5(3):1-9.

Archibald et al., (1990). "Synthesis and x-ray crystal structure of 1,3,3-trinitroazetidine," J. Org. Chem., 55:2920-2924.

Armstrong et al., (2002). "Role of Glutathione Depletion and Reactive Oxygen Species Generation in Apoptotic Signaling in a Human B Lymphoma Cell Line, Cell Death and Differentiation," Nature, 9:252-263, 2002.

Australian Examination Report received for Australian patent application No. 2006279589, dated May 18, 2012, 3 pages.

Bamba et al., (1979). "Release Mechanisms in Gelforming Sustained Release Preparations," Int. J. Pharm., 2:307-315.

Berge et al., (1997). "Pharmaceutical Salts," Journal of Pharmaceutical Sciences, 66(1):1-19.

Brown et al., (1998). "Tirapazamine: Laboratory Data Relevant to Clinical Activity," AntiCancer Drug Design, 13:529-539. Abstract Only.

Cabrales et al., (2016). "A look inside the mechanistic black box: Are red blood cells the critical effectors of RRx-001 cytotoxicity?" Medical Oncology, 33(7):63, 7 Pages. Abstract Only.

Carter et al., (2016). "Partial response to carboplatin in an RRx-001 pretreated patient with EGFR-inhibitor-resistance and T790M-negative NSCLC," Respir. Aged Case Rep., 18:62-65.

Chawla et al., (2004). "Challenges in Polymorphism of Pharmaceuticals," CRIPS, 5(1):12-15.

ClinicalTrials.gov, (2015). "NCT02489903: An Open-label, Three Stage, Three Arm Pilot Study of RRx-001 For Second Line or Greater Small Cell Lung Cancer, Third Line or Greater Non-Small Lung Cancer, and Second Line or Greater High Grade Neuroendocrine Tumors Prior to Re-administration of Platinum Based Doublet Regimens (Triple Threat)", Available from the Internet, <https://clinicaltrials.gov/ct2/history/NCT02489903?V_1 =View#StudyPageTop>, 12 pages.

ClinicalTrials.gov, (2019). "NCT02489903: RRX-001 in Lung Cancer, Ovarian Cancer and Neuroendocrine Tumors Prior to Re-administration of Platinum Based Doublet Regimens (Quadruple Threat)", available online at <https://clinicaltrials.gov/ct2/history/NCT02489903?V_1 =View#StudyPageTop>, 10 pages.

ClinicalTrials.gov, (2020). "NCT02871843: Phase 1 Two Part Dose Escalation Trial of RRx-001 + Radiation + Temozolomide and RRx-001 + Temozolomide Post-RT In Newly Diagnosed Glioblastoma and Anaplastic Gliomas (G-FORCE-1)," available online at < https://clinicaltrials.gov/ct2/show/NCT02871843>, 8 pages.

Clinicaltrials.gov, (2021). "NCT02215512: Dose-Escalation Study of RRx-001 in Combination With Whole Brain Radiation in Subjects With Brain Metastases (Brainstorm)," available online at < https://clinicaltrials.gov/ct2/show/NCT02215512>,.

Coburn et al., (1998). caplus an 1998:567551, RN 179894-08-7, 1 page.

Crowder et al., (1999). "Vibrational analysis of high-energy compounds: 1,3,3-trinitroazetidine and 1-acetvl-3, 3-dinitroazetidine," Journal of Energetic Materials, 17(1):49-68.

Crowder et al., (1999). caplus an 1999:171384, RN 179894-08-7,1 page.

(56) References Cited

OTHER PUBLICATIONS

Dave et al., (2000). "Convenient Acylative Dealkylation of Tertiary Amines," Journal of Organic Chemistry, 65:1207-1209.
Dave, (1996). "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., 61:5453-5455.
Dave, (1997), caplus an 1997:67373, RN 179894-08-7,1 page.
Dorman, (2000). "Fulminant babesiosis treated with clindamycin, quinine, and wholeblood exchange transfusion," Transfusion, 40(3):375-80.
Drumond et al., (2013). "Transmissible Venereal Tumor treated with Autohemotherapy," Acta Scientiae Veterinariae, 41:1107, 4 pages.
During et al., (1989). "Controlled Release of Dopamine from a Polymeric Brain Implant: In Vivo Characterization," Annals of Neurology, 25(4):351-356. Abstract Only.
Fareed et al., (2000). "An update on herapins at the beginning of the new millennium," Semin Thromb Hemost., 26(Suppl 1):5-21.
Feuer et al., (1954). "The Mannich reaction of certain dinitro alcohols with glycine and ethanolamine," Journal of American Chemical Society, 76:5124-5126.
Fitch et al., (2013). "Abstract WRM 267: High resolution MS proves that the developmental cancer drug, RRx-001, alkylates the hemoglobin beta chain," 44th Western Regional Meeting of the American Chemical Society, available online at <http://www.acswrm.org/wrm2013/files/Abstracts_SaturdayAM.pdf>, 1 page.
Garver et al., (1984). "Catalyzed Oxidative Nitration of Nitronate Salts," J. Org. Chem. 50(10):1699-1702.
Gladwin et al., (2005). "The Emerging Biology of the Nitrite Anion," in Nature Chemistry and Biology, 1:308-31.
Goodson, (1984). "Dental Applications," Chapter 6 of Medical Applications of Controlled Release, 2:115-138.
Granelli et al., (2004). "SEL 1 Land Squamous Cell Carcinoma of the Esophagus," Clinical Cancer Research, 10:5857-5861.
Heller, (2010). "An Electrochemical Engineering Perspective of Nitric Oxide in Tumors Why the Combination of an Allosteric Effector of Hemoglobin with Dietary Sodium Nitrite Should Be Effective in Treating Vascularized Tumors?," ECS Transactions, 28(33):1-6.
Hiskey et al., "Preparation of 1-Substituted-3,3-Dinitroazetidines," Journal of Energetic Materials, 1999, vol. 17, pp. 233-254.
Hiskey et al., (1993). caplus an 1993:233785, RN 147636-85-9, 1 page.
Hiskey et al., (1994). caplus an 1994:700750, RN 158669-97-7, 1 page.
Hiskey et al., (1999). caplus an 1999:411860, RN 236102-58-2, 1 page.
Hockel et al., "Tumor Hypoxia: Definitions and Current Clinical, Biologic, and Molecular Aspects," Journal of the National Cancer Institute, 2001, vol. 93, No. 4, pp. 266-276.
Howard et al., "Intracerebral Drug Delivery in Rats with Lesion-Induced Memory Deficits," J. Neurosura., 1989, vol. 71, pp. 105-112.
Huguenin, Sandra, et al., "Evaluation of the antitumoral potential of different nitric oxide-donating non-steroidal anti-inflammatory drugs (NO-NSAIDs) on human urological tumor cell lines," Cancer Letters (2005) vol. 218, DD. 163-170.
Ignarro, Louis J., Nitric Oxide Biology and Pathology, 2000, pp. 5, 895, and 908, Academic Press.
International Preliminary Report on Patentability dated Jul. 14, 2020 in PCT/US2019/012701, 8 pages.
International Search Report and Written Opinion dated Sep. 4, 2019 in PCT/US2019/012701, 12 pages.
International Search Report and Written Opinion for PCT/US2011/064178 dated Apr. 17, 2012. (8 pages).
International Search Report and Written Opinion for PCT/US2012/038592 dated Aug. 10, 2012. (11 pages).
International Search Report and Written Opinion for PCT/US2012/058964, dated Apr. 5, 2013, 9 pages.
International Search Report and Written Opinion for PCT/US2017/012948 dated Mar. 28, 2017, 8 pages.
International Search Report and Written Opinion for PCT/US2017/056454 dated Feb. 6, 2018, 12 pages.
International Search Report and Written Opinion for PCT/US2018/041138 dated Oct. 5, 2018, 9 pages.
International Search Report for PCT/US2006/031722 dated May 29, 2007, 1 page.
International Search Report for PCT/US2006/031917 dated Jul. 20, 2007, 1 page.
International Search Report for PCT/US2011/021500 dated May 3, 2011, 4 pages.
Jia, (2008). "A Guide to Pass the National Licensed Pharmacist Examination in Medicinal Chemistry," pp. 4-11, 9 pages.
Jia, Q., et al., "NO donors with anticancer activity," Expert Opin. Therapeut. Patents (2002) vol. 12, No. 6, DD. 819-826.
Johnson, J. et al., "Relationships Between Drug Activity in NCI Preclinical in Vitro and in Vivo Models and Early Clinical Trials," British J. Cancer (2001) vol. 8 4, No. 10, pp. 1424-1431.
Kashfi, Khosrow, et al., "Nitric Oxide-Donating Nonsteroidal Anti-Inflammatory Drugs Inhibit the Growth of Various Cultured Human Cancel Cells: Evidence of a Tissue Type-Independent Effect," J. Pharmacology Experimental Therapeutics (2002) vol. 303, No. 3, pp. 1273-1282.
Katritzky et al., "Novel Syntheses of 1,3,3-Trinitroazetidine," J. Heterocyclic Chem., Mar.-Apr. 1994, vol. 31, pp. 271-275.
Konovalova, N.P., et al., "Nitric oxide donor increases the efficiency of cytostatic therapy and retards the development of drug resistance," Nitric Oxide (2003) vol. 8, No. 1, pp. 59-64.
Kornblum et al., "Oxidative Substitution of Nitroparaffin Salts," J. Org. Chem., 1983, vol. 48, pp. 332-337.
Langer et al., "Chemical and Physical Structure of Polymers as Carriers for Controlled Release of Bioactive Agents: A Review," JMS-Rev. Macromol. Chem. Phvs., 1983, Ch. 23, pp. 61-126.
Langer et al., eds., "Medical Applications of Controlled Release," vol. 1, Classes of Systems, Ch. 2, pp. 42-67, CRC Press, Inc., Boca Raton, FL, copyright 1984.
Langer, R., "New Methods of Drug Delivery," Science (1990) vol. 249, No. 4976, pp. 1527-1533.
Levy, R., et al. "Inhibition of Calcification of Bioprosthetic Heart Valves by Local Controlled—Release Diphosphonate," Science (1985) vol. 228, No. 4696, pp. 190-192.
Li et al., (2006). caplus an 2006:150006, RN 179894-08-7, 1 page.
Li, (2014). "Nursing Comprehensive Skills Training," China Press of Traditional Chinese Medicine, 3 pages.
Ling et al., "Phase I study of CM-Na combined with concurrent radiochemotherapy for advanced esophageal carcinoma," Chinese Journal of Cancer, 2005, vol. 24, No. 5, (abstract).
Lopez-Ferrer et al., "Differences in the O-Glycosylation Patterns Between Lung Squamous Cell Carcinoma and Adenocarcinoma," Am. J. Clin. Pathol., 2002, vol. 118, pp. 749-755.
Lusk et al., (2004). "Electrochemical Oxidation of Alkylnitro Compounds PP-1345, A SERDP 'SEED' Activity," available online at <https://www.serdp-estcp.org/content/download/6439/85721/file/PP-1345-FR-01.pdf>, 30 pages.
Marchand et al., "A Novel Approach to the Synthesis of 1,3,3-Trinitroazetidine," J. Org Chem. 1995, vol. 60, No. 15, pp. 4943-4946.
Marchand et al., "Additions of X-Y Across the C(3)—N a-Bond in 1-Aza-3-ethylbicyclo[1.1.0]butane, Novel Routes to 3-Substituted Azetidines," Journal of Organic Chemistry, 1994, vol. 59, No. 18, pp. 5499-5501.
Maxwell et al., "Hypoxia-inducible factor-1 modulates gene expression in solid tumors and influences both angiogenesis and tumor growth," Proc. Natl. Acad. Sci. USA, 1997, vol. 94, pp. 8104-8109.
McKenney et al., "Synthesis and thermal properties of 1,3-dinitro-3-(1', 3'-dinitroazetidin-3'-yl) azetidine (TNDAZ) and its admixtures with 1,3,3-trinitroazetidine (TNAZ)," Journal of Energetic Materials, 1998, vol. 16, pp. 199-235.
Mendenhall, William M., et al., "Radiation Therapy for Squamous Cell Carcinoma of the Tonsillar Region: A Preferred Alternative to Surgery?" J. Clinical Oncology (2000) vol. 18, No. 11, pp. 2219-2225.

(56) References Cited

OTHER PUBLICATIONS

Miller et al., (2015). "CD47 Receptor Globally Regulates Metabolic Pathways That Control Resistance to Ionizing Radiation," J. Biol. Chem., 290:24858-24874.
Morales-Suarez-Varela, Maria M., et al., "Impact of Nitrates in Drinking Water on Cancer Mortality in Valencia, Spain," European Journal of Epidemiology, 1995, DD. 15-21, vol. 11.
Muehlstaedt et al., (1975). caplus an 1976:89768, RN 58373-43-6, 1 page.
Nabi et al., (2001). "Primary squamous cell carcinoma of the prostate: a rare clinicopathological entity. Report of 2 cases and review of literature," Ural. Int., 66(4):216-219. Abstract Only.
Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem. (2003) vol. 46, DD. 995-1004.
Nara et al., (2002). caplus an 2002:169585, RN 402835-09-0, 1 page.
Newman, Ann W. and Byrn, Stephen R. "Solid-state analysis of the active pharmaceutical ingredient in drug products," Drug Discovery Today (2003) vol. 8, No. 19, pp. 898-905.
Nih, Vascular Tumor, 2018, <https://www.cancer.gov/gublications/dictionaries/cancer-terms/def/vascular-tumor>.
Ning et al., (2015). "Nrf2 activity as a potential biomarker for the pan-epigenetic anticancer agent, RRx-001," Oncotarget, 6(25):21547-21556.
Ning, Shoucheng, et al., The Antiangiogenic Agents SU5416 and SU6668 Increase the Antitumor Effects of Fractionated Irradiation, Radiation Research, 2002, pp. 45-51, vol. 157.
Nitrates and Nitrites Answers to Frequently Asked Questions, Ohio Bureau of Environmental Health, Health Assessment Section, Nov. 1, 2006. (2 pages).
Oberoi et al., "Nanocarriers for delivery of platinum anticancer drugs," Advanced Drug Delivery Reviews, vol. 65, No. 13, Oct. 8, 2013, pp. 1667-1685, XP028782543.
Oronsky, B. T. et al., "A Review of Two Promising Radiosensitizers in Brain Metastases Rrx-001 and 2-Deoxyqlucose," J. Cancer Sci. Ther. (2015) vol. 7, DD. 137-141.
Oxley J. et al., "Thermal Decomposition Pathways of 1,3,3-Trinitroazetidine (TNAZ), Related 3,3- Dinitroazetidium Salts, and 15N, 13C, and 2H Isotopomers," Journal of Physical Chemistry A, 1997, vol. 101, No. 24, DD. 4375-4383.
Padwa et al., "Diastereofacial selectivity in azomethine ylide cycloaddition reactions derived from chiral alpha-cyanoaminosilanes," Tetrahedron (1985) vol. 41, No. 17, DD. 3529-3535.
Peiris, S. M. et al., "Structures of dinitroazetidine and three of its carbonyl derivatives," Journal of Chemical Crystalographv, 2001, vol. 30, No. 10, DD. 647-653.
Prezioso, J.A., et al., Genetic Toxicity Evaluation of 1,3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wriqht-Patterson Air Force Base, Ohio.
Rafikova et al., (2004). "Control of Plasma Nitric Oxide Bioactivity by Perfluorocarbons Physiological Mechanisms and Clinical Implications," Circulation., 110:3573-3580.
Raleigh et al. "Pharmacokinetics of Isotretinoin (ISO) in Rats Following Oral Dosing or Aerosol Inhalation," British J. Cancer, 1999, vol. 80, SuDDI. 2, 96, P269.
Reid et al., (2014). "Two Case Reports of Resensitization to Previous Chemotherapy with the Novel Hypoxia-Activated Hypomethylating Anticancer Agent RRx-001 in Metastatic Colorectal Cancer Patients," Case Rep. Oncol., 7(1):79-85.
Remington, "The Science and Practice of Pharmacy," 19th Edition, vol. II, pp. 1495-1562, 1577-1614, and 1660-1692; Mack Publishing Company, Easton, PA, 1995.
Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research (1999) vol. 5, No. 4, DD. 739-745.
Rupnow, Brent A, et al., p53 Mediates Apoptosis Induced by C-Myc Activation in Hypoxic or Gamma Irradiated Fibroblasts, Cell Death and Differentiation, 1998, pp. 141-147, vol. 7.
Sandler, G., "Clinical evaluation of propatylnitrate in angina pectoris," British Medical Journal, vol. 2, No. 5269 (Dec. 30, 1961), DD. 1741-1744.
Sauder, C. "A Preliminary Trial of the Programmable Implantable Medication System for Insulin Delivery," The New England Journal of Medicine, 1989, vol. 321, No. 9, pp. 574-579.
Sausville, Edward A., et al., "Contributions of Human Tumor Xenografts to Anticancer Development," Cancer Research (2006) vol. 66, No. 7, DD. 3351-3354.
Schwartz (2007). "Anemia in patients with cancer: incidence, causes, impact, management, and use of treatment guidelines and protocols," Am. J. Health-Syst. Pharm., 64(3 Supplement 2):S5-S13.
Scicinski et al., "Preclinical Evaluation of the Metabolism and Disposition of RRx-001, a Novel Investigative Anticancer Agent", Drug Metabolism and Disposition (2012), vol. 40, No. 9, pp. 1810-1816.
Scicinski et al., "Development of methods for the bioanalysis of RRx-001 and metabolites", Bioanalysis (2014), 6(7):947-956.
Sefton, M., "Implantable Pumps," CRC Grit. Rev. Biomed. Eng., 1987, vol. 14, No. 3, pp. 201-237.
Shokeir, A., "Squamous Cell Carcinoma of the Bladder: pathology, diagnosis and treatment," BJU International, 2004, vol. 93, pp. 216-220.
Sikder et al., "1,3,3-Trinitroazetidine (TNAZ), a melt-cast explosive: synthesis, characterization and thermal behavior," Journal of Hazardous Materials, vol. 113, 2004, DD. 35-43.
Simpson, R.L., et al., "Characterization of TNAZ," UCRL-ID-119672, Dec. 14, 1994, Lawrence Livermore National Laboratory, 15 pages.
Smolen, Victor F., et al., eds., "Controlled Drug Bioavailability," vol. 1, Drug Product Design and Performance, Ch. 7, DD. 203-237, John Wiley & Sons, New York, NY, copyright 1984.
Stamler, J.S., et al., "Inhaled ethyl nitrite gas for persistent pulmonary hypertension in infants," The Lancet (2002) vol. 360, No. 9350, p. 2077.
Straessler et al., "Development of a Safe and Efficient Two-Step Synthesis for Preparing 1- Bromoacetyl-3,3-dinitroazetidine, a Novel Clinical Anticancer Candidate," Organic Process Research & Development, 2012, vol. 16, pp. 512-517.
Stratford et al., "Bioreductive drugs into the next millennium," Anti-Cancer Drug Design, 1998, vol. 13, pp. 519-528.
Merck & Co., Inc., (2008). "TEMODAR Prescribing Information," 17 pages.
Treat, Joseph, et al., "Liposome Encapsulated Doxorubicin: Preliminary Results of Phase I and Phase II Trials," pp. 353-365 of "Liposomes in the Therapy of Infectious Diseases and Cancer, Proceedings of the Ciba-Geigy-Squibb-UCLA Colloquium at Lake Tahoe, CA, Feb. 16-20, 1988," Lopez-Berestein, G. and Fidler, I. J. (eds.), Alan R. Liss, Inc., New York, 1989.
Verma et al., "Osmotically Controlled Oral Drug Delivery," Drug Dev. Ind. Pharm., 2000, vol. 26, No. 7, pp. 695-708.
Watt, Duncan S. and Cliff, Matthew D. "Evaluation of 1,3,3-Trinitrozaetidine (TNAZ)—A High Performance Melt-Castable Explosive," Weapons Systems Division, Aeronautical and Maritime Research Laboratory, Melbourne, Australia. Report No. DSTO-TR-1000, Issue date Jul. 2000. (34 pages).
Watt, Duncan S. and Cliff, Matthew D. "TNAZ Based Melt-Cast Explosives: Technology Review and AMRL Research Directions," Weapons Systems Division, Aeronautical and Maritime Research Laboratory, Melbourne, Australia. Report DSTO-TR-0702, Issue date Jul. 1998. (37 pages).
West, Anthony R., Solid State Chemistry and its Applications, 1988, pp. 358, and 365, Wiley, New York.
Weyerbrock et al., (2003). "Selective opening of the blood—brain barrier by a nitric oxide donor and long-term survival in rats with C6 gliomas," Journal of Neurosurgery, 99(4):728-737.
Wilson, et al., "Radiation-activated prodrugs as hypoxia-selective cytotoxins: model studies with nitroarylmethyl quaternary salts," Anti-Cancer Drug Design, 1998, vol. 13, pp. 663-685.

(56) References Cited

OTHER PUBLICATIONS

Wong, (1991). "Chapter 5: Heterobifunctional Cross-Linkers," Chemistry of Protein Conjugation and Crosslinking, p. 147, 3 pages.
Written Opinion of the International Searching Authority for PCT/US2006/031722 dated May 29, 2007, 3 pages.
Written Opinion of the International Searching Authority for PCT/US2006/031917 dated Jul. 20, 2007, 3 pages.
Written Opinion of the International Searching Authority for PCT/US2011/021500 dated Aug. 9, 2012, 4 pages.
Wu et al., (2011). "Reactive impurities in excipients: profiling, identification and mitigation of drug-excipient incompatibility," in AAPS PharmSciTech., 12(4):1248-1263.
Yamaguchi, A., et al., "Photodynamic Therapy with Motexafin Lutetium (Lu-Tex) Reduces Experimental Graft Coronary Artery Disease," Transplantation, Jun. 15, 2001, pp. 1526-1532, vol. 71, No. 11, 11 pages.
Yarmukhamedov et al., "One-step synthesis of substituted 3,5-dinitropiperidines and 1,5-dinitro-3,7-diazabicyclo(3.3.1)nonanes from 1,3-dinitropropanes," Russian Chemical Bulletin, International Edition, 2005, vol. 54, No. 2, DD. 414-420.
Yen et al., "18F-FDG Uptake in Squamous Cell Carcinoma of the Cervix is Correlated with Glucose Transporter 1 Expression," The Journal of Nuclear Medicine, 2004, vol. 45, No. 1, pp. 22-29.
You, (2011). ""代动力学性质，不但增加7，血药浓度。，且延长作用时间,"," Medicinal Chemistry, pp. 585-588, 5 p.
Zhang et al., (1998). caplus an 1998:460439, RN 211429-18-4, 1 page.
Zhu et al., "Amino-functionalized nano-vesicles for enhanced anticancer efficacy and Yeduced myelotoxicity of carboplatin," Colloids and Surfaces, B, Biointerfaces, Elsevier, Amsterdam, NL, vol. 157, May 15, 2017, pp. 56-64, XP085152759.
Zuo, (2015). "Chapter 16: Cell Death," Medical Cell Biology, pp. 230-235, 7 pages.
Brezezniak et al., (2016). "RRx-001-Induced Tumor Necrosis and Immune Cell Infiltration in an EGFR Mutation-Positive NSCLC with Resistance to EGFR Tyrosine Kinase Inhibitors: A Case Report," Case Rep Oncol., 9:45-50.
Grisham, (2017). "Pumped Up: Implanted Chemotherapy Device Improves Survival when Colorectal Cancer Spreads to the Liver," available online at <https://www.mskcc.org/news/pumped-implanted-chemotherapy-device-improves-survival-when-colorectal-cancer-spreads-liver>, 5 pages.
Hong et al., (2008). Combining Targeted Therapies, Targeted Cancer Therapy, p. 362, 2 pages.
Pinkel, (1958). "The use of body surface area as a criterion of drug dosage in cancer chemotherapy," Cancer Research, 18:853-856.
Reid et al., (2015). "Safety and activity of RRx-001 in patients with advanced cancer: a first-in-human, open-label, dose-escalation phase 1 study," Lancet Oncol, 16:1133-42.
Thomas, (2016). "Mucositis in Cancer Patients: A Review," available online at <https://www.uspharmacist.com/article/mucositis-in-cancer-patients-a-review#:~:text=Mucositis%20is%20a%20common%20complication,the%20gastrointestinga%20(GI)%20tract.&text=Although%20mucositis%20can%20occur%20anywhere,site%22is%20the%20oral%20cavity>, 10 pages.
Zervoudakis et al., (2017). "Treatment Options in Colorectal Liver Metastases: Hepatic Arterial Infusion," Visc Med, 33:47-53.
Office Action received for U.S. Appl. No. 16/960,443 dated May 28, 2021, 25 pages.
ClinicalTrials.gov, (2015). "NCT01359982: Safety and Pharmacokinetic Study of RRx-001 in Cancer Subjects (DINAMIC)," available online at <https://clinicaltrials.gov/ct2/show/NCT02096354?term=RRx-001 &draw=1 &rank=11>, 7 pages.
ClinicalTrials.gov, (2016). "NCT02096341: A Phase 1 Pilot Study of the Subcutaneous (s.c.) Route to Facilitate the Administration of RRx-001," available online at <https://clinicaltrials.gov/ct2/show/NCT02096341 ?term=RRx-001 &draw=1 &rank=3>, 5 pages.
ClinicalTrials.gov, (2019). "NCT02452970: RRx-001 in Second Line Treatment of Advanced Cholangiocarcinoma Prior to Readministration of First-Line Therapy (EPIC)," available online at <https://clinicaltrials.gov/ct2/show/NCT02452970?term=RRx-001&draw=3&rank=1>, 6 pages.
ClinicalTrials.gov, (2019). "NCT02518958: A Phase I, Open-Label, Multiple Ascending Dose Study of RRx-001 and Nivolumab (PRIMETIME)," available online at <https://clinicaltrials.gov/ct2/show/NCT02518958?term=RRx-001&draw=1&rank=7>, 6 pages.
ClinicalTrials.gov, (2021). "NCT03699956: RRx-001 Sequentially With a Platinum Doublet or a Platinum Doublet in Third-Line or Beyond in Patients With Small Cell Lung Cancer (Replatinum)," available online at <https://clinicaltrials.gov/ct2/show/NCT03699956?term=RRx-001&draw=1&rank=5>, 8 pages.
ClinicalTrials.gov, (2022). "NCT02096354: A Phase 2 Randomized, Open-Label Study of RRx-001 vs Regorafenib in Subjects With Metastatic Colorectal Cancer (ROCKET)," available online at <https://clinicaltrials.gov/ct2/show/NCT02096354?term=RRx-001&draw=1&rank=8>, 8 pages.
ClinicalTrials.gov, (2022). "NCT02801097: RRx-001 in Combination With Irinotecan in Metastatic or Advanced Cancer (Payload) (Payload)," available online at <https://clinicaltrials.gov/ct2/show/NCT02801097?term=RRx-001&draw=1&rank=6>, 6 pages.
ClinicalTrials.gov, (2022). "NCT02871843: RRx-001 + Radiation + Temozolomide In Newly Diagnosed Glioblastoma and Anaplastic Gliomas (G-Force-1)," available online at <https://clinicaltrials.gov/ct2/show/NCT02096354?term=RRx-001&draw=1&rank=9>, 8 pages.
ClinicalTrials.gov, (2022). "NCT04525014: RRx-001 Given With Irinotecan and Temozolomide for Pediatric Patients With Recurrent or Progressive Malignant Solid and Central Nervous System Tumors (PIRATE)," available online at <https://clinicaltrials.gov/ct2/show/NCT02096341 ?term=RRx-001&draw=1&rank=3>, 10 pages.
European Supplementary Search Report for European Patent Application No. EP12839088.7, dated Apr. 28, 2015, 4 pages.
Final Office Action received for U.S. Appl. No. 13/655,618 dated Jun. 12, 2014, 6 pages.
Final Office Action received for U.S. Appl. No. 13/655,618 dated Sep. 11, 2013, 4 pages.
Final Office Action received for U.S. Appl. No. 14/965,062 dated Feb. 6, 2017, 6 pages.
Final Office Action received for U.S. Appl. No. 16/284,035 dated May 26, 2022, 28 pages.
Final Office Action received for U.S. Appl. No. 16/284,035 dated Nov. 15, 2021, 24 pages.
Office Action received for U.S. Appl. No. 12/397,651 dated Feb. 11, 2011, 10 pages.
Office Action received for U.S. Appl. No. 12/397,651 dated Feb. 23, 2012, 8 pages.
Office Action received for U.S. Appl. No. 13/655,618 dated Feb. 25, 2014, 6 pages.
Office Action received for U.S. Appl. No. 13/655,618 dated May 2, 2013, 9 pages.
Office Action received for U.S. Appl. No. 14/849,783 dated Jan. 15, 2016, 5 pages.
Office Action received for U.S. Appl. No. 14/965,062 dated Aug. 11, 2016, 10 pages.
Office Action received for U.S. Appl. No. 14/965,062 dated Dec. 18, 2017, 8 pages.
Office Action received for U.S. Appl. No. 15/298,735 dated Aug. 30, 2018, 9 pages.
Office Action received for U.S. Appl. No. 15/669,403 dated Sep. 14, 2018, 9 pages.
Office Action received for U.S. Appl. No. 15/989,862 dated Feb. 8, 2019, 6 pages.
Office Action received for U.S. Appl. No. 16/284,035 dated Apr. 13, 2021, 17 pages.
Office Action received for U.S. Appl. No. 16/353,047 dated Aug. 31, 2020, 7 pages.
Office Action received for U.S. Appl. No. 16/712,148 dated Oct. 7, 2020, 7 pages.

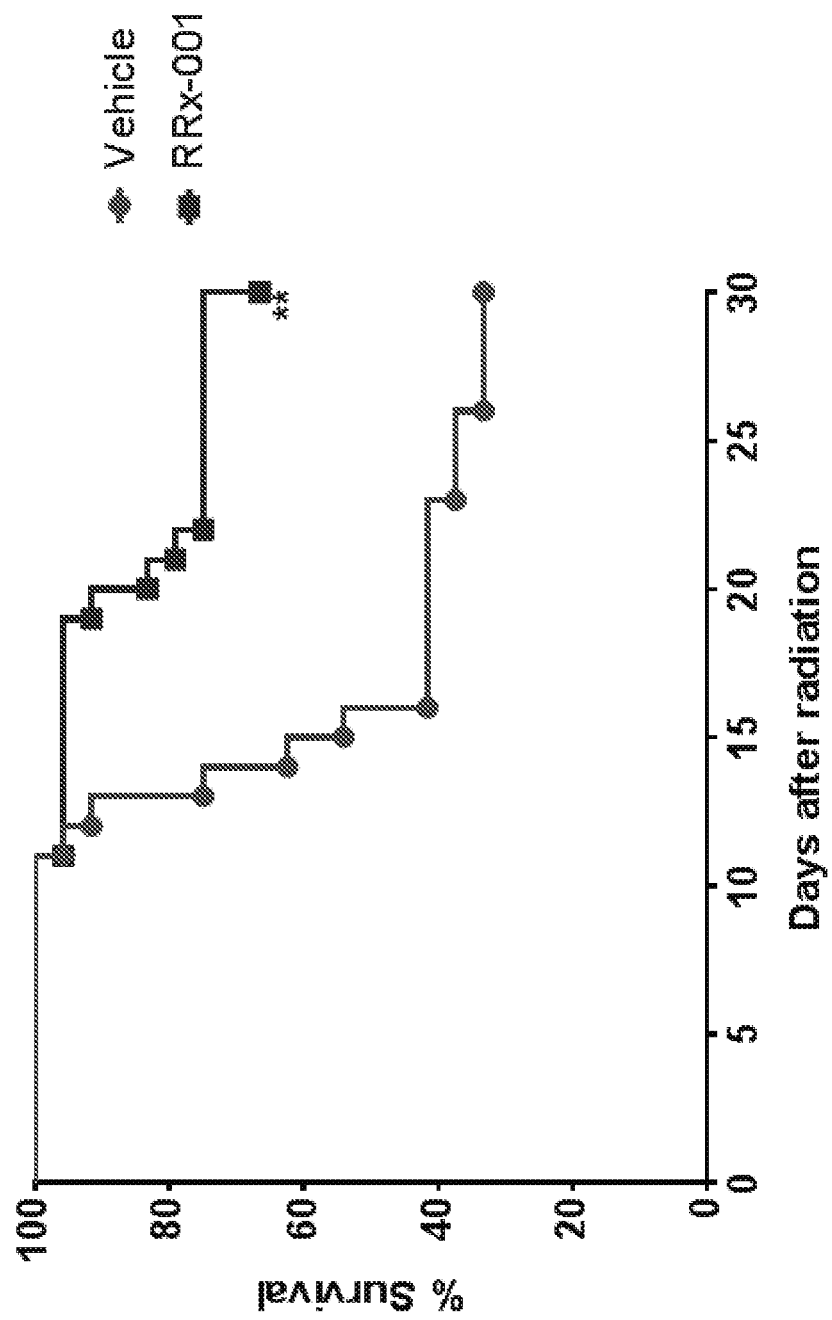

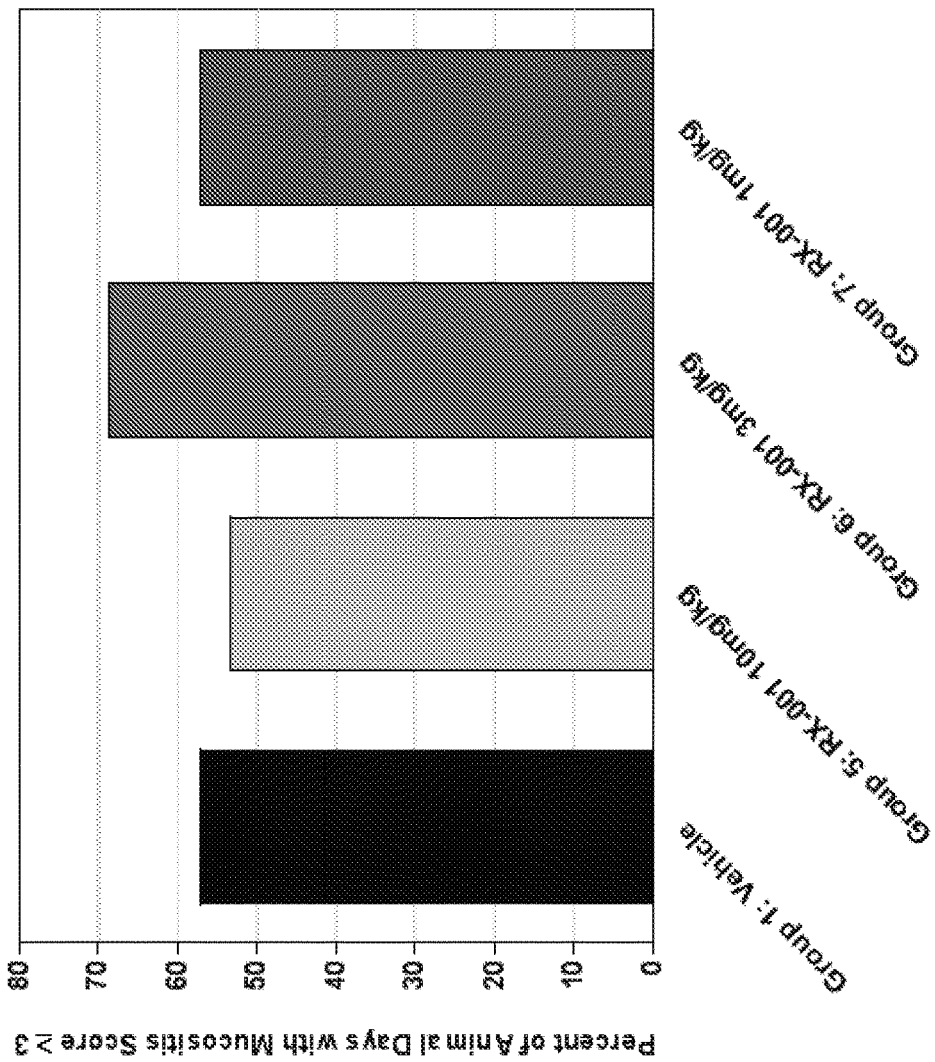

Rank Sum Analysis by Day

| Group | 6 | 8 | 10 | 12 | 14 | 16 | 18 | 20 | 22 | 24 | 26 | 28 |
|---|---|---|---|---|---|---|---|---|---|---|---|---|
| Vehicle vs. RX-001 (10mg/kg) | 0.3778 | 0.4010 | <0.0001 | <0.0001 | <0.0001 | 0.1385 | 1.0 | 0.1385 | 0.1627 | 0.1087 | 0.2225 | 0.2225 |
| Vehicle vs. RX-001 (3mg/kg) | 1.0 | 0.4331 | 0.2734 | 0.4839 | 1.0 | 1.0 | 1.0 | 1.0 | 0.4839 | 0.6539 | 0.2200 | 0.7043 |
| Vehicle vs. RX-001 (1mg/kg) | 0.4839 | 0.4331 | 0.0432 | 0.4839 | 0.0008 | 0.1012 | 1.0 | 0.4839 | 0.6539 | 1.0 | 0.7043 | 1.0 |

B

Rank Sum Analysis by Day

| Group | 6 | 8 | 10 | 12 | 14 | 16 | 18 | 20 | 22 | 24 | 26 | 28 |
|---|---|---|---|---|---|---|---|---|---|---|---|---|
| Vehicle vs. RX-001 (10mg/kg) | 0.4839 | 0.2200 | 0.0010 | 0.2092 | 0.0051 | 1.0 | 1.0 | 0.2092 | 0.4851 | 0.6944 | 0.7089 | 1.0 |
| Vehicle vs. RX-001 (3mg/kg) | 0.7330 | | 0.0012 | | 0.1012 | 0.4839 | 1.0 | 1.0 | 0.4839 | 0.1012 | | 0.7043 |
| Vehicle vs. RX-001 (1mg/kg) | 0.4839 | 0.7043 | 0.0023 | 0.1012 | 0.0024 | 1.0 | 1.0 | 1.0 | 0.4839 | 0.6539 | 1.0 | 1.0 |

FIGURE 16

| Group | 6 | 8 | 10 | 12 | 14 | 16 | 18 | 20 | 22 | 24 | 26 | 28 |
|---|---|---|---|---|---|---|---|---|---|---|---|---|
| Group 1: Vehicle | 0.0 | 0.0 | 0.0 | 0.0 | 100.0 | 100.0 | 100.0 | 100.0 | 87.5 | 75.0 | 62.5 | 62.5 |
| Group 2: RX-001 10mg/kg | 0.0 | 0.0 | 0.0 | 40.0 | 60.0 | 80.0 | 100.0 | 80.0 | 60.0 | 40.0 | 40.0 | 40.0 |
| Group 3: RX-001 3mg/kg | 0.0 | 0.0 | 0.0 | 12.5 | 100.0 | 100.0 | 100.0 | 100.0 | 100.0 | 87.5 | 87.5 | 75.0 |
| Group 4: RX-001 1mg/kg | 0.0 | 0.0 | 12.5 | 12.5 | 43.8 | 75.0 | 100.0 | 87.5 | 75.0 | 75.0 | 75.0 | 62.5 |
| Group 5: RX-001 10mg/kg | 0.0 | 0.0 | 12.5 | 14.3 | 57.1 | 100.0 | 100.0 | 85.7 | 100.0 | 64.3 | 71.4 | 57.1 |
| Group 6: RX-001 3mg/kg | 12.5 | 12.5 | 12.5 | 37.5 | 75.0 | 100.0 | 100.0 | 100.0 | 100.0 | 100.0 | 100.0 | 75.0 |
| Group 7: RX-001 1mg/kg | 0.0 | 0.0 | 0.0 | 25.0 | 50.0 | 100.0 | 100.0 | 100.0 | 100.0 | 87.5 | 62.5 | 62.5 |

Percent Ulceration by Day (Score ≥3)

METHODS AND COMPOSITIONS UTILIZING RRX-001 COMBINATION THERAPY FOR RADIOPROTECTION

PRIORITY

This application is the U.S. National Stage of PCT/US2019/012696, filed Jan. 8, 2019, which claims priority to U.S. Provisional Application Ser. No. 62/614,595, filed Jan. 8, 2018, and 62/737,096, filed Sep. 26, 2018, the contents of which are each incorporated by reference in its entirety.

STATEMENT OF FEDERAL FUNDING

This invention was made with government support under Grant No. RAB2436118 awarded by the U.S. Armed Forces Radiobiology Research Institute (AFRRI). The government has certain rights in the invention.

FIELD OF THE INVENTION

Described are therapeutic methods, kits, and pharmaceutical compositions for protecting a subject from radiation using a combination of (i) a first therapeutic agent selected from the group consisting of 2-bromo-1-(3,3-dinitroazetidin-1-yl)ethan-1-one (RRx-001) and a pharmaceutically acceptable salt thereof and (ii) a second therapeutic agents that reduces the effect of radiation on a subject, such as amifostine and/or a cytokine, where an exemplary therapeutic method involves administering combination to the subject prior to the subject being exposed to the radiation, in order to protect the subject against radiation, such as ionizing radiation containing α-rays, β-rays, γ-rays, neutron radiation, or a combination thereof.

BACKGROUND OF THE INVENTION

Ionizing radiation causes damage to normal tissues, ranging from genetic mutations to cell death. The harmful effects of ionizing radiation on normal tissues are a major concern for military and emergency responders to nuclear accidents and terrorist events due to the risk of acute and delayed radiation injuries. Additionally, radioprotection is a critical issue in cancer treatment. Despite significant technological improvements in radiation delivery in recent years, normal tissue toxicity remains a major dose-limiting factor in therapeutic radiology.

The development of safer and more effective radioprotection techniques is important for protecting civilians and military personnel from unintended radiation exposure. Such radiation may arise from nuclear power sources, nuclear emergencies, medical instrumentation that emits high levels of radiation, exposure to sunlight that has not been filtered through each of the earth's atmospheric layers, and from other sources. It is well known that radiation exposure can lead to cancer, such as, for example, leukemia. High-doses of radiation can also be lethal to humans and animal subjects. For these reasons, safer and more effective radioprotection techniques are needed.

RRx-001 (also called ABDNAZ), which has the chemical name 2-bromo-1-(3,3-dinitroazetidin-1-yl)ethan-1-one, is a small cyclic nitro compound that has previously been found to induce a number of enzymatic and epigenetic alterations in tumor cells. RRx-001 has been used clinically in combination with chemotherapy and/or radiation as a chemo- and radiosensitizer and is described in, for example, international patent application publication WO 2007/022225 describing various compounds and their use in treating medical disorders, such as cancer. Exemplary scientific publications describing benefits observed in human clinical trials evaluating efficacy of RRx-001 in treating patients suffering from cancer include Carter et al. in *Respir. Med. Case Rep.* (2016) vol. 18, pages 62-65; Kim et al. in *Transl. Oncol.* (2016) vol. 9(2), pages 108-113; and Reid et al. in *Case Rep. Oncol.* (2014) vol. 7(1), pages 79-85.

SUMMARY OF THE INVENTION

The present disclosure provides therapeutic methods, kits, and pharmaceutical compositions for protecting a subject from radiation using a radiotherapeutic combination of (i) a first therapeutic agent selected from the group consisting of 2-bromo-1-(3,3-dinitroazetidin-1-yl)ethan-1-one (RRx-001) and a pharmaceutically acceptable salt thereof and (ii) a second therapeutic agent that reduces the effect of radiation on a subject, such as amifostine and/or a cytokine, where an exemplary therapeutic method involves administering the radiotherapeutic combination to the subject prior to the subject being exposed to the radiation, in order to protect the subject against radiation, such as ionizing radiation containing α-rays, β-rays, γ-rays, neutron radiation, or a combination thereof. The therapeutic methods have particular application in protecting civilians and military personnel from unintended radiation exposure, such as protecting first responders to a nuclear emergency, cosmic radiation associated with extended space habitat or travel, or other hazard involving harmful levels of radiation. In addition, the therapeutic methods can be employed in combination with radiation treatment for cancer for the protection of normal tissues. In some embodiments, the RRx-001 increases the radioprotective effect of the second therapeutic agent on a subject compared to the radioprotective effect of the second therapeutic agent alone on a subject. In some embodiments, the RRx-001 increases the radioprotective effect of amifostine compared to the radioprotective effect of amifostine alone. The radiotherapeutic combination is desirably administered to the subject at least 1 hour, 2 hours, 6 hours, 12 hours, 24 hours, 36 hours, 48 hours, 3 days, 4 days, 5 days, 6 days, 1 week, 2 weeks, 3 weeks, or 4 weeks prior to the subject being exposed to radiation that could cause harm to the subject, and desirably provides protection against the harmful effects of radiation for a duration of at least 6 hours, 12 hours, 24 hours, 36 hours, 48 hours, 3 days, 4 days, 5 days, 6 days, 1 week, 2 weeks, 3 weeks, 4 weeks, or longer. The radiotherapeutic combination is desirably administered to the subject through a procedure that minimizes pain experienced by the patient due to receiving the radiotherapeutic combination, such as by slow administration of the radiotherapeutic combination or by administering the radiotherapeutic combination after mixing with blood in order to reduce pain experienced by the patient. The invention having been generally described is explained in more detail in the aspects and embodiments below and in the detailed description.

Accordingly, one aspect of the disclosure provides a method for treating a subject in need of protection against radiation. The method comprises administering to the subject in need thereof an effective amount of radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine, by a route selected from the group consisting of parenteral administration, oral administration, and topical administration, to thereby protect the subject against radiation for a duration of at least 6 hours, 12 hours, 24 hours, 36 hours, 48 hours, 3 days, 4 days, 5 days, 6 days, 1 week, 2 weeks, 3 weeks, 4 weeks, or longer. The first therapeutic agent and/or second therapeutic agent of the radiotherapeutic combination desirably is administered to the subject by intravenous injection, intraperitoneal injection, subcutaneous injection, oral administration, or topical administration. In some embodiments, the first therapeutic agent and the second therapeutic agent of the radiotherapeutic combination are administered together, separately, or intermittently. In some embodiments, the first therapeutic agent and the second therapeutic agent of the radiotherapeutic combination are administered in the same composition or separate compositions. At least one dose of the radiotherapeutic combination is desirably administered to the subject prior to exposure to radiation.

Another aspect of the disclosure provides a method for reducing radiation-exposure damage to a subject. The method comprises administering to the subject in need thereof an effective amount of a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine, by a route selected from the group consisting of parenteral administration, oral administration, and topical administration, to thereby reduce radiation-exposure damage to the subject for a duration of at least 6 hours. The first therapeutic agent and/or second therapeutic agent of the radiotherapeutic combination desirably is administered to the subject by intravenous injection, intraperitoneal injection, subcutaneous injection, oral administration, or topical administration. In some embodiments, the first therapeutic agent and the second therapeutic agent of the radiotherapeutic combination are administered together, separately, or intermittently. In some embodiments, the first therapeutic agent and the second therapeutic agent of the radiotherapeutic combination are administered in the same composition or separate compositions. At least one dose of the radiotherapeutic combination is desirably administered to the subject prior to exposure to radiation.

Another aspect of the disclosure provides a method for protecting biological material, such as isolated cells, tissues or organs, from the damaging effects of radiation. The method comprises exposing the biological material to an effective amount of a therapeutic agent selected from the group consisting of RRx-001 and a pharmaceutically acceptable salt thereof, to thereby protect the biological material from the damaging effects of radiation for a duration of at least 6 hours, 12 hours, 24 hours, 36 hours, 48 hours, 3 days, 4 days, 5 days, 6 days, 1 week, 2 weeks, 3 weeks, 4 weeks, or longer. The first therapeutic agent desirably is RRx-001. In some embodiments, the first therapeutic agent and the second therapeutic agent of the radiotherapeutic combination are contacted with the biological material together, separately, or intermittently. In some embodiments, the first therapeutic agent and the second therapeutic agent of the radiotherapeutic combination are contacted with the biological material in the same composition or separate compositions. The biological material is desirably exposed to at least one dose of the radiotherapeutic combination prior to exposure to the radiation.

Therapeutic agents described herein may be formulated as a pharmaceutical composition. One or more of the foregoing may be contained in a kit with instructions for use, as further described herein.

BRIEF DESCRIPTION OF THE DRAWINGS

FIG. 1A illustrates the effects of RRx-001 treatment (10 mg/kg) on survival advantage following radiation (9.35 Gy (LD70/30) at 0.6 Gy/min) compared to an irradiated vehicle control. Data is presented as a 30 Day Survival Kaplan Meyer plot. N=24/group; p<0.005.

FIG. 13 illustrates exemplary data for the effects of RRx-001 on alleviation of mucositis in a hamster model.

FIG. 14 illustrates exemplary data for the effects of RRx-001 on alleviation of mucositis in a hamster model. FIG. 14B provides data for percent of days with Mucositis scores≥3 for the entire study duration for the once per week dosing groups. To examine the levels of clinically significant mucositis, as defined by presentation with open ulcers (a score of ≥3), the total number of days in which an animal exhibited an elevated score was summed and expressed as a percentage of the total number of days scored for the entire study duration (Day 6-28). Statistical significance was evaluated using the Chi-square test in comparison to Vehicle Control. ***$p<0.001$.

FIG. 15 illustrates exemplary data for the comparison of daily mucositis scores (Groups Dosed −4, −1, 1, 4, 7, 11, 14, 18, 21, and 25). FIG. 15A provides data for the twice per week dosing groups. FIG. 15B provides data for the once per week dosing groups. The significance of group differences observed in daily mucositis scores was determined using the Mann-Whitney rank sum test. This nonparametric statistic is appropriate for the visual mucositis scoring scale. The p-values for each calculation are shown. Light grey shading denotes decrease in mucositis scores compared to Vehicle Group (improvement of disease), dark grey denotes increase in mucositis scores (worsening of disease). Bold font denotes significant difference in mucositis scores.

FIG. 16 illustrates exemplary data for the percentages of animals with ulceration by day with a mucositis score≥3. To examine the levels of clinically significant mucositis, as defined by presentation with open ulcers (score≥3), the percentage of animals from each treatment group that exhibited an open ulcer on each day of the study was determined. Light shading denotes decrease in mucositis scores compared to Vehicle Group (improvement of disease), dark shading denotes increase in mucositis scores (worsening of disease).

DETAILED DESCRIPTION OF THE INVENTION

Definitions

Figure 1B:
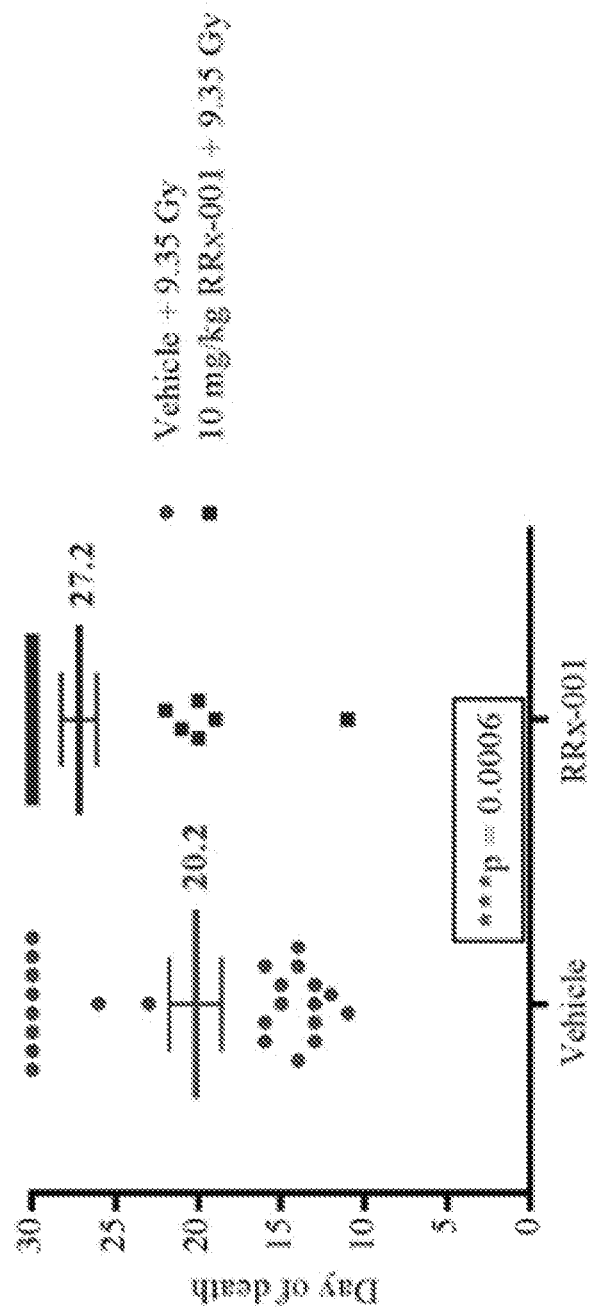
FIG. 1B provides a scatterplot of the survival times by treatment group. The means±standard errors are 20.2±1.6 and 27.2±1.1 for vehicle and RRx-001 groups, respectively. *p<0.0006.

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the terms "patient" and "subject" refer to organisms to be treated by the methods of the present disclosure. Such organisms are preferably mammals (e.g., marines, simians, equines, bovines, porcinis, canines, felines, and the like), and more preferably humans.

As used herein, the term "effective amount" refers to the amount of a compound (e.g., a compound of the present disclosure) sufficient to effect beneficial or desired results. An effective amount can be administered in one or more administrations, applications, or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "alleviate" and "alleviating" refer to reducing the severity of the condition, such as reducing the severity by, for example, at least 10%, 20%, 30%, 40%, 50%, 60%, 70%, 80%, 90%, or 95%.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, for example, Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present disclosure which, upon administration to a subject, is capable of providing a compound of this disclosure or an active metabolite or residue thereof. As is known to those of skill in the art, "salts" of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the disclosure and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula NW4+, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as Na+, $NH_4+$, and $NW_4+$ (wherein W is a C1-4 alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as ±10%, ±5%, ±1%, or ±0.1% of the specified value.

The compound RRx-001 (also called ABDNAZ) has the chemical name 2-bromo-1-(3,3-dinitroazetidin-1-yl)ethan-1-one, which has the following chemical structure:

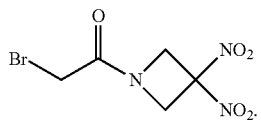

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

Figure 6A:
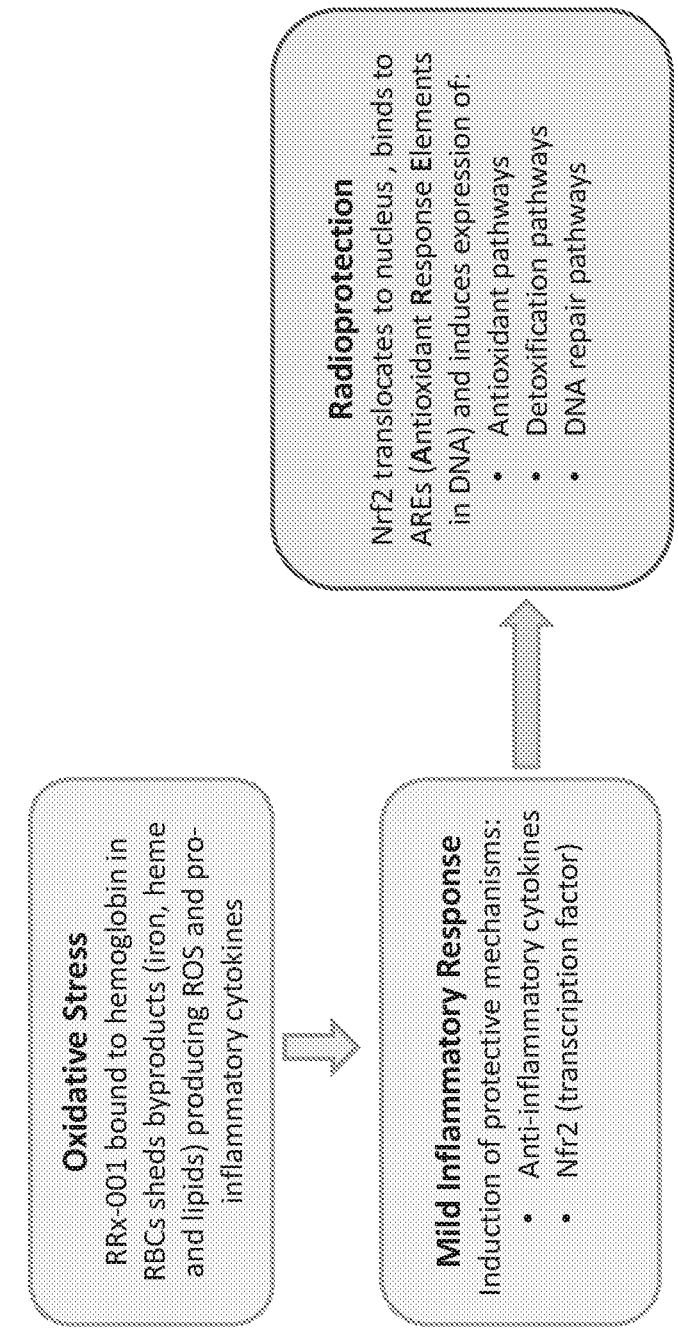
FIG. 6 illustrates exemplary potential mechanisms for radioprotection by RRx-001 through antioxidant pathways (FIG. 6A) or the metabolic stress response (FIG. 6B).
Figure 6B:
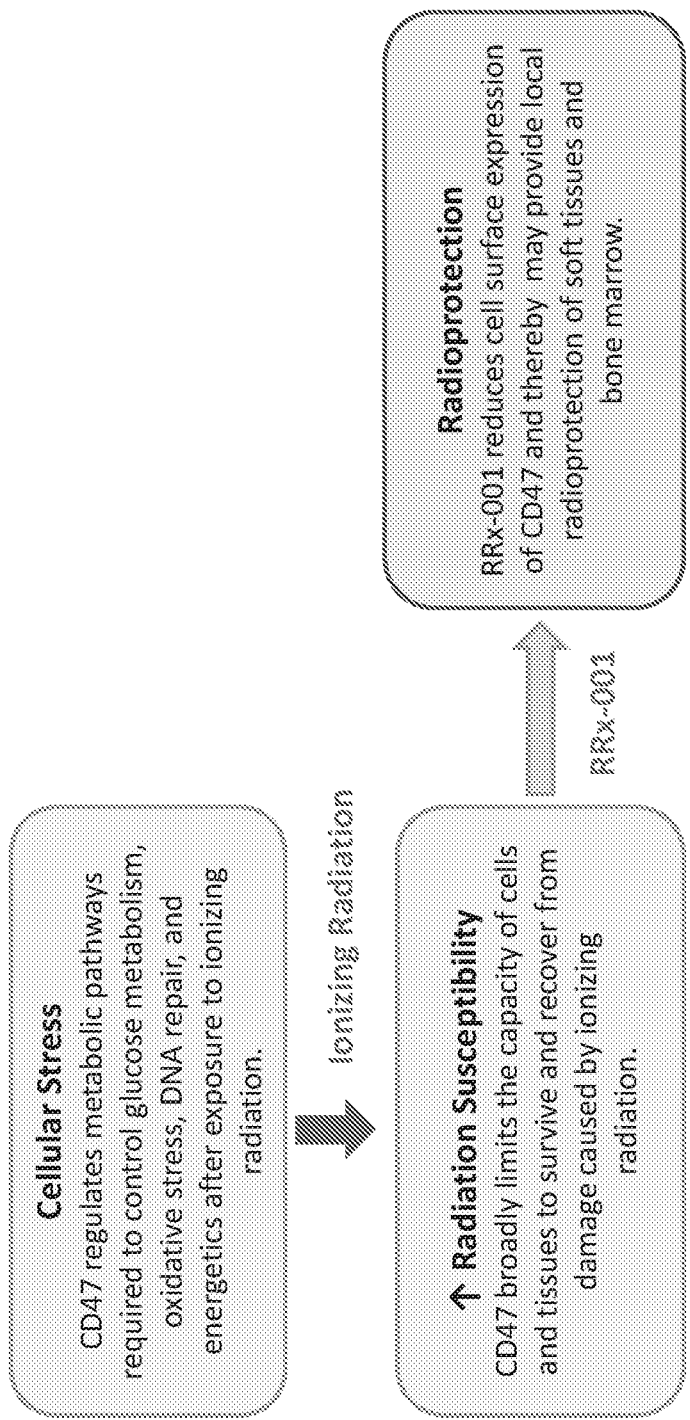

As a general matter, compositions specifying a percentage are by weight unless otherwise specified. Further, if a variable is not accompanied by a definition, then the previous definition of the variable controls Overview Prophylactic radioprotective compounds that can protect normal tissue from the effects of ionizing radiation are an unmet need for military and first responders, space exploration, and cancer treatment. RRx-001 is a small cyclic nitro compound, 1-bromoacetyl-3,3-dinitroazetidine, which forms an RRx-001-hemoglobin adduct in red blood cells (RBC). RRx-001 is a systemically non-toxic anticancer agent that has been employed as a chemo- and radio-sensitizer for various tumors types in multiple clinical trials. In contrast with its ability to effect tumor radiosensitization, RRx-001 has been shown to protect normal cells from radiation. As described in the Examples provided herein, administration of RRx-001 prior to exposure to lethal radiation significantly increased survival in mice. Further, in sublethally irradiated mice, prophylactic administration of RRx-001 was found to significantly augment cellular recovery in bone marrow as evidenced by accelerated myeloreconstitution and improved bone marrow cellularity. In addition, RRx-001 treatment was found to increase expression of antioxidant response element proteins, such as heme oxygenase 1 (HO-1), in macrophages, monocytes, and mesenchymal stem cells. Induction of antioxidant response element genes may be driven by the transcription factor Nrf2, which has previously been shown to have increased nuclear presence in tumor cells exposed to RRx-001 (Ning et al., Oncotarget 2015; 6(25):21547). Without wishing to be bound by theory, RRx-001 may provide cellular protection from oxidative injury via oxidative preconditioning whereby brief shifts in redox balance induce a precondition state of compensatory gene expression for antioxidant responses that are cytoprotective (see FIG. 6A). In addition, RRx-001 reduces the cell surface expression of the transmembrane protein CD47 (cluster differentiation 47), which may provide local radioprotection of soft tissues and bone marrow given that CD47 expression following exposure to ionizing radiation is known to limit the ability of cells and tissues to survive and recover from damage caused by ionizing radiation (Miller et al. (2015) J. Biol. Chem. 290: 24858-24874) (see FIG. 6B).

The present disclosure provides therapeutic methods, kits, and pharmaceutical compositions for protecting a subject from radiation using a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine. Administration of the first therapeutic agent in combination with the second therapeutic agent desirably provides a superior protective effect relative to administration of the first therapeutic agent without the second therapeutic agent.

In an exemplary therapeutic method, the radiotherapeutic combination is administered to the subject prior to the subject being exposed to the radiation, in order to protect the subject against radiation, such as ionizing radiation containing α-rays, β-rays, γ-rays, neutron radiation or a combination thereof. The therapeutic methods have particular application in protecting civilians and military personnel from unintended radiation exposure, such as protecting first responders to a nuclear emergency, cosmic radiation associated with extended space habitat or travel, or other hazard involving harmful levels of radiation. In addition, the therapeutic methods utilizing a radiotherapeutic combination provided herein can be employed in combination with radiation treatment for cancer for the protection of normal tissues. The radiotherapeutic combination is desirably administered to the subject at least about 1 hour, 2 hours, 6 hours, 12 hours, 24 hours, 36 hours, 48 hours, 3 days, 4 days, 5 days, 6 days, 1 week, 2 weeks, 3 weeks, or 4 weeks prior to the subject being exposed to radiation that could cause harm to the subject, and desirably provides protection against the harmful effects of radiation for a duration of at least about 6 hours, 12 hours, 24 hours, 36 hours, 48 hours, 3 days, 4 days, 5 days, 6 days, 1 week, 2 weeks, 3 weeks, 4 weeks, or longer.

Methods for Protecting Against and Reducing Effects of Radiation

Provided herein are methods for protecting a subject from radiation using a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine. Various features of the methods are described in sections below. The sections are arranged for convenience and information in one section is not limited to that section, but may be applied to other sections.

One aspect of the present disclosure provides methods for treating a subject in need of protection against radiation. In some embodiments, the method comprises administering to the subject in need thereof an effective amount of a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine. In some embodiments, the first therapeutic agent and/or second therapeutic agent of the radiotherapeutic combination are administered by a route selected from the group consisting of parenteral administration, oral administration, and topical administration, to thereby protect the subject against radiation for a duration of at least about 6 hours, 12 hours, 24 hours, 36 hours, 48 hours, 3 days, 4 days, 5 days, 6 days, 1 week, 2 weeks, 3 weeks, 4 weeks, or longer. In some embodiments, the first therapeutic agent and the second therapeutic agent of the radiotherapeutic combination are administered together, separately, or intermittently. In some embodiments, the first therapeutic agent and the second therapeutic agent of the radiotherapeutic combination are administered in the same composition or separate compositions. The therapeutic method has particular applications in protecting civilians and military personnel from unintended radiation exposure, such as protecting first responders to a nuclear emergency, cosmic radiation associated with extended space habitat or travel, or other hazard involving harmful levels of radiation. The therapeutic method can also be employed in combination with radiation therapy of a subject for cancer for the purpose of protecting the subject against radiation.

Another aspect of the present disclosure provides methods of reducing radiation-exposure damage to a subject. In some embodiments, the method comprises administering to the subject in need thereof an effective amount of a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine. In some embodiments, the first therapeutic agent and/or second therapeutic agent of the radiotherapeutic combination are administered by a route selected from the group consisting of parenteral administration, oral and topical administration, to thereby reduce radiation-exposure damage to the subject for a duration of at least 6 hours, 12 hours, 24 hours, 36 hours, 48 hours, 3 days, 4 days, 5 days, 6 days, 1 week, 2 weeks, 3 weeks, 4 weeks, or longer. In some embodiments, the first therapeutic agent and the second therapeutic agent of the radiotherapeutic combination are administered together, separately, or intermittently. In some embodiments, the first therapeutic agent and the second therapeutic agent of the radiotherapeutic combination are administered in the same composition or separate compositions. The therapeutic method has particular applications in protecting civilians and military personnel from unintended radiation exposure, such as protecting first responders to a nuclear emergency, cosmic radiation associated with extended space habitat or travel, or other hazard involving harmful levels of radiation. The therapeutic method can also be employed for reducing radiation-exposure damage associated with radiation therapy for cancer in a subject.

In some embodiments, administration of the radiotherapeutic combination reduces or inhibits radiation-exposure damage to one or more cells, systems, organs, or normal tissues in a subject. In some embodiments, administration of the radiotherapeutic combination reduces or inhibits radiation-exposure damage to one or more of bone marrow, lymphatic system, immune system, mucosal tissue, mucosal immune system, gastrointestinal system, cardiovascular system, nervous system, reproductive organs, prostate, ovaries, lung, kidney, skin and brain. In some embodiments, administration of the radiotherapeutic combination reduces or inhibits one or more radiation-induced conditions, such as, but not limited to oral mucositis, dermatitis, skin rash, ulceration, alopecia, gastrointestinal distress, or proctitis.

Another aspect of the present disclosure provides methods of protecting biological material, such as isolated cells, tissues or organs, from the damaging effects of radiation. In some embodiments, the method comprises exposing said biological material to an effective amount of a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine, to thereby protect the biological material from the damaging effects of radiation for a duration of at least about 6 hours, 12 hours, 24 hours, 36 hours, 48 hours, 3 days, 4 days, 5 days, 6 days, 1 week, 2 weeks, 3 weeks, 4 weeks, or longer.

Another aspect of the present disclosure provides methods for treating a subject in need of protection against radiation using a radiotherapeutic combination of (i) a first therapeutic agent that alkylates hemoglobin beta cysteine 93 and (ii) a second therapeutic agent that reduces the effect of radiation on a subject, such as amifostine and/or a cytokine. In some embodiments, the agent that alkylates hemoglobin beta cysteine 93 is selected from the group consisting of RRx-001 and a pharmaceutically acceptable salt thereof. In some embodiments, the method comprises administering to the subject in need thereof an effective amount of a radiotherapeutic combination of (i) a first therapeutic agent that alkylates hemoglobin beta cysteine 93 and (ii) a second therapeutic agent that reduces the effect of radiation on a subject, such as amifostine and/or a cytokine, to thereby protect the subject against radiation for a duration of at least 2 hours, 6 hours, 12 hours, 24 hours, 36 hours, 48 hours, 3 days, 4 days, 5 days, 6 days, 1 week, 2 weeks, 3 weeks, 4 weeks, or longer. In certain embodiments, first therapeutic agent and/or second therapeutic agent of the radiotherapeutic combination is administered by a route selected from the group consisting of parenteral administration, oral administration, and topical administration. In some embodiments, the first therapeutic agent and the second therapeutic agent of the radiotherapeutic combination are administered together, separately, or intermittently. In some embodiments, the first therapeutic agent and the second therapeutic agent of the radiotherapeutic combination are administered in the same composition or separate compositions. In certain embodiments, the method protects the subject against radiation for a duration of at least 6 hours. The therapeutic method has particular applications in protecting civilians and military personnel from unintended radiation exposure, such as protecting first responders to a nuclear emergency, cosmic radiation associated with extended space habitat or travel, or other hazard involving harmful levels of radiation. The therapeutic method can also be employed in combination with radiation therapy of a subject for cancer for the purpose of protecting the subject against radiation.

Another aspect of the present disclosure provides a method of reducing radiation-exposure damage to a subject using a radiotherapeutic combination of (i) a first therapeutic agent that alkylates hemoglobin beta cysteine 93 and (ii) a second therapeutic agent that reduces the effect of radiation on a subject, such as amifostine and/or a cytokine. In some embodiments, the agent that alkylates hemoglobin beta cysteine 93 is selected from the group consisting of RRx-001 and a pharmaceutically acceptable salt thereof. The method comprises administering to the subject in need thereof an effective amount of a radiotherapeutic combination of (i) a first therapeutic agent that alkylates hemoglobin beta cysteine 93 and (ii) a second therapeutic agent that reduces the effect of radiation on a subject, such as amifostine and/or a cytokine, to thereby reduce radiation-exposure damage to the subject for a duration of at least 2 hours, 6 hours, 12 hours, 24 hours, 36 hours, 48 hours, 3 days, 4 days, 5 days, 6 days, 1 week, 2 weeks, 3 weeks, 4 weeks, or longer. In certain embodiments, the first therapeutic agent and/or second therapeutic agent of the radiotherapeutic combination is administered by a route selected from the group consisting of parenteral administration and topical administration. In certain embodiments, the method reduces radiation-exposure damage to the subject for a duration of at least 6 hours. The therapeutic method has particular applications in protecting civilians and military personnel from unintended radiation exposure, such as protecting first responders to a nuclear emergency, cosmic radiation associated with extended space habitat or travel, or other hazard involving harmful levels of radiation. The therapeutic method can also be employed for reducing radiation-exposure damage associated with radiation therapy for cancer in a subject.

In certain other embodiments, the therapeutic agent that alkylates hemoglobin beta cysteine 93 comprises a maleimide. In certain embodiments, the therapeutic agent comprises an N-alkyl maleimide. In certain embodiments, the therapeutic agent comprises N-ethyl maleimide. In certain other embodiments, the therapeutic agent comprises a compound selected from the group consisting of an a-haloacetate, an a-haloacetamide, and an a-halomethylketone. In certain embodiments, the therapeutic agent is an a-haloacetate. In certain embodiments, the therapeutic agent comprises a-bromoacetate or a-iodoacetate. In certain other embodiments, the therapeutic agent comprises an a-haloacetamide. In certain embodiments, the therapeutic agent comprises a-bromoacetamide or a-iodoacetamide. In certain other embodiments, the therapeutic agent comprises an a-halomethylketone. In certain embodiments, the therapeutic agent comprises a-bromobenzophenone or a-iodobenzophenone. In certain embodiments, the therapeutic agent comprises a bromomethylketone. In certain embodiments, the therapeutic agent comprises an alpha-iodo-dinitroazetidine or an alpha-chloro-dinitroazetidine.

In certain embodiments, the methods provided herein achieve protection against radiation for a duration of at least 12 hours. In certain embodiments, the method achieves protection against radiation for a duration of at least 48 hours. In yet other embodiments, the method achieves protection against radiation for a duration of from about 6 hours to about 12 hours, from about 6 hours to about 24 hours, from about 12 hours to about 24 hours, or from about 24 hours to about 48 hours. In certain embodiments, the methods provided herein achieve protection against radiation for a duration of at least 1 week. In certain embodiments, the methods provided herein achieve protection against radiation for a duration of at least 1 month.

In certain embodiments, exemplary contemplated benefits of therapeutic methods may include, but are not limited to, (i) limiting the symptoms of acute radiation exposure, (ii) reducing the longer-term complications from radiation exposure, and/or (iii) prophylaxis against formation of cancers known to be caused by radiation exposure (for example, leukemias and thyroid cancers).

Type and Source of the Radiation

The methods provided herein may be characterized according to the type of radiation. For example, in certain embodiments, the radiation is ionizing radiation. In certain embodiments, the radiation comprises α-rays, β-rays, γ-rays, neutron radiation, or a combination thereof. In certain other embodiments, the radiation comprises x-rays.

The method may also be characterized according to the source of the ionizing radiation. For example, in certain embodiments, the radiation is ionizing radiation from sunlight.

In certain other embodiments, the radiation is ionizing radiation from radioactive nuclei. In certain embodiments, the radiation is ionizing radiation from an explosive device.

In certain other embodiments, the radiation is from a medical device that emits therapeutic radiation, e.g. for the treatment of a cancer. Exemplary ionizing radiation treatment modalities can include, for example, external beam radiotherapy; Intensity modulated radiation therapy (IMRT); Image Guided Radiotherapy (IGRT); X Irradiation (e.g. photon beam therapy); electron beam (e.g. beta irradiation); local and total skin electron beam therapy; mega voltage photon treatment (about 4 to 10 MeV); proton irradiation; high linear energy transfer (LET) particles; stereotactic radiosurgery; gamma knife; linear accelerator mediated frameless stereotactic radiosurgery; robot arm controlled x irradiation delivery system; radioisotope radiotherapy for organ specific or cancer cell specific uptake; radioisotope bound to monoclonal antibody for tumor targeted radiotherapy (or radioimmunotherapy, RIT); brachytherapy (interstitial or intracavity) high dose rate radiation source implantation; permanent radioactive seed implantation for organ specific dose delivery.

Methods for Administering the Radiotherapeutic Combination

The therapeutic method may be characterized according to the timing for administering the radiotherapeutic combination. For example, in certain embodiments, at least one dose of the first therapeutic agent and at least one dose of the second therapeutic agent are administered to the subject prior to exposure to the radiation.

In certain embodiments, at least one dose of the first therapeutic agent and at least one dose of the second therapeutic agent are administered to the subject within 1 hour, 2 hours, 6 hours, 12 hours, 24 hours, 36 hours, 48 hours, 3 days, 4 days, 5 days, 6 days, 1 week, 2 weeks, 3 weeks, or 4 weeks prior to exposure to the radiation. In certain embodiments, at least one dose of the first therapeutic agent and at least one dose of the second therapeutic agent are administered to the subject within 48 hours prior to exposure to the radiation. In certain embodiments, at least one dose of the first therapeutic agent and at least one dose of the second therapeutic agent are administered to the subject within 24 hours prior to exposure to the radiation. In certain embodiments, at least one dose of the first therapeutic agent and at least one dose of the second therapeutic agent are administered to the subject within 12 hours prior to exposure to the radiation. In certain embodiments, at least one dose of the first therapeutic agent and at least one dose of the second therapeutic agent are administered to the subject within 6 hours prior to exposure to the radiation. In certain embodiments, at least one dose of the first therapeutic agent and at least one dose of the second therapeutic agent are administered to the subject within 3 hours prior to exposure to the radiation. In certain embodiments, at least one dose of the first therapeutic agent and at least one dose of the second therapeutic agent are administered to the subject within 2 hours prior to exposure to the radiation. In certain embodiments, at least one dose of the first therapeutic agent and at least one dose of the second therapeutic agent are administered to the subject within 1 hour prior to exposure to the radiation. In certain embodiments, at least one dose of the first therapeutic agent and at least one dose of the second therapeutic agent are administered to the subject within 30 minutes prior to exposure to the radiation. In certain embodiments, at least one dose of the first therapeutic agent and at least one dose of the second therapeutic agent are administered to the subject within 15 minutes prior to exposure to the radiation.

In certain other embodiments, a dose of the first therapeutic agent and a dose of the second therapeutic agent are first administered to the subject during exposure to the radiation or after exposure to the radiation has ceased. In certain embodiments, a dose of the first therapeutic agent and a dose of the second therapeutic agent are first administered to the subject during exposure to the radiation. In certain other embodiments, a dose of the first therapeutic agent and a dose of the second therapeutic agent are first administered to the subject after exposure to the radiation has ceased. In certain embodiments, a dose of the first therapeutic agent and a dose of the second therapeutic agent are first administered to the subject within 1 day after exposure to the radiation has ceased. In certain embodiments, a dose of the first therapeutic agent and a dose of the second therapeutic agent are first administered to the subject within 48, 24, 12, 6, 3, or 2 hours after exposure to the radiation has ceased. In certain embodiments, a dose of the first therapeutic agent and a dose of the second therapeutic agent are first administered to the subject within 1 hour after exposure to the radiation has ceased.

In certain other embodiments, a dose of the therapeutic agent is administered to the subject (i) prior to exposure to the radiation and (ii) during exposure to the radiation. In certain other embodiments, a dose of the therapeutic agent is administered to the subject (i) prior to exposure to the radiation and (ii) after exposure to the radiation. In certain other embodiments, a dose of the therapeutic agent is administered to the subject (i) prior to exposure to the radiation, (ii) during exposure to the radiation, and (iii) after exposure to the radiation.

The therapeutic method may be characterized according to the dose of the therapeutic agent. For example, in certain embodiments, the first therapeutic agent is administered at a dosage that provides RRx-001 in an amount ranging from about 0.01 mg to about 1000 mg of RRx-001 on each day the first therapeutic agent is administered to the subject. In certain embodiments, the first therapeutic agent is administered at a dosage that provides RRx-001 in an amount ranging from about 0.05 mg to about 500 mg of RRx-001 on each day the first therapeutic agent is administered to the subject. In certain embodiments, the first therapeutic agent is administered at a dosage that provides RRx-001 in an amount ranging from about 0.1 mg to about 200 mg of RRx-001 on each day the first therapeutic agent is administered to the subject. In certain embodiments, the first therapeutic agent is administered at a dosage that provides RRx-001 in an amount ranging from about 0.5 mg to about 150 mg of RRx-001 on each day the first therapeutic agent is administered to the subject. In certain embodiments, the first therapeutic agent is administered at a dosage that provides RRx-001 in an amount ranging from about 1 mg to about 100 mg of RRx-001 on each day the first therapeutic agent is administered to the subject. In certain embodiments, the first therapeutic agent is administered at a dosage that provides RRx-001 in an amount ranging from about 5 mg to about 50 mg of RRx-001 on each day the first therapeutic agent is administered to the subject. In certain embodiments, the first therapeutic agent is administered at a dosage that provides RRx-001 in an amount ranging from about 0.5 mg to about 166 mg of RRx-001 on each day the first therapeutic agent is administered to the subject.

In certain embodiments, the first therapeutic agent is administered at a dosage that provides RRx-001 in an amount ranging from about 0.005 mg/m$^2$ to about 500 mg/m$^2$ of RRx-001 on each day the first therapeutic agent is administered to the subject. In certain embodiments, the first therapeutic agent is administered at a dosage that provides RRx-001 in an amount ranging from about 0.025 mg/m$^2$ to about 250 mg/m$^2$ of RRx-001 on each day the first therapeutic agent is administered to the subject. In certain embodiments, the first therapeutic agent is administered at a dosage that provides RRx-001 in an amount ranging from about 0.05 mg/m$^2$ to about 100 mg/m$^2$ of RRx-001 on each day the first therapeutic agent is administered to the subject. In certain embodiments, the first therapeutic agent is administered at a dosage that provides RRx-001 in an amount ranging from about 0.25 mg/m$^2$ to about 75 mg/m$^2$ of RRx-001 on each day the first therapeutic agent is administered to the subject. In certain embodiments, the first therapeutic agent is administered at a dosage that provides RRx-001 in an amount ranging from about 0.5 mg/m$^2$ to about 50 mg/m$^2$ of RRx-001 on each day the first therapeutic agent is administered to the subject. In certain embodiments, the first therapeutic agent is administered at a dosage that provides RRx-001 in an amount ranging from about 2.5 mg/m$^2$ to about 25 mg/m$^2$ of RRx-001 on each day the first therapeutic agent is administered to the subject. In certain embodiments, the first therapeutic agent is administered at a dosage that provides RRx-001 in an amount ranging from about 0.25 mg/m$^2$ to about 83 mg/m$^2$ of RRx-001 on each day the first therapeutic agent is administered to the subject.

The therapeutic method may be characterized according to the frequency of administration of the first therapeutic agent. For example, in certain embodiments, the first therapeutic agent is administered to the subject no more frequently than once per week. In certain embodiments, the first therapeutic agent is administered to the subject once per week for at least two weeks. In certain other embodiments, the first therapeutic agent is administered to the subject at least once per week. In certain embodiments, the first therapeutic agent is administered to the subject at least twice per week. In certain embodiments, the first therapeutic agent is administered to the subject at least once per two days. In certain embodiments, the first therapeutic agent is administered to the subject at least once per day. In certain embodiments, the first therapeutic agent is administered to the subject at least twice per day.

In certain embodiments, the second therapeutic agent is administered to the subject no more frequently than once per week. In certain embodiments, the second therapeutic agent is administered to the subject once per week for at least two weeks. In certain other embodiments, the second therapeutic agent is administered to the subject at least once per week. In certain embodiments, the second therapeutic agent is administered to the subject at least twice per week. In certain embodiments, the second therapeutic agent is administered to the subject at least once per two days. In certain embodiments, the second therapeutic agent is administered to the subject at least once per day. In certain embodiments, the second therapeutic agent is administered to the subject at least twice per day.

In certain embodiments, the first therapeutic agent and second therapeutic agent are administered concurrently. In certain embodiments, the first therapeutic agent and second therapeutic agent are administered sequentially on the same day. In certain embodiments, the first therapeutic agent and second therapeutic agent are administered intermittently on different days. In certain embodiments, the first therapeutic agent and second therapeutic agents are administered sequentially at least 1 hour, at least 2 hours, at least 3 hours, at least 4 hours, at least 6 hours, at least 12 hours, at least 24 hours, at least 36 hours, at least 48 hours, at least 3 days, at least 4 days, at least 5 days, at least 6 days, at least a week or longer apart.

The therapeutic method may be characterized according to the route for administration of the therapeutic agents, and the method may be further characterized by the duration of administration. For example, in certain embodiments, the first therapeutic agent and/or second therapeutic agent is administered intravenously to the patient. In certain embodiments, the first therapeutic agent and/or second therapeutic agent is administered intravenously to the subject over a duration of at least thirty minutes. In certain embodiments, the first therapeutic agent and/or second therapeutic agent is administered intravenously to the subject over a duration of at least sixty minutes. In certain embodiments, the first therapeutic agent and/or second therapeutic agent is administered intravenously to the subject over a duration ranging from 30 minutes to 90 minutes.

In certain other embodiments, the first therapeutic agent and/or second therapeutic agent is administered by intravenous injection of a mixture of blood with a composition comprising the first therapeutic agent and/or second therapeutic agent. In some embodiments, a quantity of blood (e.g., about 1 to about 50 mls of blood) is removed from the subject and mixed with a composition comprising the first therapeutic agent and/or second therapeutic agent (e.g., RRx-001 and/or amifostine). The mixture containing the first therapeutic agent and/or second therapeutic agent (e.g., RRx-001 and/or amifostine) is then administered intravenously to the patient. In some embodiments, the blood is mixed with an anticoagulant (e.g., using a syringe preload with an anticoagulant) prior to mixing with the first therapeutic agent and/or second therapeutic agent. In some embodiments, the method of removing the blood from the subject, mixing with the first therapeutic agent and/or second therapeutic agent and administering the mixture to the subject are performed in an aseptic closed system (e.g., connected system of sterile tubing, syringes, containers, and the like), where the blood is not exposed to the environment. In some embodiments, the closed system is flushed with sterile saline where the saline flush is administered to the patient to ensure complete delivery of the first therapeutic agent and/or second therapeutic agent.

In certain other embodiments, the first therapeutic agent is administered by intraperitoneal injection to the subject. In certain embodiments, the first therapeutic agent is administered by intraperitoneal injection to the subject over a duration of at least thirty minutes. In certain other embodiments, the first therapeutic agent is administered by subcutaneous injection. In certain embodiments, the first therapeutic agent is administered by subcutaneous injection to the subject over a duration of at least 5 minutes. In certain other embodiments, the first therapeutic agent is administered subcutaneously to the subject via a pump device implanted in the subject that contains the first therapeutic agent. In certain embodiments, when the first therapeutic agent is administered subcutaneously to the subject via a pump device implanted in the subject that contains the first therapeutic agent, the implanted pump device is an osmotic pump.

In certain other embodiments, the first therapeutic agent and/or second therapeutic agent of the radiotherapeutic combination is administered by topical administration. The topical administration may be, for example, a topical gel containing the first therapeutic agent, which is applied to the skin of the subject. The topical gel may be a sustained release gel that slowly releases the first therapeutic agent over time.

In certain other embodiments, the first therapeutic agent and/or second therapeutic agent of the radiotherapeutic combination is administered by oral administration, such as a pill, a capsule, sublingual tablets, sustained-release formulation, delayed-release formulation, a liquid, or an aerosol.

The therapeutic method may be characterized according to the route for administration of the second therapeutic agent, and the method may be further characterized by the duration of administration. For example, in certain embodiments, the second therapeutic agent is administered intravenously to the patient. In certain embodiments, the second therapeutic agent is administered intravenously to the subject over a duration of less than thirty minutes.

The therapeutic method may be characterized according to the location for administration of the first therapeutic agent and the second therapeutic agent. For example, in certain embodiments, one or both of the first therapeutic agent and the second therapeutic agent are administered in proximity to tissue desired to be protected from radiation. In certain embodiments, the first therapeutic agent and the second therapeutic agent are administered in proximity to tissue desired to be protected from radiation. In certain embodiments, the tissue desired to be protected from radiation is bone marrow, skin, pulmonary tissue, thyroid tissue, gonadal tissue, tissue of the gastrointestinal tract, skeletal tissue, fetal tissue, or a combination thereof.

Identity of the Second Therapeutic Agent of the Radiotherapeutic Combination

The therapeutic method may be characterized according to the identity of the second therapeutic agent. For example, in certain embodiments, the second therapeutic agent comprises amifostine. In certain embodiments, the second therapeutic agent is amifostine or a pharmaceutically acceptable salt thereof. In certain embodiments, the second therapeutic agent is amifostine. In certain other embodiments, the second therapeutic agent (e.g., amifostine or a pharmaceutically acceptable salt thereof) is administered according to a pulse-dose regimen.

In certain other embodiments, the second therapeutic agent is a cytokine. In certain embodiments when the second therapeutic agent is a cytokine, the cytokine is interleukin 1, interleukin 2, interferon-gamma, granulocyte/macrophage colony-stimulating factor, granulocyte-colony-stimulating factor, or tumor necrosis factor alpha.

In certain other embodiments, the second therapeutic agent is an oncolytic virus. Exemplary oncolytic viruses contemplated for use in the therapeutic methods described herein include those described in U.S. Patent Application Publication 2011/0318311, which is hereby incorporated by reference. In certain embodiments, the second therapeutic agent is an oncolytic virus that expresses a cytokine, such as GM-CSF, an interleukin (e.g., IL-1, IL-2, IL-4, IL-12, IL-10, IL-19, or IL-20), or an interferon (e.g., interferon-alpha, interferon-beta, or interferon gamma).

In certain other embodiments, the second therapeutic agent is glutathione, N-acetylcysteine, iron, an iron salt, ferric oxide, a cobalt salt, a metal chelator agent, a fullerene, an agent that promotes DNA repair, a viral gene therapy that delivers Poly ADP ribose polymerase (PARP), an agent that inhibits p53 activity, and an anti-TNF alpha agent. In certain embodiments, the second therapeutic agent is glutathione, N-acetyl-cysteine, iron, an iron salt, ferric oxide, cobalt chloride, an agent that chelates iron, deferoxamine, an agent that chelates copper, an agent that chelates zinc, a fullerene, a polyamide, resveratrol, sodium orthovanadate, pifithrin-alpha, infliximab, etanercept, thalidomide, and pentoxifylline.

In certain embodiments, the second therapeutic agent is amifostine or a pharmaceutically acceptable salt thereof, and the method further comprises the step of administering to the patient an agent that increases the rate at which amifostine undergoes metabolism in the patient (e.g., an agent that increases the activity of alkaline phosphatase). An exemplary agent that increases the activity of alkaline phosphatase is prednisolone.

The therapeutic method may be characterized according to the dose of amifostine administered to the subject when the second therapeutic agent administered to the subject comprises amifostine. For example, in certain embodiments, the second therapeutic agent is administered at a dosage of from about 100 mg/m$^2$ to about 500 mg/m$^2$ amifostine on any day on which amifostine is administered to the subject. In certain embodiments, the second therapeutic agent is administered at a dosage of from about 150 mg/m$^2$ to about 250 mg/m$^2$ amifostine on any day on which amifostine is administered to the subject. In certain embodiments, the second therapeutic agent is administered at a dosage of about 200 mg/m$^2$ amifostine on any day on which amifostine is administered to the subject. In some embodiments, the dosage of amifostine that is necessary to produce a radioprotective effect can be decreased when administered in combination with RRx-001. Accordingly, administration of RRx-001 in combination with amifostine allows a lower dose of amifostine to be used for treatment, while maintaining the radioprotective effect. In some embodiments, the combination of RRx-001 with amifostine produces a greater radioprotective effect in a subject compared to either agent alone.

Subjects for Treatment

The therapeutic method may be further characterized according to the subject to be treated. In certain embodiments, the subject is a human. In certain embodiments, the subject is an adult human. In certain embodiments, the subject is an adult human at risk of exposure to radiation from a nuclear emergency. In certain other embodiments, the subject is a pediatric human. In certain other embodiments, the subject is an animal, such as a domesticated animal (e.g., a dog, a cat, or livestock).

In certain other embodiments, the subject is at risk of exposure to radiation from a nuclear emergency or from space travel. In certain embodiments, the subject is at risk of exposure to radiation from a nuclear emergency. In certain other embodiments, the subject is at risk of exposure to radiation from space travel. In certain other embodiments, the subject is an astronaut.

In certain other embodiments, the subject is at risk of radiation induce damage due radiation therapy for the treatment of a cancer.

In certain other embodiments, the subject has a suppressed immune system. In certain embodiments, the suppressed immune system is caused by an immunosuppressive medication. In certain embodiments, the immunosuppressive medication is a steroid, a calcineurin inhibitor, an interleukin-receptor-inhibiting antibody, or an interferon. In certain embodiments, the immunosuppressive medication is a steroid. In certain other embodiments, the suppressed immune system is caused by an immune deficiency syndrome (e.g., human immunodeficiency virus). In certain other embodiments, the subject having a suppressed immune system is a subject that has a history of hematopoietic stem cell transplantation in order to help ameliorate the symptoms of a suppressed immune system.

Administration of Additional Therapeutic Agents

In certain embodiments, the methods provided herein further comprise administering the radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine) in further combination with one or more additional therapeutic agents. In some embodiments, the one or more additional therapeutic agents is administered prior to, concurrently, or subsequent to administration of the therapeutic agent (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine).

Pain-Relieving Agent

In certain embodiments, the methods provided herein further comprise administering a radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine) in further combination with a pain-relieving agent. In some embodiments, the pain-relieving agent is administered prior to, concurrently, or subsequent to administration of the radiotherapeutic combination (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine). Exemplary pain relieving agents include a local analgesic, aspirin, a corticosteroid, and non-steroidal anti-inflammatory agent. In certain embodiments, the pain-relieving agent is aspirin, a corticosteroid, or a nonsteroidal anti-inflammatory agent.

In certain embodiments, the method further comprises, prior to administration of the radiotherapeutic combination, administering to the subject a local analgesic agent to tissue in proximity to the site of administration of the therapeutic agent. In certain embodiments, the local analgesic agent is a caine analgesic. In certain embodiments, the local analgesic agent comprises lidocaine. In certain embodiments, the local analgesic agent is lidocaine hydrochloride. In certain other embodiments, the local analgesic agent is VanPen cream. In certain other embodiments, the local analgesic agent is a NSAID. In certain other embodiments, the local analgesic agent is acetaminophen. In certain other embodiments, the local analgesic agent is VanPen cream, a NSAID, or acetaminophen.

In certain embodiments, the local analgesic agent is a formulation that comprises: i) a single active ingredient selected from the group consisting of lecithin, isopropyl palmitate, isopropyl myristate, and combinations thereof; and ii) excipients to form an ointment, cream, gel, lotion, spray, foam, paste, suspension or dispersion, for topical application to the skin. In certain embodiments, the single active ingredient is a combination of lecithin, isopropyl palmitate, and isopropyl myristate. In certain embodiments, formulation comprises soya lecithin, isopropyl palmitate, steric acid, glycerol, monostearate, isopropyl myristate, and polyoxyl 40 stearate.

In certain embodiments, the local analgesic agent is a formulation that consists of (i) lecithin and optionally one or two penetration enhancer fatty acid ester compounds, as the only active ingredients, and (ii) excipients to form an ointment, cream, gel, lotion, spray, foam, paste, suspension or dispersion for topical application to the skin of the subject. In certain embodiments, the formulation has one or two penetration enhancer fatty acid ester compounds.

In certain embodiments, the formulation has one penetration enhancer fatty acid ester compound selected from the group consisting of isopropyl palmitate and isopropyl laurate. In certain embodiments, the penetration enhancer fatty acid ester compound is isopropyl palmitate. In certain embodiments, one of the excipients is an emulsifier. In certain embodiments, the emulsifier is a poloxamer, polyoxyethylene alkyl ether, polyoxyethylene sorbitan fatty acid ester, or polyoxyethylene stearate. In certain embodiments, the emulsifier is a polyoxyethylene stearate. In certain embodiments, another one of the excipients is a surfactant selected from the group consisting of glycerin monostearate and glyceryl monooleate. In certain embodiments, the formulation is in the form of a gel.

Anticancer Agent

In certain embodiments, the methods further comprise administering an anticancer agent to the subject in combination with the radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine). In certain embodiments, the anticancer agent is a chemotherapeutic agent (also referred to as an anti-neoplastic agent or anti-proliferative agent). Exemplary chemotherapeutic agents include, but are not limited to, an alkylating agent, an antibiotic, an anti-metabolite, a detoxifying agent, an interferon, a polyclonal or monoclonal antibody, an EGFR inhibitor, a HER2 inhibitor, a histone deacetylase inhibitor, a hormone, a mitotic inhibitor, an MTOR inhibitor, a multi-kinase inhibitor, a serine/threonine kinase inhibitor, a tyrosine kinase inhibitors, a VEGF/VEGFR inhibitor, a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent known in the art.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine 131 tositumomab (Bexxar); alemtuzumab (Campath); ibritumomab (Zevalin; In-I11; Y-90 Zevalin); gemtuzumab (Mylotarg); eculizumab (Soliris); ordenosumab; ramucirumab (Cyramza) and olaratumab (Lartruvo).

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BMW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azdl 152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; ramucirumab (Cyramza) pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Clara vis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the additional therapeutic agent can be a cytokine such as G-CSF (granulocyte colony stimulating factor). In another aspect, a composition the present disclosure, or a pharmaceutically acceptable salt, prodrug, metabolite, analog or derivative thereof, may be administered in combination with radiation therapy. Radiation therapy can also be administered in combination with a composition of the present disclosure and another chemotherapeutic agent described herein as part of a multiple agent therapy. In yet another aspect, a composition of the present disclosure, or a pharmaceutically acceptable salt, prodrug, metabolite, mimetic, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azdl 152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

In particular embodiments, the methods further comprise administering an EGFR inhibitor to the subject in combination with a radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine). In certain embodiments, the EGFR inhibitor is erlotinib or a pharmaceutically acceptable salt thereof. In certain embodiments, the EGFR inhibitor is erlotinib hydrochloride. In certain embodiments, the EGFR inhibitor comprises erlotinib.

The therapeutic method may be characterized according to the dose of erlotinib administered to the subject. For example, in certain embodiments, a daily dose of at least 500 mg of erlotinib is administered to the subject on any day on which erlotinib is administered to the subject. In certain embodiments, a daily dose of at least 1000 mg of erlotinib is administered to the subject on any day on which erlotinib is administered to the subject. In certain embodiments, a daily dose of at least 2000 mg of erlotinib is administered to the subject on any day on which erlotinib is administered to the subject. In certain other embodiments, a daily dose in the range of about 1,000 mg to about 3,000 mg of erlotinib is administered to the subject on any day on which erlotinib is administered to the subject. In certain embodiments, a daily dose in the range of about 1,500 mg to about 2,500 mg of erlotinib is administered to the subject on any day on which erlotinib is administered to the subject. In certain embodiments, a daily dose in the range of about 1,800 mg to about 2,200 mg of erlotinib is administered to the subject on any day on which erlotinib is administered to the subject. In certain embodiments, a daily dose of about 2,000 mg of erlotinib is administered to the subject on any day on which erlotinib is administered to the subject.

Inorganic Nitrite Salt

In certain embodiments, the methods provided herein further comprise administering to the subject an inorganic nitrite salt in combination with a radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine). In certain embodiments, the inorganic nitrite salt is an alkali metal nitrite. In certain embodiments, the inorganic nitrite salt is sodium nitrite.

In certain embodiments, the inorganic nitrite salt is administered before administering the first therapeutic agent and/or second therapeutic agent of the radiotherapeutic combination to the subject, concurrently while administering the first therapeutic agent and/or second therapeutic agent of the radiotherapeutic combination to the subject, after administering the first therapeutic agent and/or second therapeutic agent of the radiotherapeutic combination to the subject, and/or each of the foregoing.

In certain embodiments, the inorganic nitrite salt is administered before the subject is exposed to radiation, concurrently while the subject is exposed to radiation, and/or after the subject has been exposed to radiation.

Treatment of Biological Material with the Therapeutic Agent

In certain embodiments, the methods comprise treatment of biological materials, such as isolated (e.g., blood cells), tissues, and organs, with a radiotherapeutic combination provided herein (e.g., a radiotherapeutic combination of (i) a first therapeutic agent selected from the group consisting of RRx-001 and a pharmaceutically acceptable salt thereof and (ii) a second therapeutic agent that reduces the effect of radiation on a subject, such as amifostine and/or a cytokine).

The method may be characterized according to the timing for exposing the biological material to the first therapeutic agent and the second therapeutic agent. For example, in certain embodiments, the biological material is exposed to at least one dose of the first therapeutic agent and at least one dose of the second therapeutic agent prior to exposure to the radiation. In certain embodiments, the biological material is exposed to at least one dose of the first therapeutic agent and at least one dose of the second therapeutic agent within 1 day prior to exposure to the radiation. In certain embodiments, the biological material is exposed to at least one dose of the first therapeutic agent and at least one dose of the second therapeutic agent within 12 hours prior to exposure to the radiation. In certain embodiments, the biological material is exposed to at least one dose of the first therapeutic agent and at least one dose of the second therapeutic agent within 6 hours prior to exposure to the radiation. In certain embodiments, the biological material is exposed to at least one dose of the first therapeutic agent and at least one dose of the second therapeutic agent within 3 hours prior to exposure to the radiation. In certain embodiments, the biological material is exposed to at least one dose of the first therapeutic agent and at least one dose of the second therapeutic agent within 2 hours prior to exposure to the radiation. In certain embodiments, the biological material is exposed to at least one dose of the first therapeutic agent and at least one dose of the second therapeutic agent within 1 hour prior to exposure to the radiation. In certain embodiments, the biological material is exposed to at least one dose of the first therapeutic agent and at least one dose of the second therapeutic agent within 30 minutes prior to exposure to the radiation. In certain embodiments, the biological material is exposed to at least one dose of the first therapeutic agent and at least one dose of the second therapeutic agent within 15 minutes prior to exposure to the radiation.

The method may be characterized according to the frequency of exposing the biological material to the first therapeutic agent and/or second therapeutic agent of the radiotherapeutic combination. For example, in certain embodiments, the biological material is exposed to the first therapeutic agent and/or second therapeutic agent of the radiotherapeutic combination no more frequently than once per week. In certain embodiments, the biological material is exposed to the first therapeutic agent and/or second therapeutic agent of the radiotherapeutic combination once per week for at least two weeks. In certain other embodiments, the biological material is exposed to the first therapeutic agent and/or second therapeutic agent of the radiotherapeutic combination at least once per week. In certain embodiments, the biological material is exposed to the first therapeutic agent and/or second therapeutic agent of the radiotherapeutic combination at least twice per week. In certain embodiments, the biological material is exposed to the first therapeutic agent and/or second therapeutic agent of the radiotherapeutic combination at least once per two days. In certain embodiments, the biological material is exposed to the first therapeutic agent and/or second therapeutic agent of the radiotherapeutic combination at least once per day. In certain embodiments, the biological material is exposed to the first therapeutic agent and/or second therapeutic agent of the radiotherapeutic combination at least twice per day.

In certain embodiments, the method further comprises exposing the biological material to an inorganic nitrite salt. In certain embodiments, the inorganic nitrite salt is an alkali metal nitrite. In certain embodiments, the inorganic nitrite salt is sodium nitrite. In certain embodiments, the inorganic nitrite salt is administered before administering the first therapeutic agent and/or second therapeutic agent of the radiotherapeutic combination, concurrently while administering the first therapeutic agent, after administering the first therapeutic agent and/or second therapeutic agent of the radiotherapeutic combination, and/or each of the foregoing.

In certain embodiments, the inorganic nitrite salt is administered before the biological material is exposed to radiation, concurrently while the biological material is exposed to radiation, and/or after the biological material has been exposed to radiation.

Pharmaceutical Compositions

As indicated above, the present disclosure provides pharmaceutical compositions, which comprise an amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present disclosure which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present disclosure comprises an excipient selected from the group consisting of cyclodextrins, celluloses, liposomes, micelle forming agents, e.g., bile acids, and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose.

In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried.

They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (I particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this disclosure suitable for parenteral administration comprise one or more compounds of the disclosure in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present disclosure are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present disclosure may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg.

When the compounds described herein are co-administered with another agent (e.g., an additional radioprotective agent), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

Kits for Use in Protecting Against and Reducing Effects of Radiation

Another aspect of the disclosure provides a kit for protecting against or reducing the effects of radiation. The kit comprises (i) a therapeutic agent selected from the group consisting of RRx-001 or a pharmaceutically acceptable salt thereof and (ii) instructions for protecting against, or reducing the effects of, radiation according to procedures described herein. In certain embodiments, the kit further comprises (iii) a local analgesic agent, such as lidocaine hydrochloride.

EXAMPLES

Example 1—Effect of RRx-001 on Survival Following Lethal Irradiation

In this Example, the effects of systemic administration of RRx-001 on survival in response to a lethal dose of radiation was assayed in mice. CD2F1 male mice 9.5-11 weeks old were administered a single dose of RRx-001 by intraperitoneal (IP) injection 24 hours prior to a lethal radiation dose. 24 mice received 10 mg/kg RRx-001 (formulated in 5% DMSO in sterile $H_2O$) and 24 mice received the vehicle control (5% DMSO in sterile $H_2O$ only).

The mice were subjected to total body irradiation (TBI) with 9.35 Gy (LD70/30) at 0.6 Gy/min using High-level Cobalt-60. Unanesthetized mice were placed in well-ventilated Plexiglas restrainers and irradiated bilaterally. Sham-irradiated mice were also placed in identical Plexiglas restrainers and kept in a room shielded from irradiation at the same time. In each experiment, the dose to the abdominal cores of the animals was delivered at a dose rate of approximately 0.6 Gy/min. Dosimetry was performed prior to the irradiation of the animals using the highly accurate alanine/electron spin resonance (ESR) dosimetry system (American Society for Testing and Materials, Standard E 1607) to measure dose rates (to water) in the cores of acrylic mouse phantoms, which were located in the compartments of the exposure rack. A calibration curve based on standard alanine calibration dosimeters provided by the National Institute of Standards and Technology (NIST, Gaithersburg, Md.) was used to measure the doses. The accuracy of the dose rate calibrations has been verified several times using the services of the National Physics Laboratory (UK National Standards Laboratory, London, UK) and the M. D. Anderson Cancer Center (Houston, Tex.). The corrections applied to the measured dose rates in the phantoms were for a small difference in the Co-60 energy between the mass energy-absorption coefficients for soft tissue and water, as well as source decay. The radiation field was uniform within ±1.2%.

Mice were monitored at least twice a day for 30 days post-irradiation. During the critical period (days 10-20), mice were monitored at least three times a day with no more than 10 hours between observations. Mice displaying any signs of discomfort received food in their cage as a wet mash. Mice displaying overt dyspnea, weight loss, lethargy, or other markers of moribundity and appearing to be in distress were humanely euthanized in a separate room using carbon dioxide gas followed by cervical dislocation after breathing stopped as a confirmatory method of euthanasia. This experiment was repeated for a total of n=24 mice per group.

Survival curves were estimated using the Kaplan-Meier method and were compared using a two-sided log-rank test at the 0.05 significance level. P-values were considered statistically significant if less than 0.05.

Survival improvement in favor of pretreatment with one dose of 10 mg/kg RRx-001 over vehicle control irradiated mice was highly significant with an approximate 33.4% reduction in the 30-day death risk (FIG. 1A). Time to death data depicting the 30-day survival is shown in FIG. 1B. A scatterplot of the survival times by treatment group show the means±standard errors are 20.2±1.6 and 27.2±1.1 for vehicle and RRx-001 groups, respectively. Therefore, 10 mg/kg RRx-001 administered 24 hours prior to a lethal TBI dose not only significantly increases survival by 33.4% but also significantly increases the mean survival time by 7 days compared to the vehicle control.

Example 2—Effect of RRx-001 on Hematopoietic Recovery Following Irradiation

To determine the pathophysiological effects of RRx-001 on hematopoietic protection in mice, CD2F1 male mice were treated with 10 mg/kg RRx-001 or the vehicle control 24 hours prior to a sublethal dose of TBI (7 Gy at 0.6 Gy/min using High-level Cobalt-60) or sham irradiation (day 0) according to the table below.

CD2F1 male mice (n=3/group) were divided into 4 experimental groups: 1) irradiation+vehicle, 2) irradiation+RRx-001, 3) sham-irradiation+vehicle and 4) sham-irradiation+RRx-001. Either 10 mg/kg RRx-001 or the vehicle control were IP injected 24 hours prior to either irradiation or sham-irradiation (day 0). On days 2, 7, 14, 21, and 28 post-irradiation (day 0) mice were humanely euthanized. Blood, bone marrow, and sternebrae were then collected. This experiment was performed in duplicate for a total of n=6 mice/group/time point.

Post-irradiation whole blood was obtained by terminal cardiocentesis. Blood samples were immediately transferred into EDTA tubes (Sarstedt Inc., Newton, N.C.) and gently rotated until the time of analysis. The tubes were analyzed for a complete blood count with differential and reticulocytes using the ADVIA 2120 (Siemens Medical Solutions Diagnostics, Dublin, Ireland), and Microsoft software version 5.9 (Microsoft Corp., Redmond, Wash.) to generate the data.

Sternebrae from euthanized mice (n=6/group/time point) were collected on days 2, 7, 14, 21 and 28 post-irradiation. Sternebrae were fixed in 10% zinc-buffered formalin for at least 24 hours and up to 7 days. Fixed sternebrae were decalcified for 3 hr in 12-18% sodium EDTA (pH 7.4-7.5) and specimens dehydrated using graded ethanol concentrations and embedded in paraffin. Longitudinal 4 µm sections were stained with regular hematoxylin and eosin. Two board-certified pathologist conducted histopathological evaluation of the samples. One of the pathologist scored all the samples blindly. Bone marrow was evaluated in situ within sternebrae and graded (Grade 1: <10%; Grade 2: 11-30%; Grade 3: 31-60%; Grade 4: 61-89%; Grade 5: >90%) for total cellularity. Megakaryocytes were also quantified based on the average per 10 high power fields (HPF) at 400× magnification using a BX43 or BX53 microscope (Olympus, Minneapolis, Minn.). Images were captured with an Olympus DP22 camera and imported into Olympus Cellsens Standard software for review.

Blood parameters were compared between treatment groups using an analysis of variance (ANOVA). The Wilcoxon test was also used for sensitivity and to potentially address data departures from normality. A longitudinal mixed model repeated measures was also implemented to provide a more complete data analysis of the sham-irradiated treatment groups' difference in overall time profile mean based on the blood parameters. Bone marrow data (megakaryocytes and grade) statistical analysis was carried out using a parametric test consisting of a general linear model analysis of variance (ANOVA with factors consisting of treatment group and pathologist) and the Kruskal-Wallis nonparametric test. The statistical data analysis was carried out using R software (Version 3.4.3, 2016) and the graphs made using GraphPad Prism version 7.03 (GraphPad Software, La Jolla, Calif.).

To determine the effect of RRx-001 on bone marrow, a histopathological analysis of bone marrow sternebrae was performed and the cellularity, as reported by grade (grade 1:

| Group | Treatment | 2 days | 7 days | 14 days | 21 days | 28 days | Total mice |
|---|---|---|---|---|---|---|---|
| Vehicle Control | Sham + vehicle | 6 | 6 | 6 | 6 | 6 | 30 |
| Radiation Control | TBI + vehicle | 6 | 6 | 6 | 6 | 6 | 30 |
| Treatment Control | Sham + RRx-001 | 6 | 6 | 6 | 6 | 6 | 30 |
| Radiation Experimental | TBI + RRx-001 | 6 | 6 | 6 | 6 | 6 | 30 |

≤10%; grade 2: 11-30%; grade 3: 31-60%; grade 4: 61-89%; grade 5: ≥90% cellularity), and megakaryocyte numbers (averaged per 10 high-powered fields; HPF) were ascertained by two pathologists, one of which scored all the samples blindly (TAS, WEC). In determining significance for grade of cellularity and average number of megakaryocytes per 10 HPF, the differences between pathologists and the interaction between treatment and pathologist were not significantly different.

Figure 2:
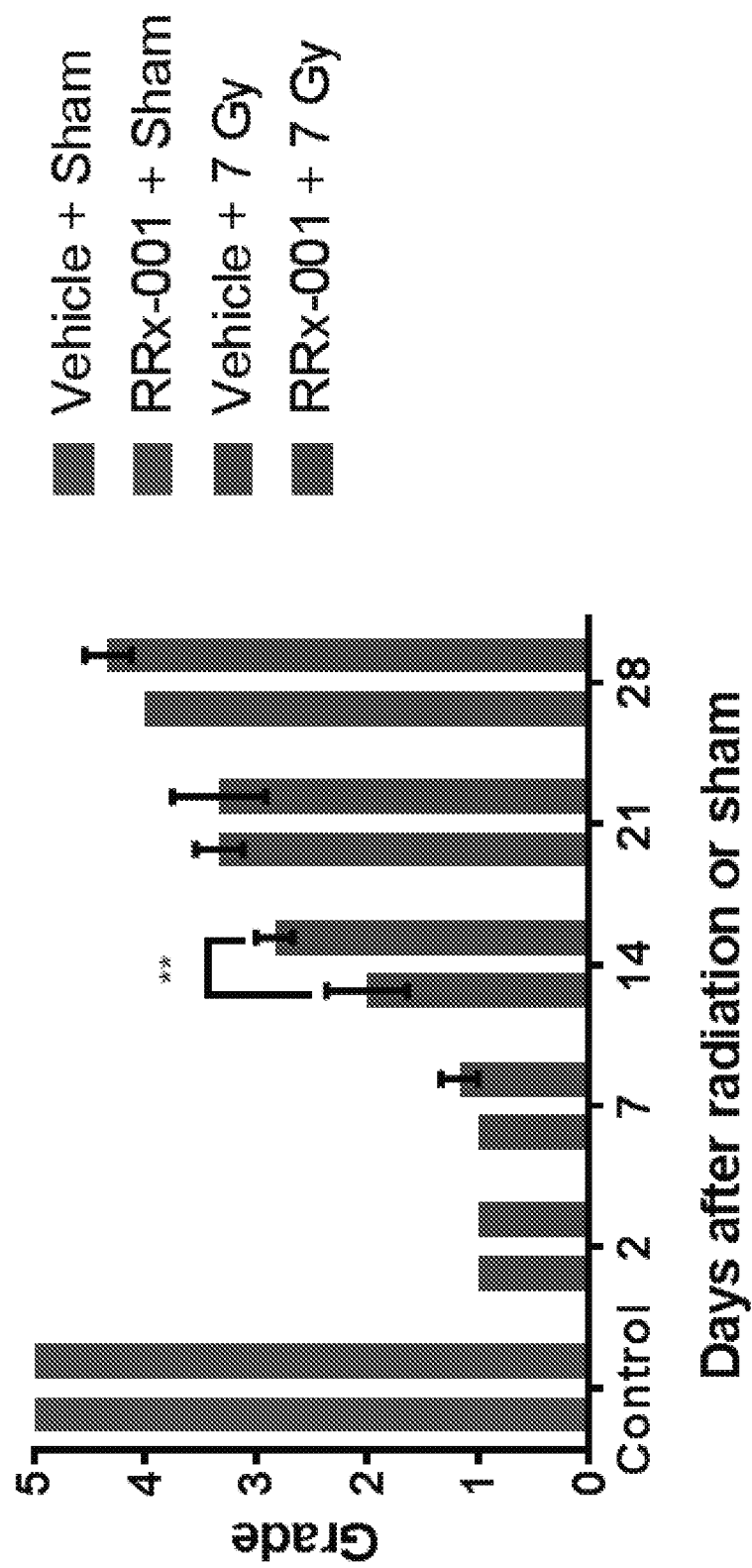
FIG. 2 illustrates the effects of RRx-001 treatment on bone marrow recovery following sublethal dose of TBI (7 Gy at 0.6 Gy/min) compared to an irradiated vehicle control. Sham=No radiation control. N=6/group/day; **p<0.005; Error bars are mean±SEM.
Figure 5:
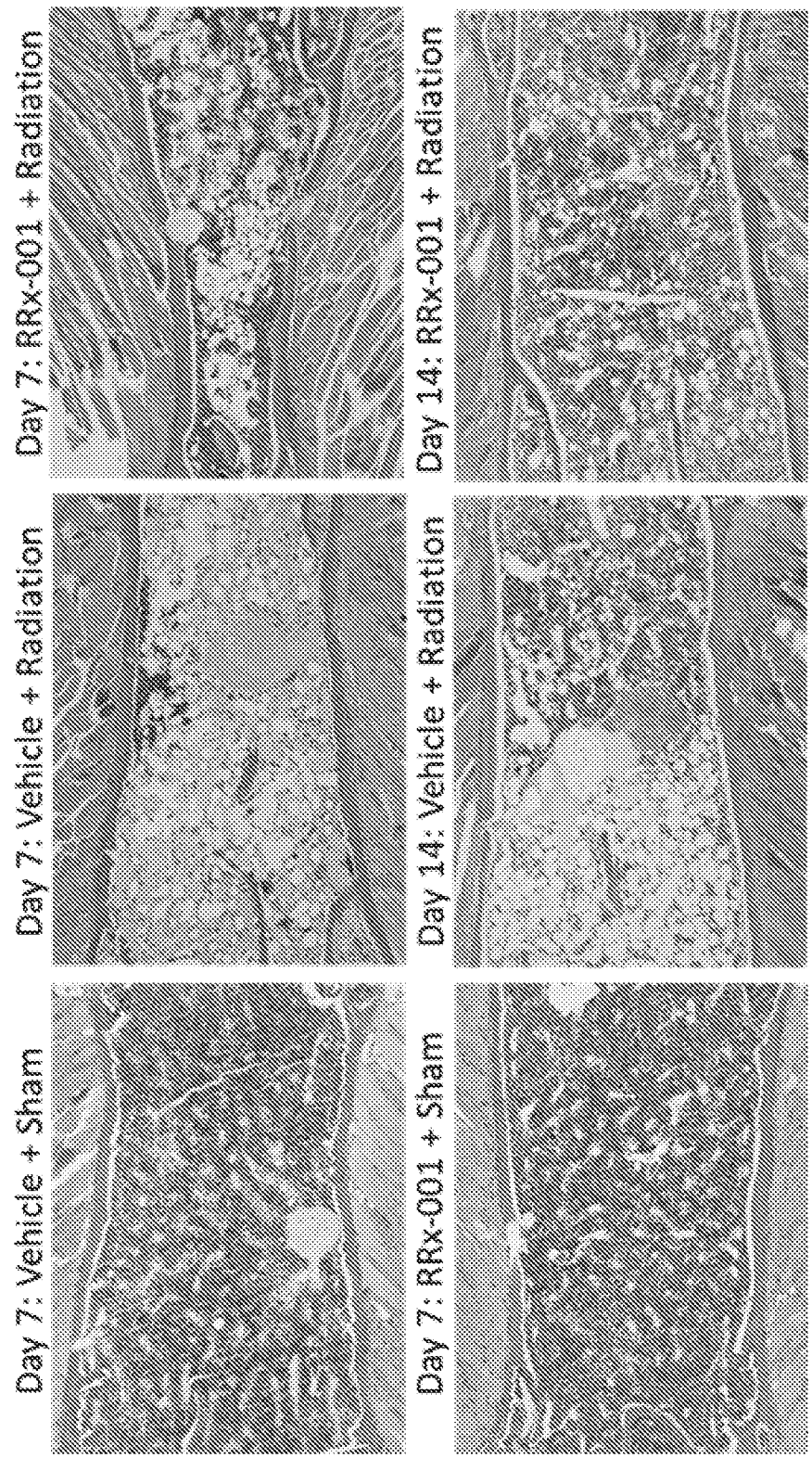
FIG. 5 shows representative sternal bone marrow photomicrographs illustrating increased bone marrow recovery on days 7 and 14 in the RRx-001+radiation group versus an irradiated vehicle control. All slides were stained with hematoxylin and eosin (H&E). Dark gray stain (center strip) is bone marrow (center gray horizontal strip), white is fat cells and light gray stain (top and bottom horizontal strips) is muscle.

The overall cellularity of the bone marrow in both the sham-irradiated RRx-001- and vehicle-treated groups never dropped below 90% during the duration of the study and therefore maintained a grade of 5 (FIG. 2). FIG. 3A-B show representative normal bone marrow morphology and cellularity. As expected after irradiation, both the RRx-001- and vehicle-treated groups had a massive loss in bone marrow cellularity (grade 1). By day 7 a slight increase in cellularity was observed by the pathologists in the RRx-001-treated mice compared to the vehicle control. As shown in FIG. 2, pretreatment with RRx-001 significantly accelerated hematopoietic recovery as determined by the grade of bone marrow cellularity compared with control on day 14. The irradiated vehicle-treated group showed a significant loss of bone marrow cellularity with an increase in infiltration by adipocytes compared to the irradiated RRx-001-treated group on day 14 where significant recovery of bone marrow cellularity was observed (FIG. 5).

Figure 3:
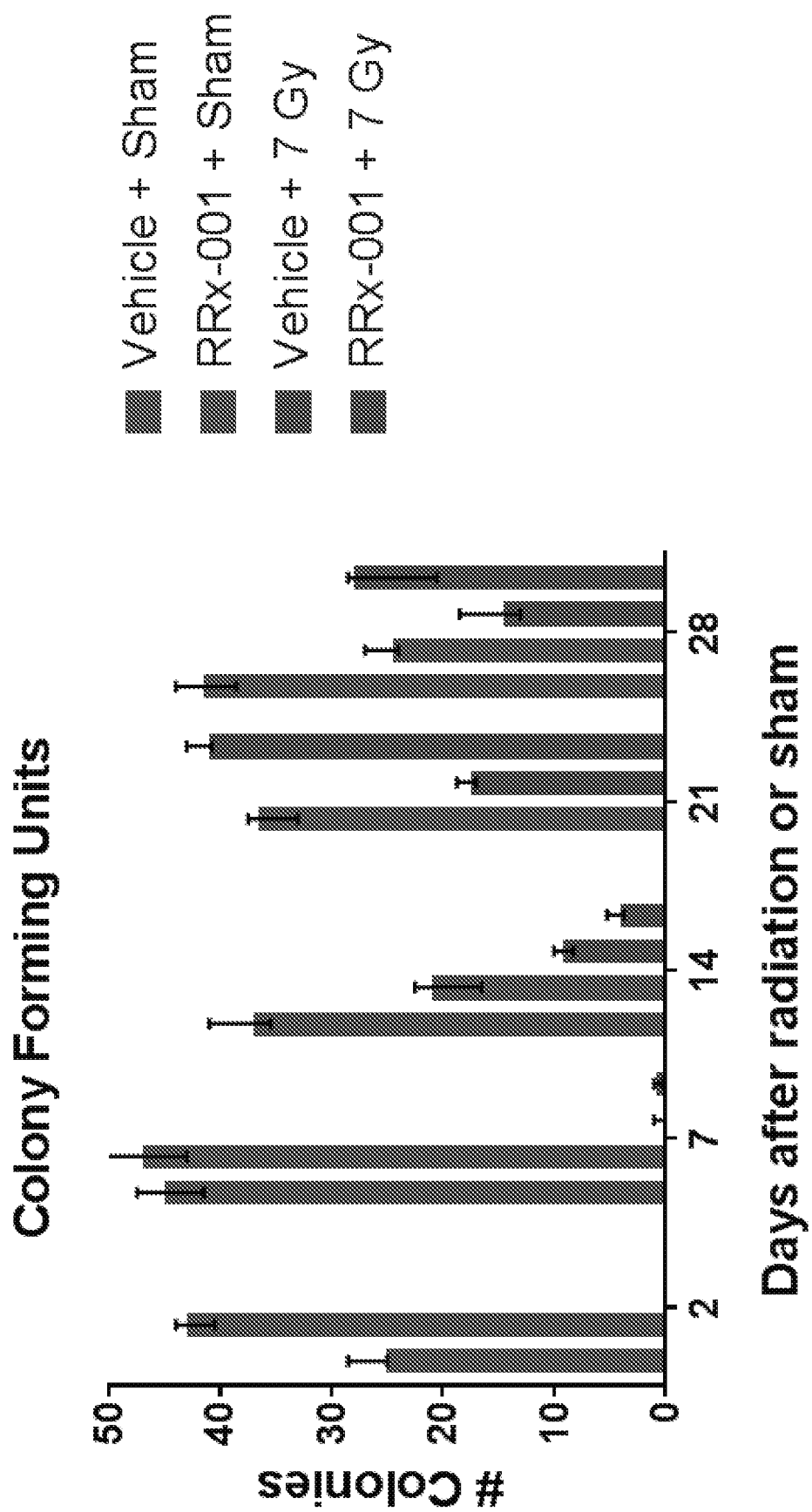
FIG. 3 illustrates the effects of RRx-001 treatment on the number of colony forming units produced from mouse bone marrow following sublethal dose of TBI (7 Gy at 0.6 Gy/min) compared to an irradiated vehicle control. 3 mice/group/day were combined into one sample and plated in triplicate.

The number of megakaryocytes in the sham-irradiated RRx-001 group was significantly higher than the vehicle control on day 14 (FIG. 3). In both of the irradiated groups, the number of megakaryocytes was reduced on day 2 and severely depleted by day 7. The irradiated RRx-001 group shows a steady increase in the number of megakaryocytes between days 7-28. Interestingly, the irradiated vehicle-treated group had a significant jump in the number of megakaryocytes between days 14-21 before decreasing to return to the same megakaryocyte numbers as the irradiated RRx-001-treated group on day 28 (FIG. 3).

Figure 4:
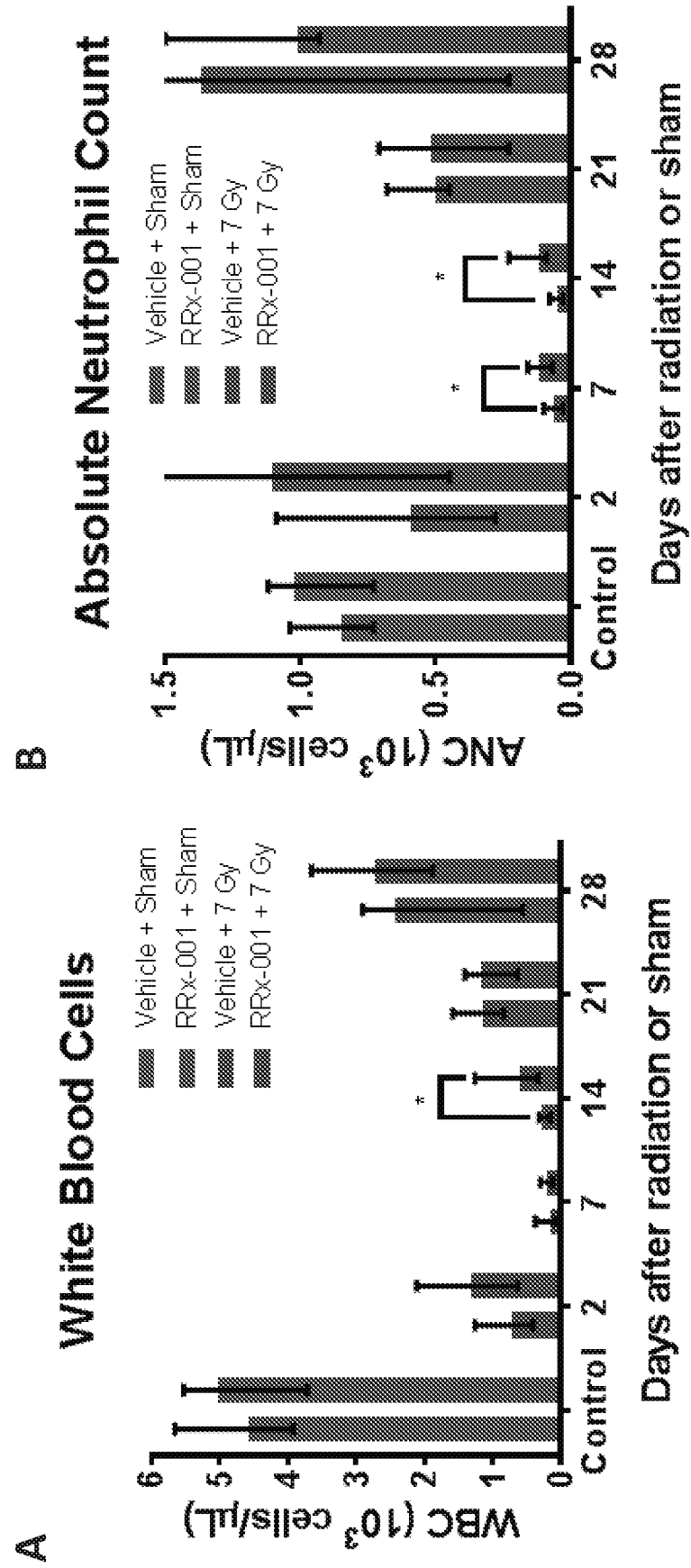
FIG. 4 illustrates the radioprotective effects of RRx-001 treatment on blood cell production following sublethal dose of TBI (7 Gy at 0.6 Gy/min) compared to an irradiated vehicle control. Data is presented for white blood cell count (FIG. 4A), absolute neutrophil count (FIG. 4B), lymphocyte count (FIG. 4C), monocyte count (FIG. 4D), reticulocyte count (FIG. 4E), and % hematocrit (percentage by volume of red cells to the volume of whole blood) (FIG. 4F). N=4-6 mice/group/day; *p<0.05; Error bars are median with 95% CI.
Figure 4:
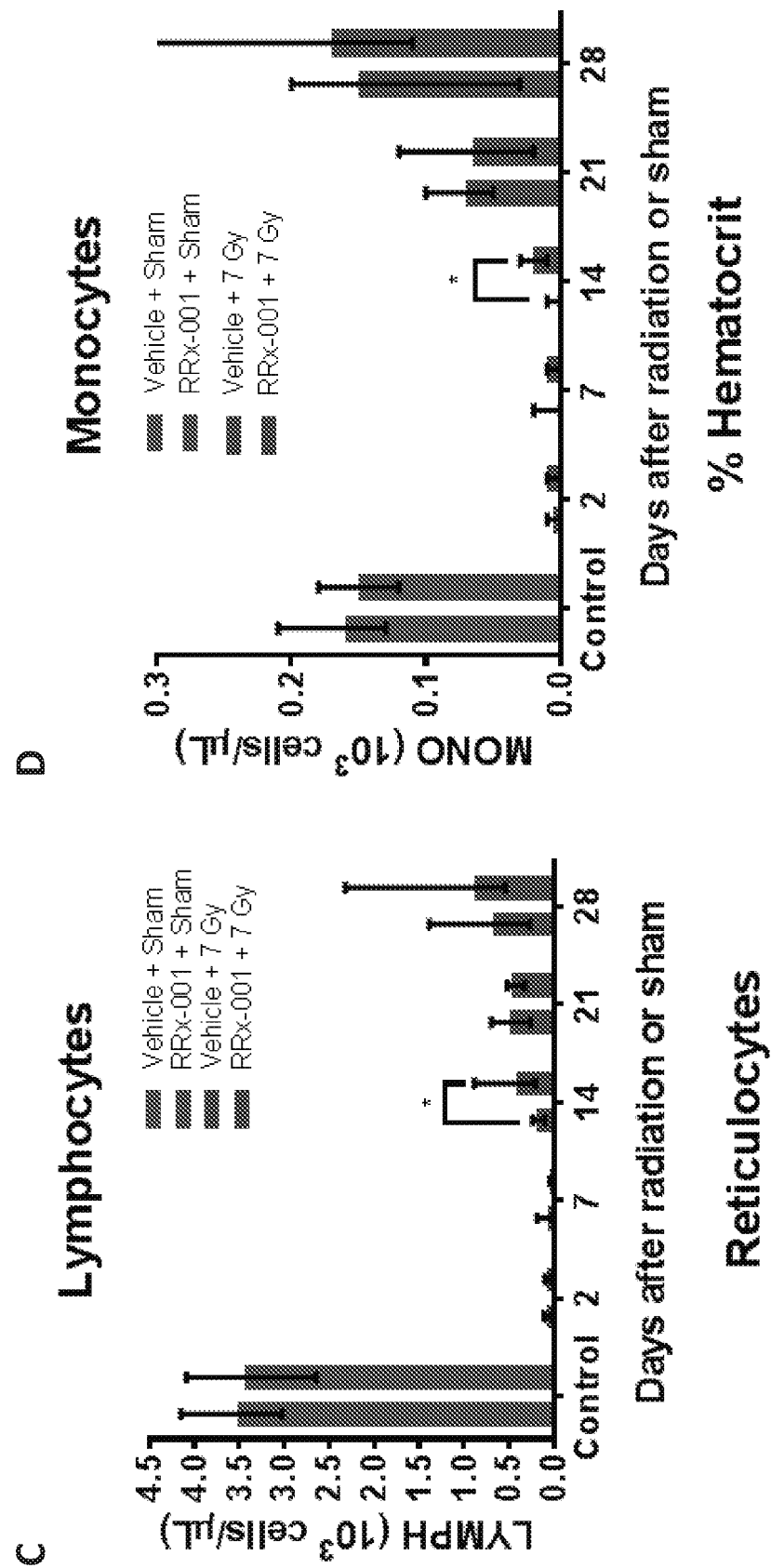
Figure 4:
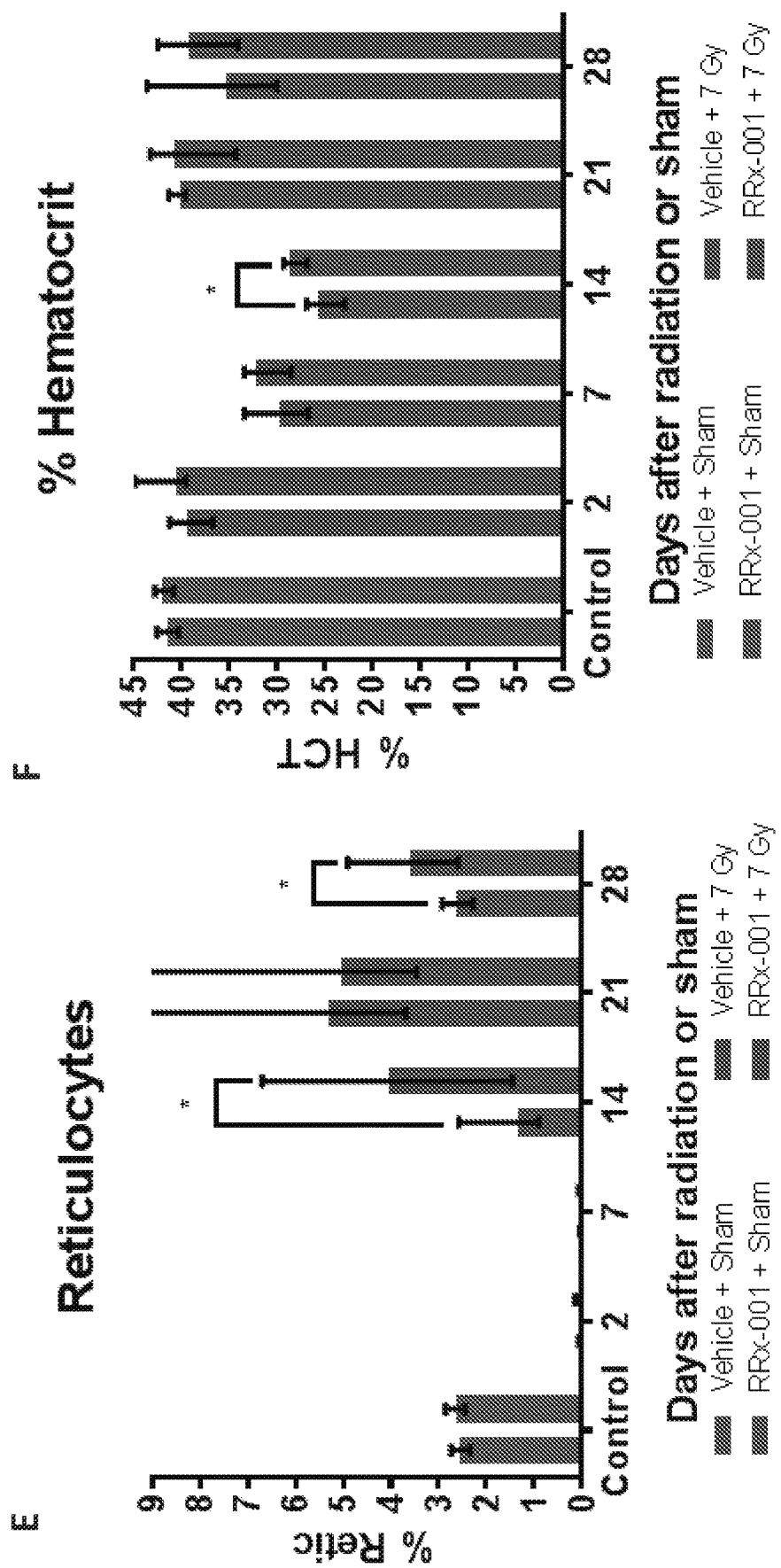

RRx-001 treatment also produced a significant increase in white blood cells and red blood cell production in the irradiated mice compared to the irradiated vehicle control (FIG. 4). A longitudinal mixed model repeated measures analysis comparing the difference in the overall mean of platelets over time revealed a statistically significant difference in the least-square means in favor of RRx-001-treatment ($p=0.01$). The standard error of mean for the sham-irradiated RRx-001-treated versus vehicle-treated platelets were 1067.73 (32.26) and 913.66 (52.22), respectively. No significant difference in white blood cells (WBC), absolute neutrophil count (ANC), absolute lymphocyte count (ALC), platelets (PLT), percent hematocrit (% HCT) and percent reticulocytes (% RETIC) for days 2 and 21 post-irradiation was observed when comparing RRx-001-treated mice to the vehicle control (FIG. 4). Both irradiated RRx-001-treated and vehicle-treated groups showed a decrease in red blood cells and hemoglobin below the sham-irradiated controls on days 7 and 14 before returning to control levels; however, the irradiated groups were not significantly different when compared to each other.

In both experimental groups, the treatment with sublethal doses of acute irradiation induced severe reticulocytopenia and leukopenia. Reticulocytopenia persisted up to day 7 after irradiation. By day 14 after irradiation, % RETIC in RRx-001 pretreated mice was significantly increased and returned to baseline levels compared to control mice. Though both irradiated groups returned or were higher than baseline levels by day 28, RRx-001-treated mice still had significantly increased % RETIC compared to the vehicle controls. WBC and ALC reached their nadir on day 7 in both irradiated groups; however by day 14, WBC and ALC counts were also significantly increased in the RRx-001-treated mice compared to the controls. In both the irradiated RRx-001- and control-treated mice, the ANC and PLT reached their lowest point on day 7 and stayed there through day 14. However, for both the ANC and PLT, the irradiated mice pretreated with RRx-001 were significantly increased on both days 7 and 14 when compared to the control. Although % HCT reached its nadir on day 14, the irradiated RRx-001 mice had significantly increased levels on day 14 compared to the irradiated control.

The blood work and bone marrow obtained from the sublethal irradiation study show a significant increase in bone marrow cellularity and white and red blood cell production on day 14 in the RRx-001 irradiated group compared to the irradiated vehicle control. This may provide enough protection to allow for recovery during this crucial time period when infection and sepsis can occur. Taken together, these experiments demonstrate that systemic administration of RRx-001 prior to total body irradiation significantly improves overall survival and bone marrow regeneration.

Example 3—Characterization of the Radioprotective Effects of RRx-001

Figure 7:
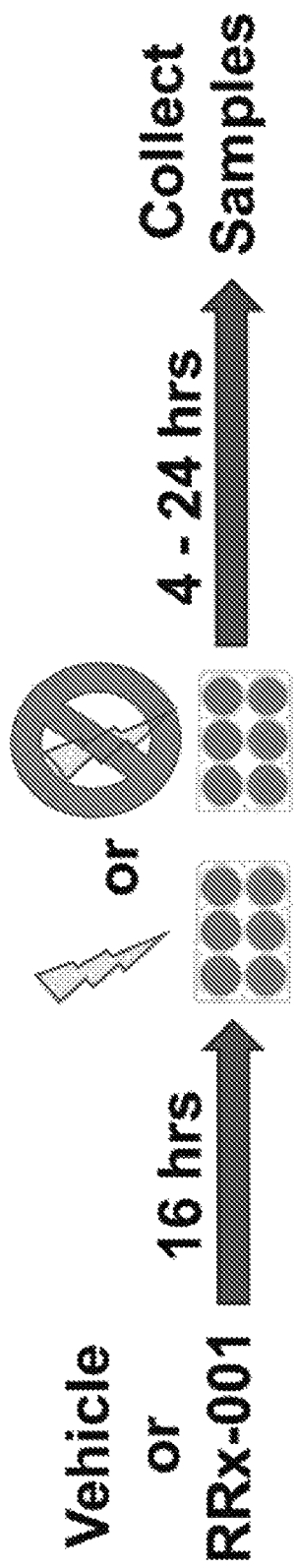
FIG. 7 illustrates an in vitro model experimental design for characterizing the radioprotective effects of RRx-001.

Antioxidant response element (ARE) genes such as heme oxygenase 1 (HO-1), NAD(P)H Dehydrogenase [Quinone] 1 (NQO-1) and Superoxide Dismutase (SOD) are involved in the detoxification and elimination of reactive oxidants. This example was designed to show that in vitro treatment with RRx-001 induces mild oxidative stress which increases Antioxidant Response Element (ARE) proteins in human normal bone marrow mesenchymal stem cells (hMSC), macrophages and their precursor monocyte cells. An exemplary treatment scheme is provided in FIG. 7.

Expression of ARE proteins was assayed in hMSC, macrophages, and monocytes following in vitro irradiation of the cells, which were pretreated with RRx-001 or vehicle. Protein expression was assayed by Western blotting and protein quantification.

hMSC were treated for 16 hours with 5 mM RRx-001 or the vehicle control (0.05% DMSO), irradiated at 10 Gy or sham-irradiated and the protein collected 8 or 24 hours post-sham or irradiation. Human monocytic leukemic THP-1 and U937 cells were differentiated into macrophages with 50 nM Phorbol 12-myristate 13-acetate (PMA) for 24 hours before treatment. Differentiated and non-differentiated cells were treated with 3 mM RRx-001 or 0.05% DMSO (vehicle control) for 16 hours prior to radiation. The cells were irradiated at 5 Gy or sham-irradiated and collected 4-8 hours later for both analysis. For each experiment, duplicates of each sample were run.

The activity of superoxide dismutase activity was also assayed in hMSC. hMSC were treated for 16 hours with 5 mM RRx-001 or vehicle, irradiated at 10 Gy or sham-irradiated and whole cell homogenate collected according to the manufacture's protocol. The assay measures the activity of all three forms of SOD. The amount of SOD activity (U/mL) was normalized to protein levels.

Figure 8:
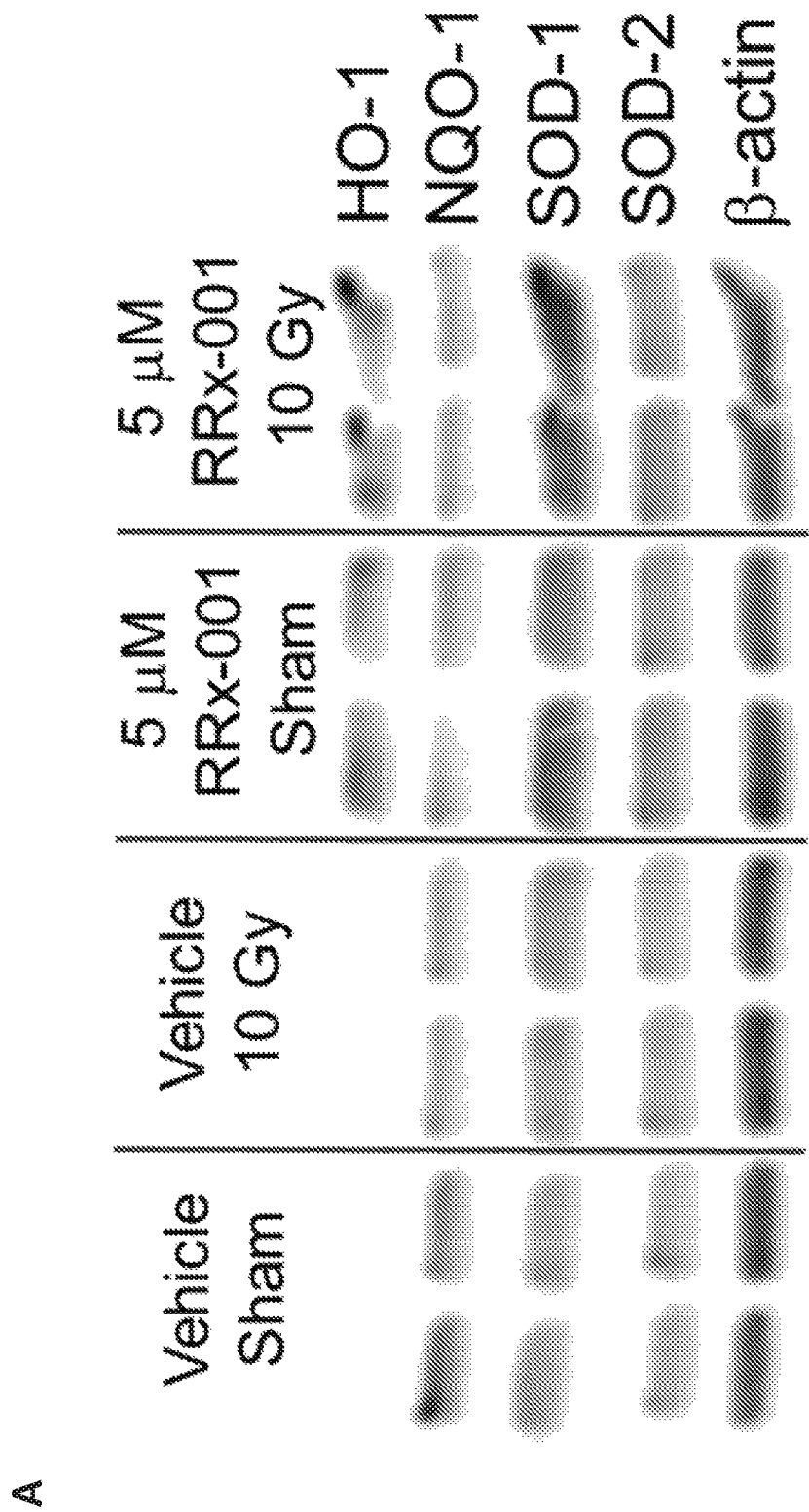
FIG. 8 illustrates Western blotting (FIG. 8A) and quantification of protein expression (FIGS. 8B-8E) of genes having antioxidant response elements (ARE) following irradiation of human mesenchymal stem cells treated with RRx-001 or a vehicle control. Data is shown for Heme oxengenase-1 (HO-1) (FIG. 8B), quinine oxidoreductase-1 (NQO-1) (FIG. 8C), superoxide dismutase-1 (SOD-1) (FIG. 8D), and superoxide dismutase-2 (SOD-2) (FIG. 8E). Beta-actin expression was employed as a control.
Figure 8:
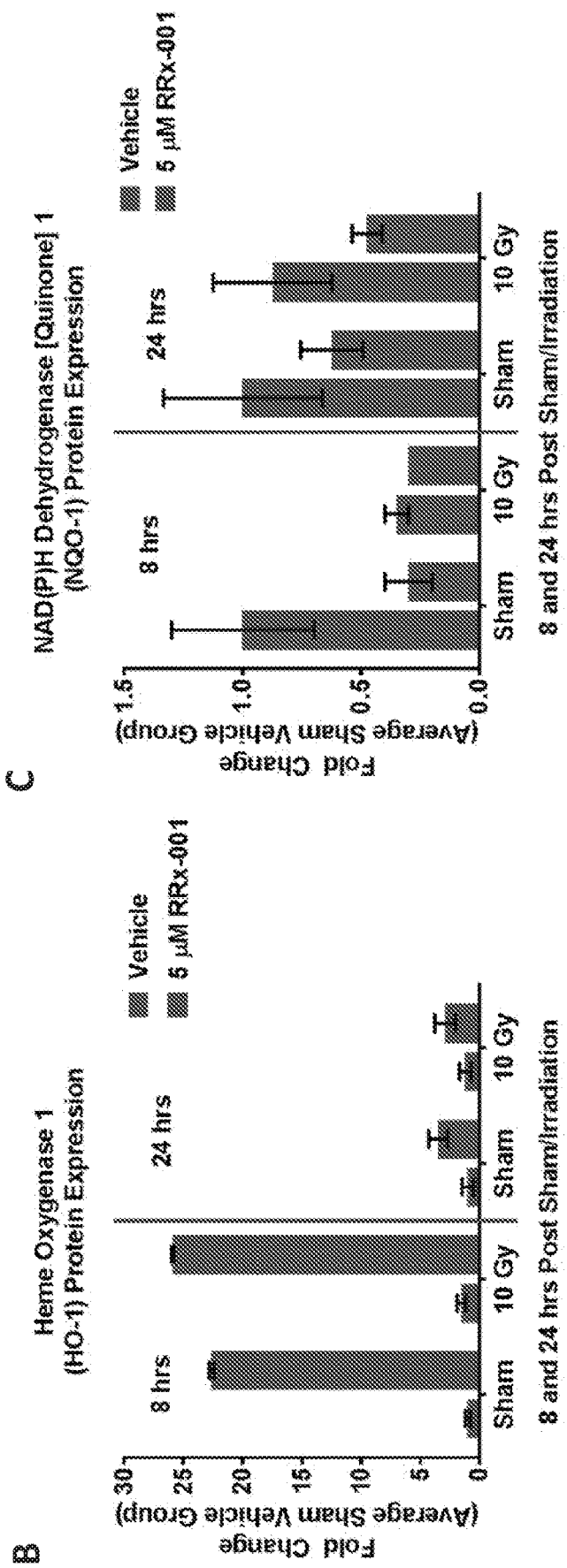
Figure 8:
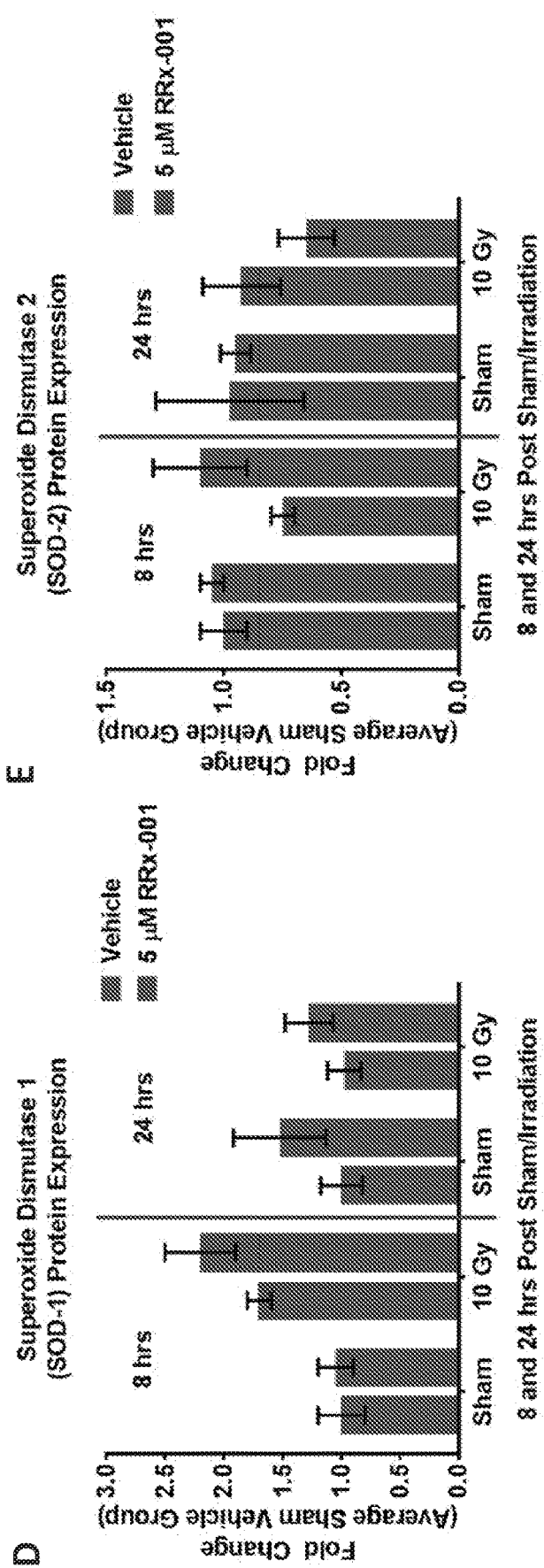
Figure 9:
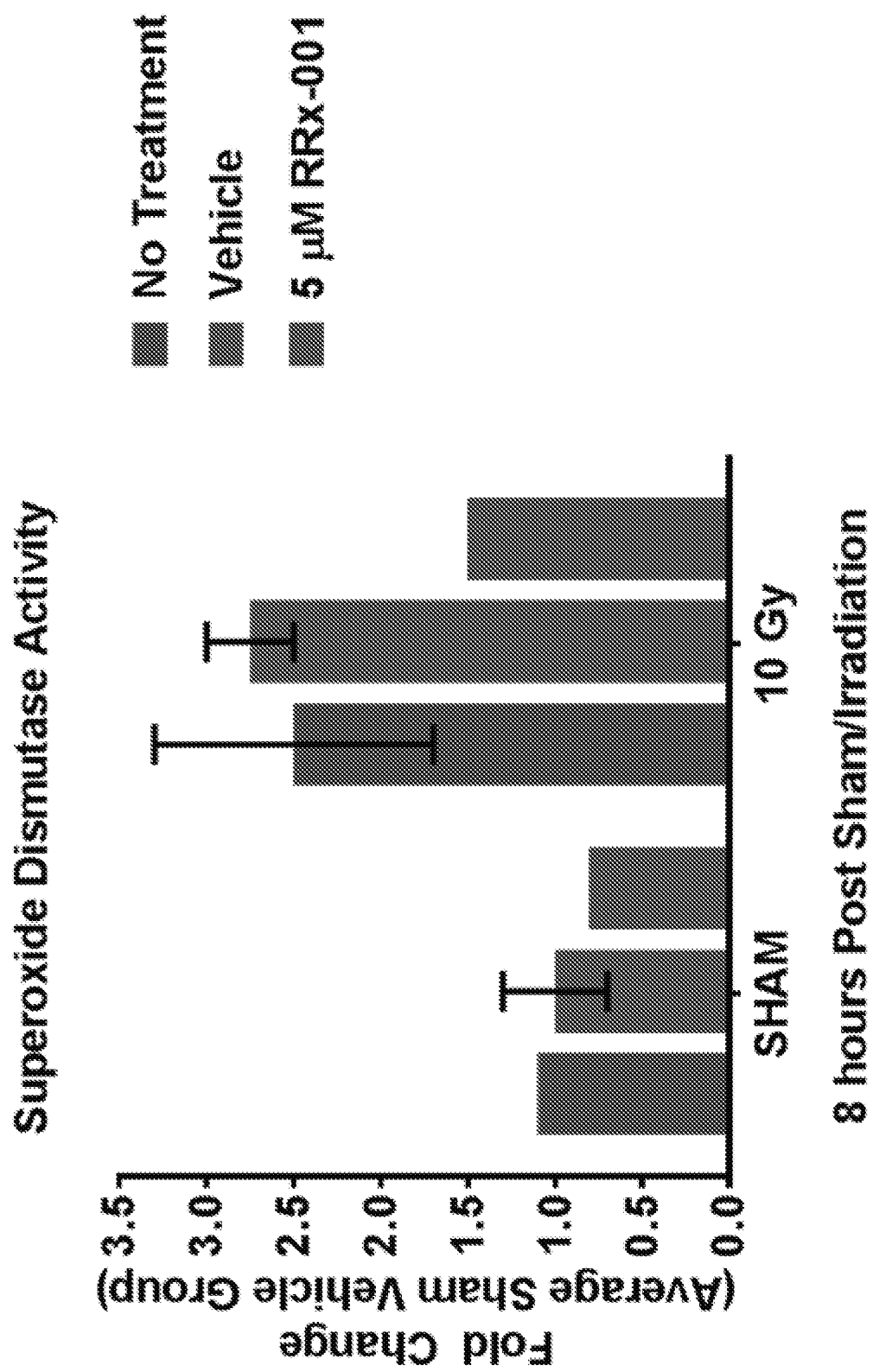
FIG. 9 illustrates the effects of RRx-001 on superoxide dismutase activity in irradiated human mesenchymal stem cells compared to a vehicle control.

At 8 hours post-sham or irradiation, RRx-001 showed a significant increase in HO-1 expression (22-26 fold) in both the sham and irradiated hMSC groups (FIG. 8). At 24 hours, the RRx-001-treated groups still had an increase in HO-1 expression; however the increase dropped to 2-3.5 fold. RRx-001 treatment slightly reduced NQO-1 in all groups. SOD1 and 2 showed a slight increase at 8 hours after RRx-001 treatment and 10 Gy irradiation. Superoxide Dismutase Activity did not increase 8 hours after 10 Gy irradiation in the RRx-001 treated group (FIG. 9).

Figure 10:
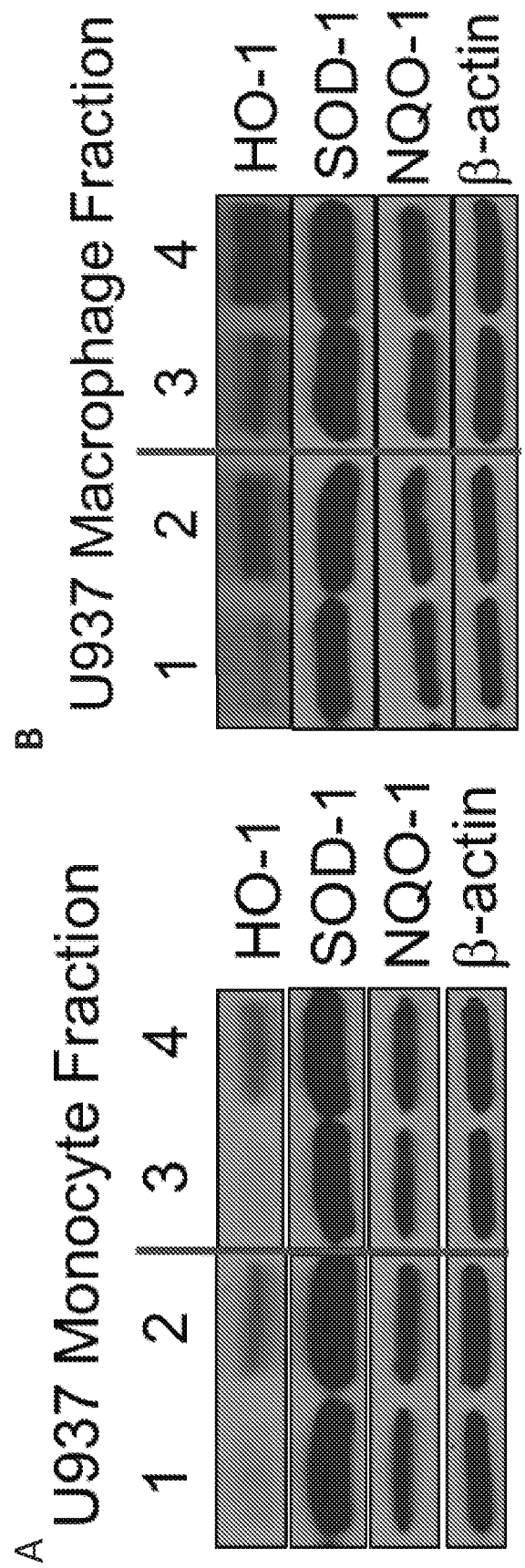
FIGS. 10A and 10B illustrate Western blots showing protein expression of HO-1, NQO-1, and SOD-1 in U937 monocyte fractions (FIG. 10A) and U937 macrophage fractions (FIG. 10B) 4 hours post-irradiation. Lane 1: vehicle/no irradiation; lane 2: vehicle/10 Gy irradiation; lane 3: RRx-001 (3 μM)/no irradiation; lane 4: RRx-001 (3 μM)/5 Gy irradiation.
FIGS. 10C-H illustrate quantification of protein expression for each gene (HO-1, NQO-1, and SOD-1) expressed as fold change relative to the vehicle/no irradiation control U937 monocyte fractions and U937 macrophage fractions.
Figure 10:
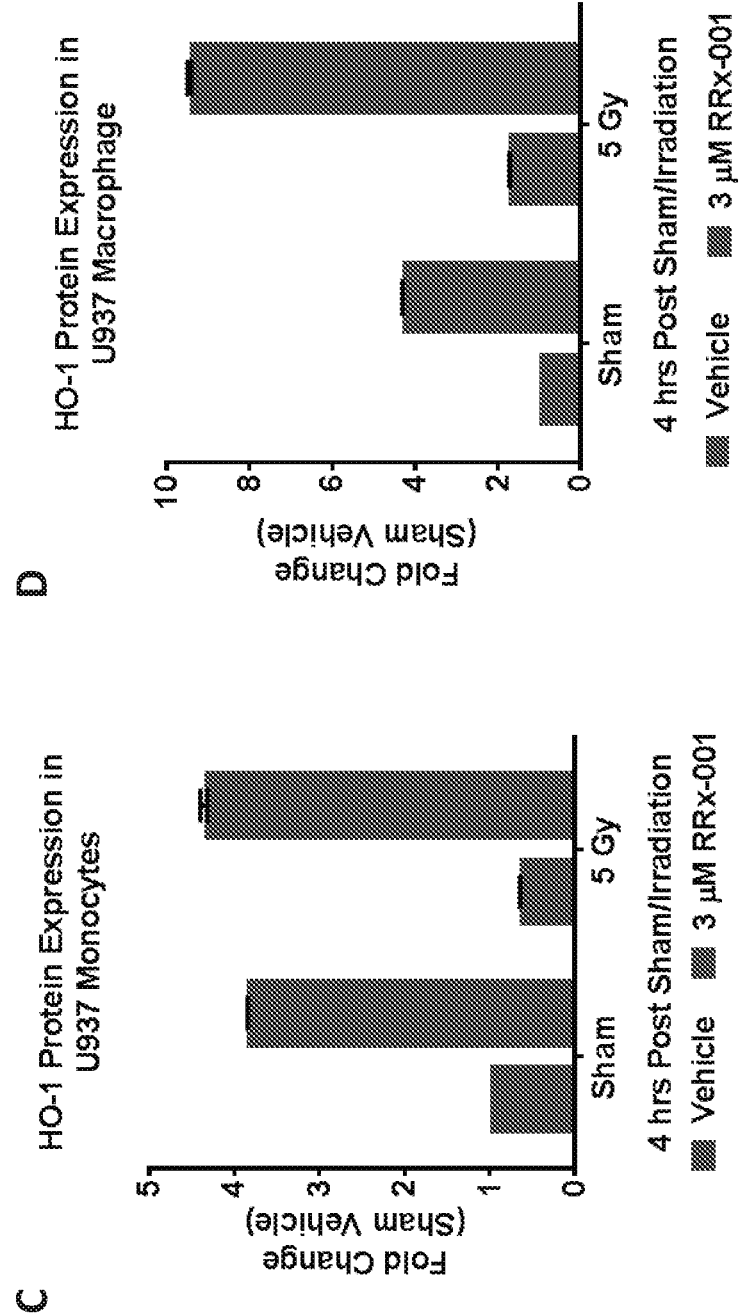
Figure 10:
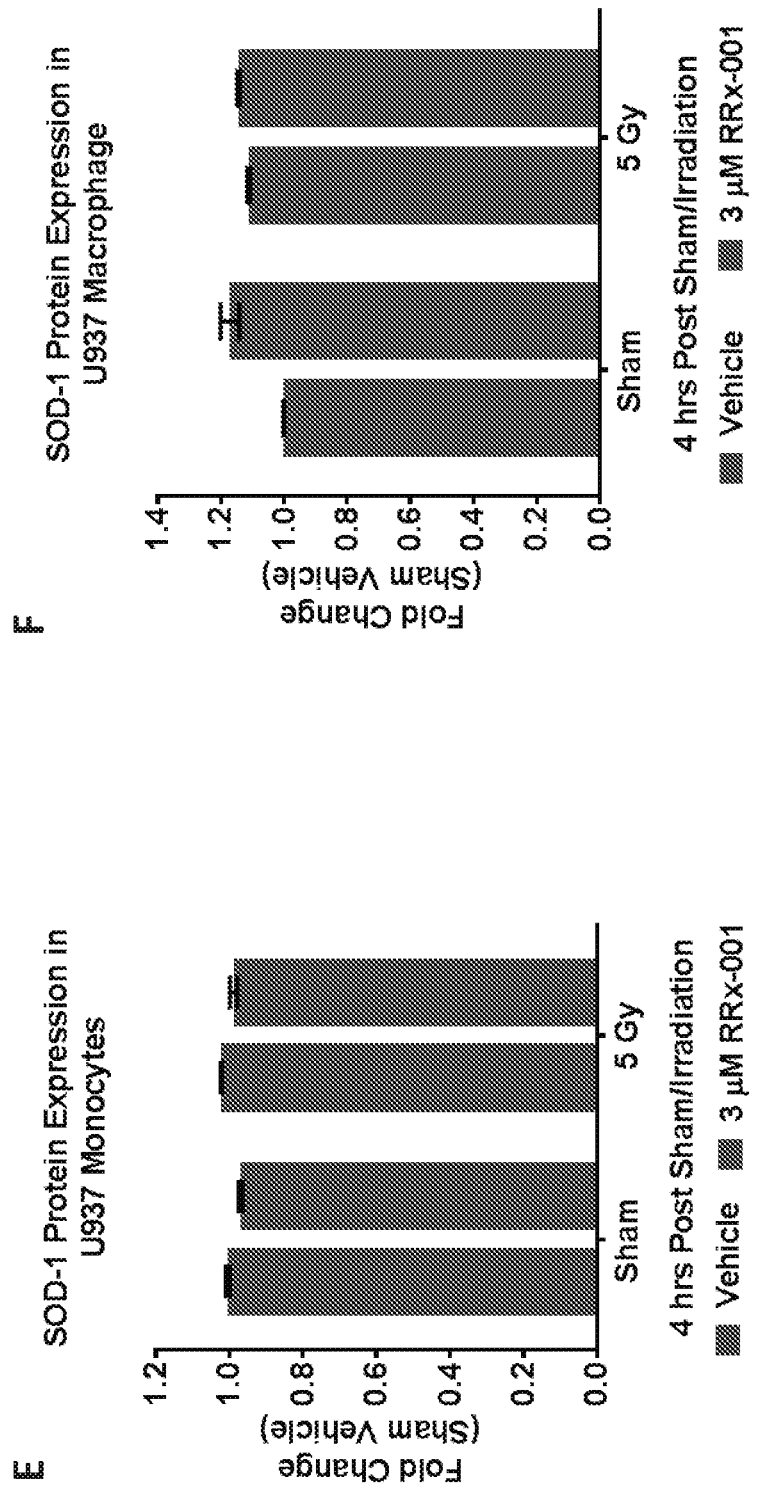
Figure 10:
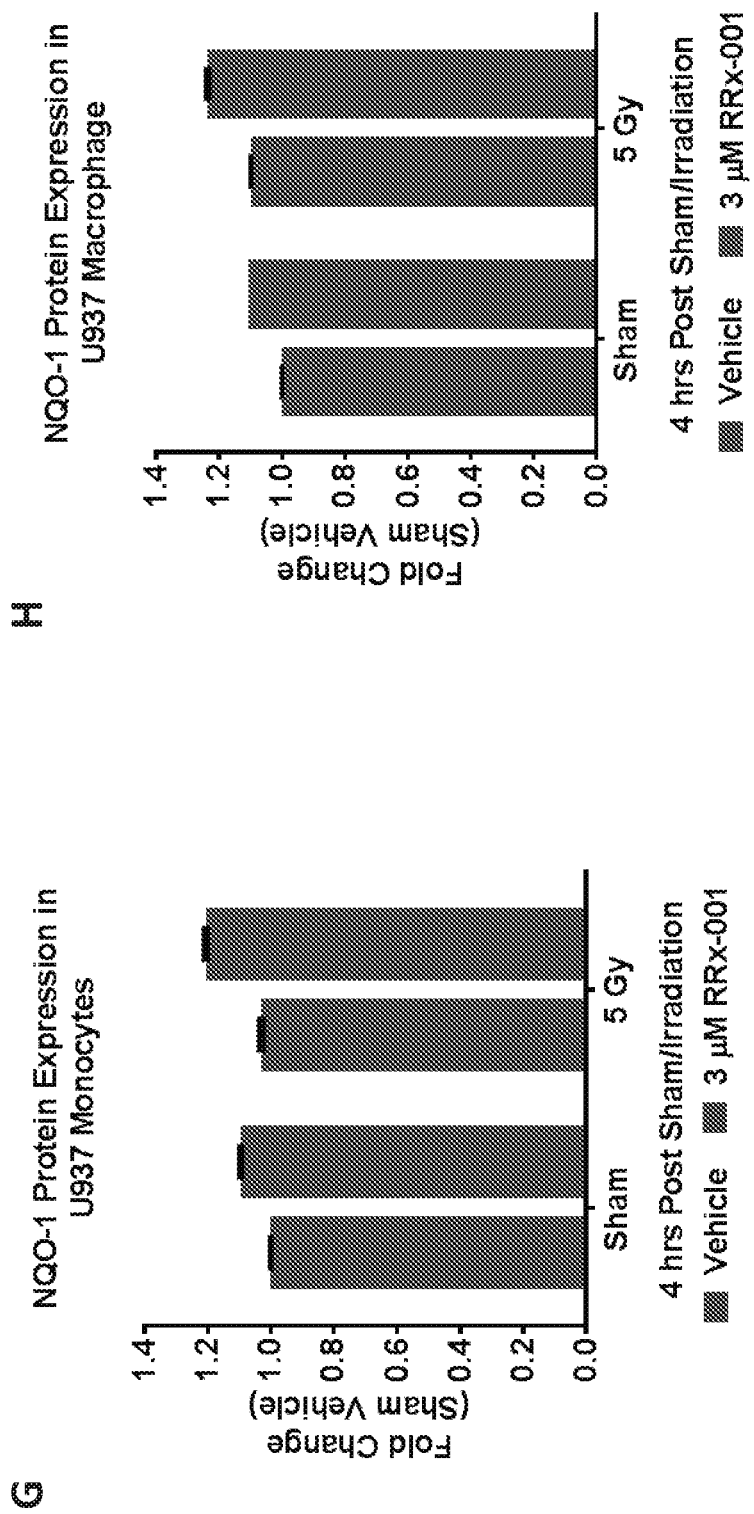
Figure 11:
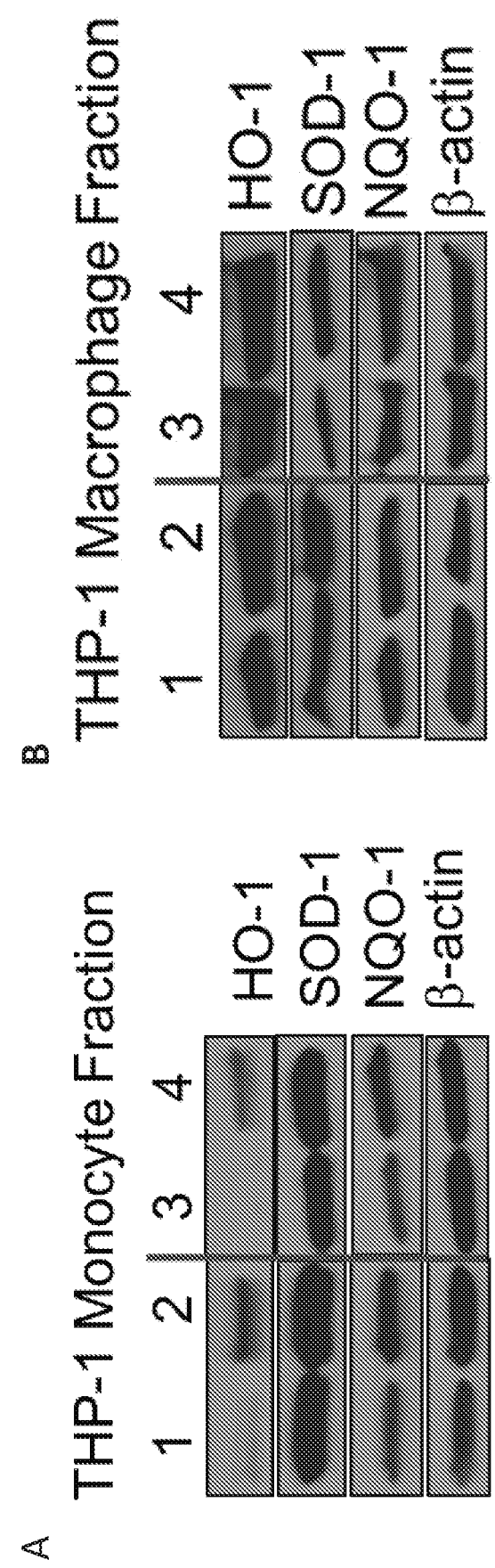
FIGS. 11A and 11B illustrate Western blots showing protein expression of HO-1, NQO-1, and SOD-1 in THP-1 monocyte fractions (FIG. 11A) and THP-1 macrophage fractions (FIG. 11B) 4 hours post-irradiation. Lane 1: vehicle/no irradiation; lane 2: vehicle/5 Gy irradiation; lane 3: RRx-001 (3 µM)/no irradiation; lane 4: RRx-001 (3 µM)/5 Gy irradiation.
FIGS. 11C-H illustrate quantification of protein expression for each gene (HO-1, NQO-1, and SOD-1) expressed as fold change relative to the vehicle/no irradiation control in THP-1 monocyte fractions and THP-1 macrophage fractions.
Figure 11:
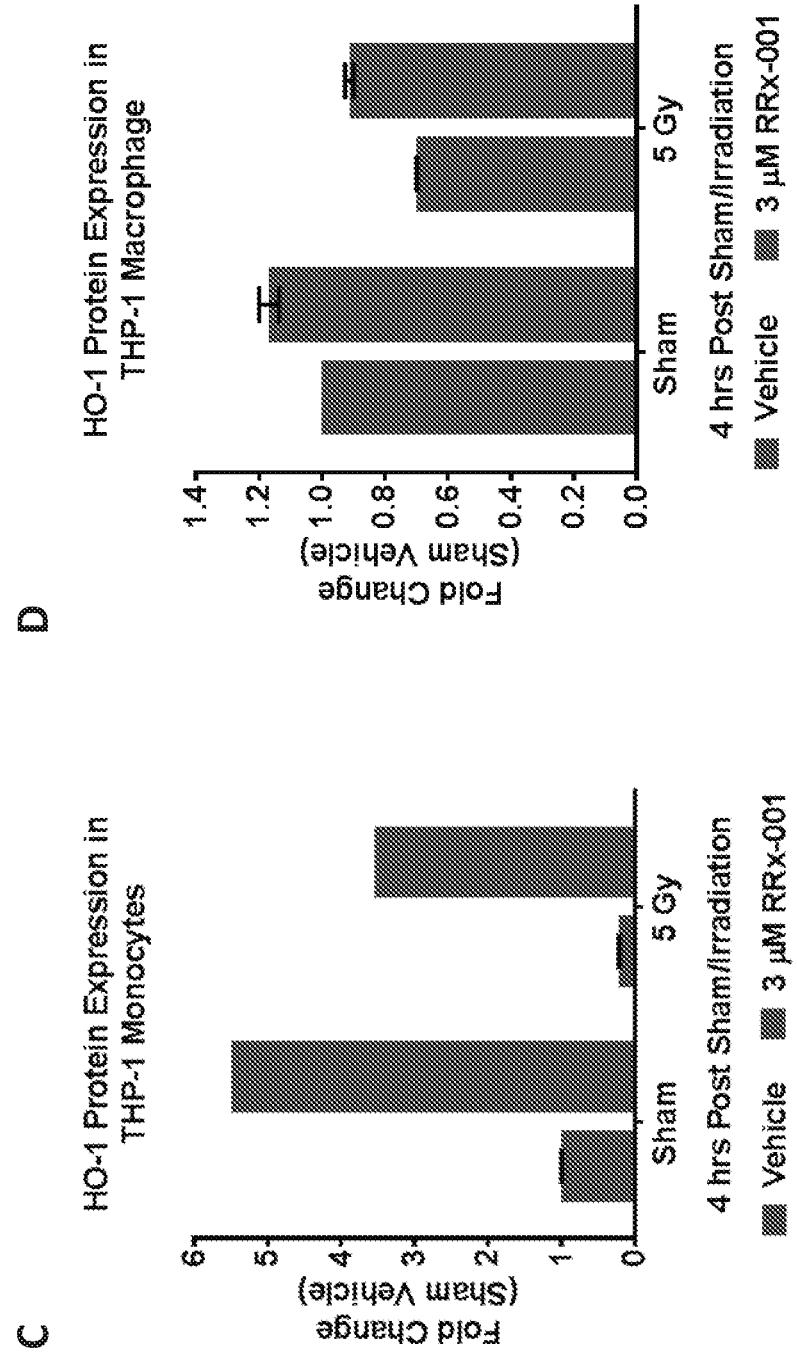
Figure 11:
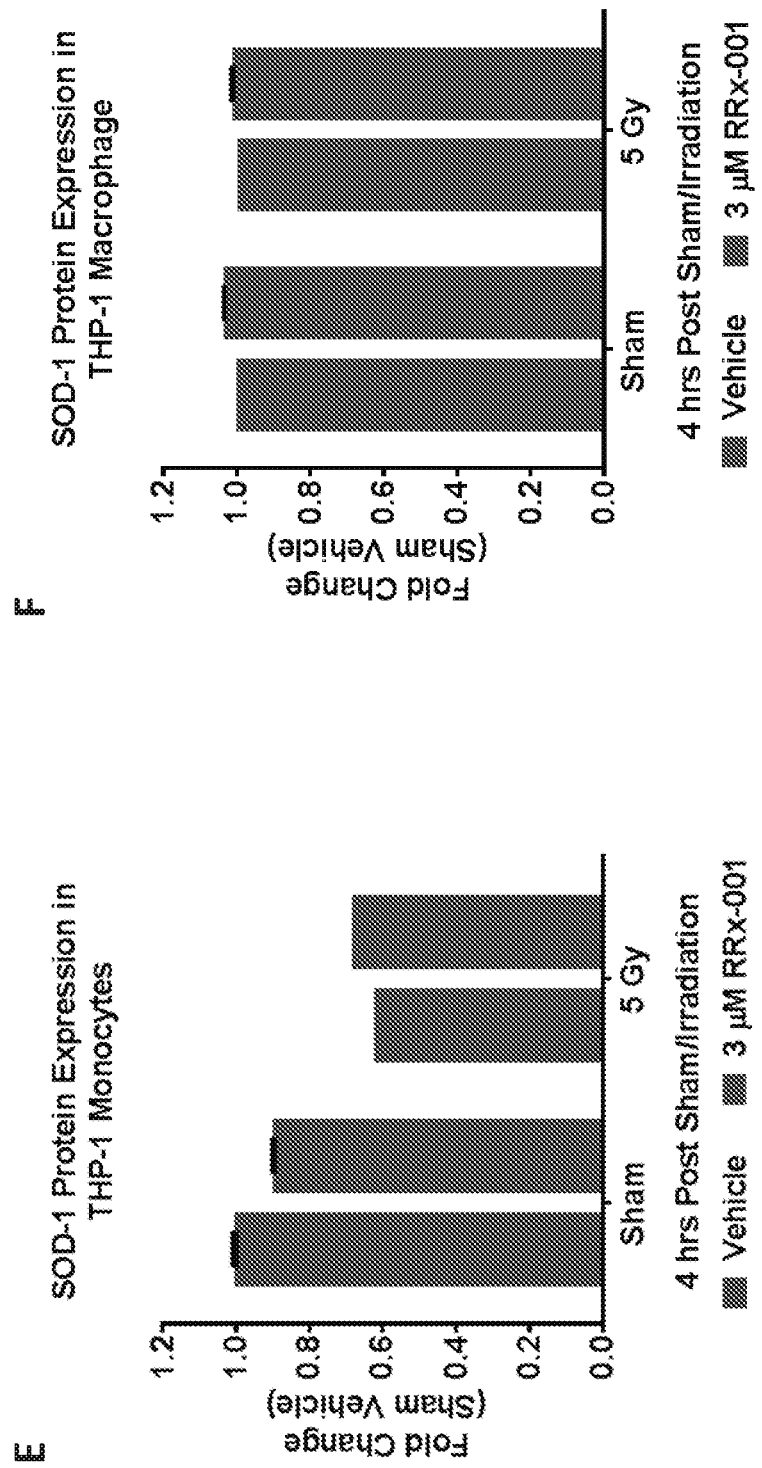
Figure 11:
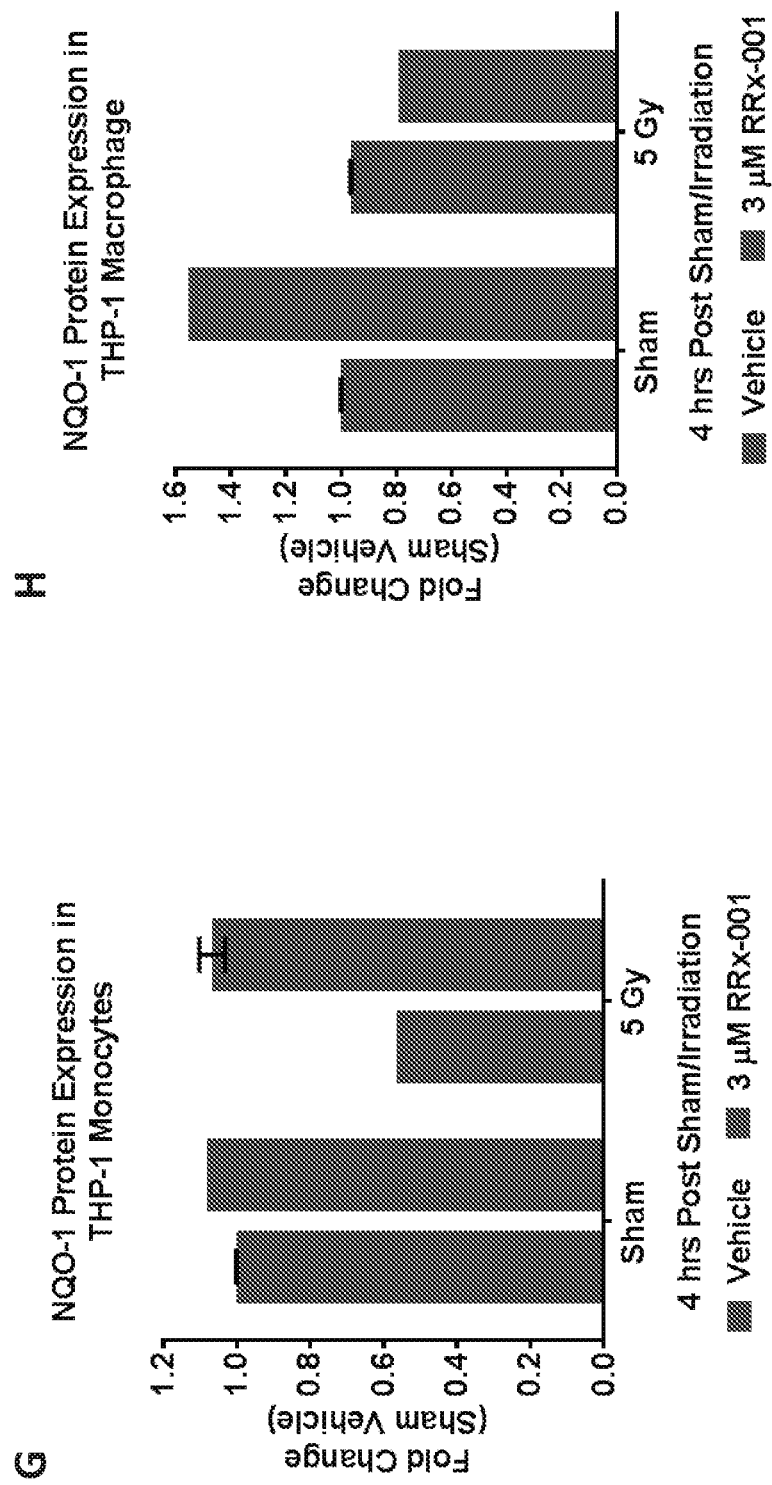

In the U937 macrophages, increased HO-1 production was observed after RRx-001 treatment in both the sham and irradiated groups; however no change in SOD-1 or NQO-1 was observed (FIG. 10). The results in the U937 monocytes were similar to those seen in the U937 macrophages. Overall, in both the U937 macrophage and monocyte fractions a significant increase in HO-1 was seen. A similar trend was also observed in the THP-1 monocytes; however, in the THP-1 macrophages no significant increase in HO-1 was seen (FIG. 11).

Figure 12:
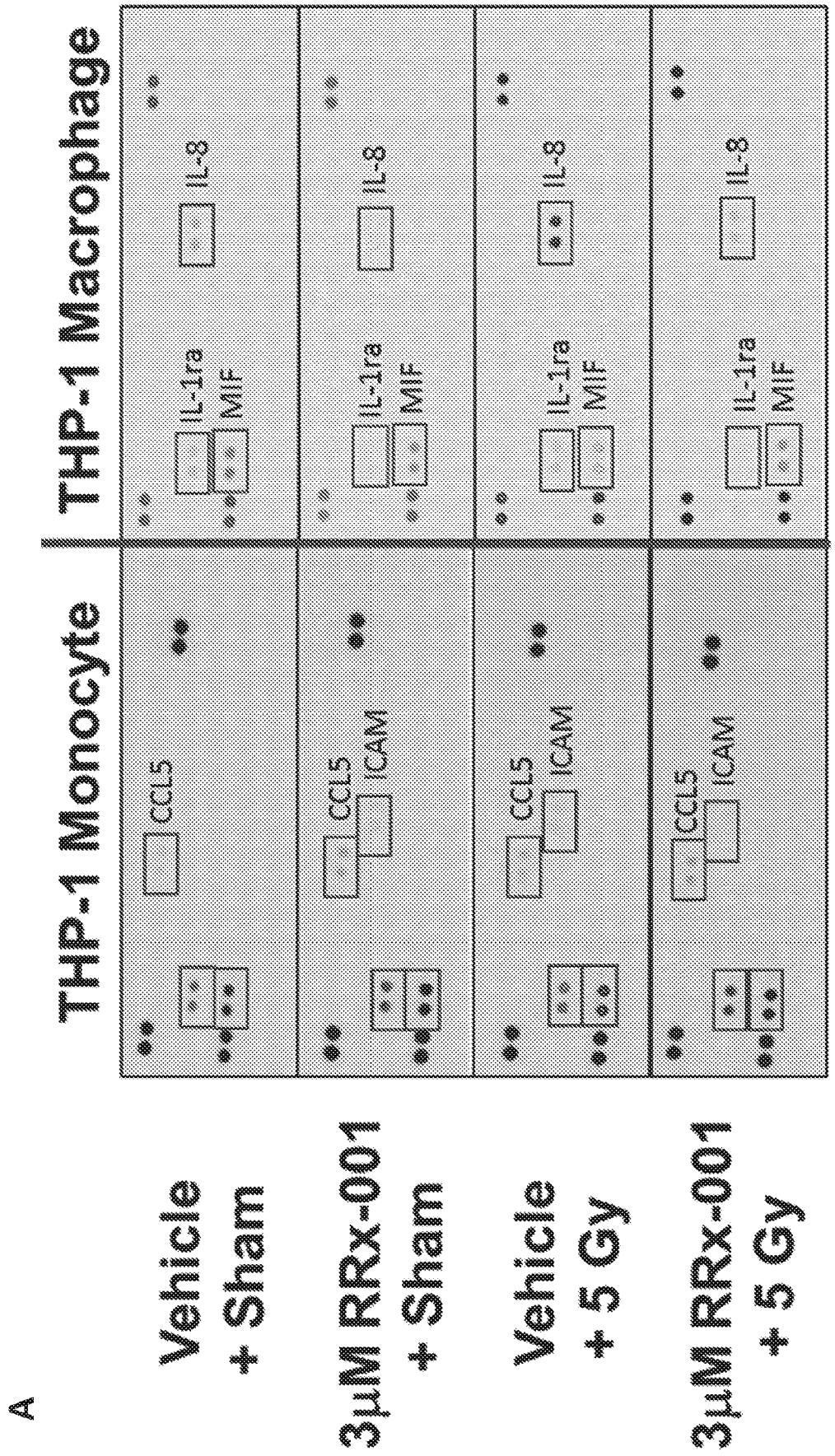
FIG. 12A illustrates dot blot expression of various cytokines and inflammatory modulators in irradiated THP-1 monocytes or THP-1 macrophages (5 Gy) treated with RRx-001 (3 µM) or vehicle control in THP-1 monocyte fractions and THP-1 macrophage fractions.
FIGS. 12B-E illustrate quantification of cytokine expression for selected genes expressed as fold change relative to the vehicle control in THP-1 monocyte fractions and THP-1 macrophage fractions.
Figure 12:
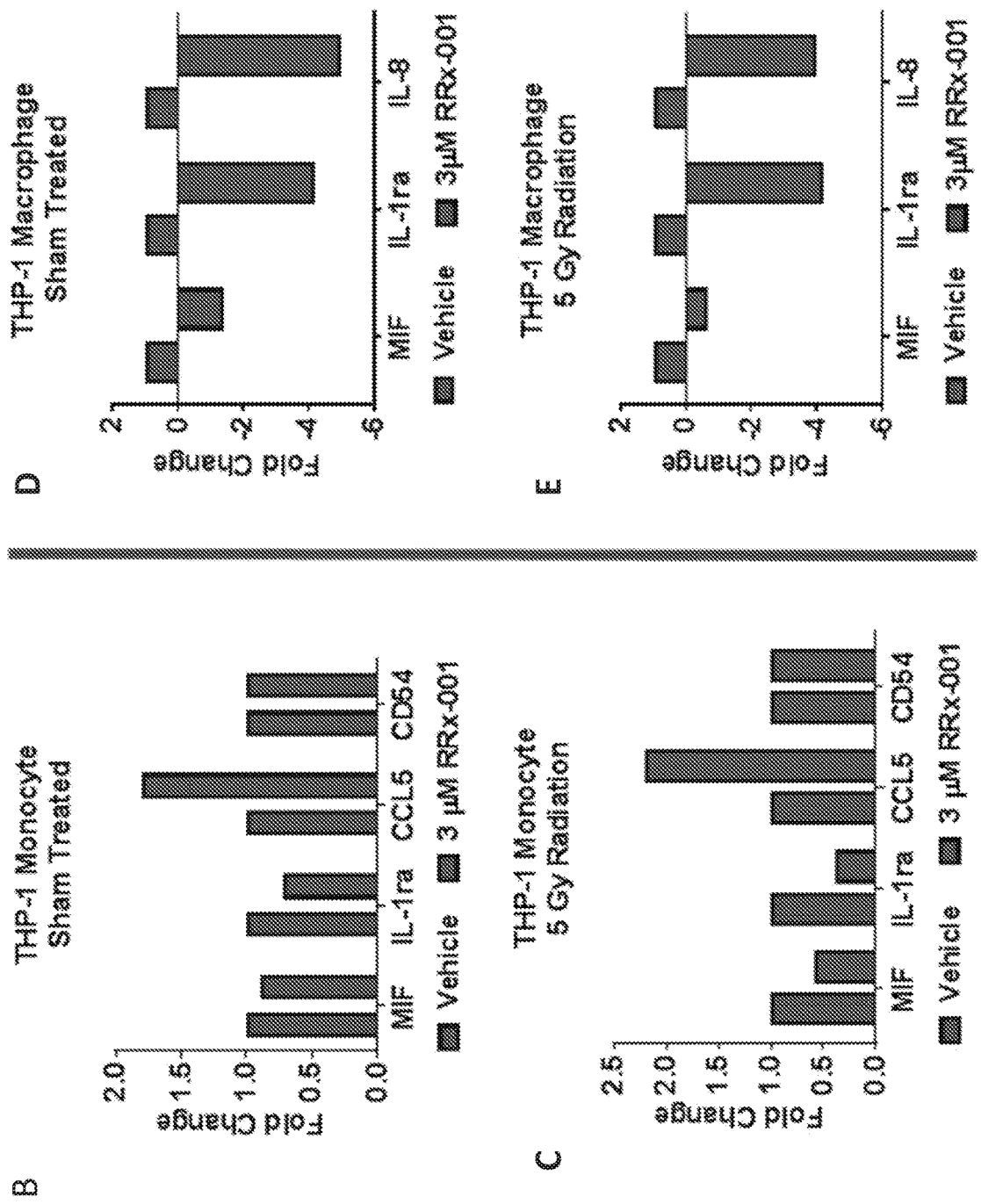

A cytokine array was employed to examine cytokine expression following in vitro irradiation of human monocytic leukemic THP-1 cells. THP-1 cells were differentiated into macrophages with 50 nM Phorbol 12-myristate 13-acetate (PMA) for 24 hours before treatment. Differentiated and non-differentiated cells were treated with 3 mM RRx-001 or 0.05% DMSO (vehicle control) for 16 hours prior to radiation. The cells were irradiated at 5 Gy or sham-irradiated and collected 4-8 hours later for both analysis. For the cytokine analysis, cell media was collected and blotted onto Proteome Profiler Human Cytokine Arrays (R&D Systems, Inc.) according to the manufacturer's protocol. The cytokine array showed a reduction in cytokines involved in inflammation in both the drug-treated sham and irradiated macrophage fraction as well as CCL5/RANTES induction in monocytes (FIG. 12).

The data suggest that RRx-001 may provide cellular protection from oxidative injury by increased HO-1 production in macrophage, monocytes, and mesenchymal stem cells. One potential mechanism is through the reduction in the pro-inflammatory chemokine IL-8 in macrophages and upregulation of CCL5/RANTES in monocytes, which may enhance immune cell reprogramming. Without wishing to be bound by theory, the significant increase of HO-1 may protect the cells from apoptosis and DNA damage and increase their survival compared to cells that were not preconditioned with RRx-001.

Example 4—Assessment of RRx-001 for the Treatment of Oral Mucositis

In this example, the ability of RRx-001 to treat oral mucositis induced by acute radiation was assess in hamsters.

Fifty-six (56) male Syrian Golden Hamsters were used in the study. Mucositis was induced by administering an acute radiation dose of 40 Gy directed to the left buccal cheek pouch on Day 0 at a rate of 2-2.5 Gy/min. Mucositis was evaluated clinically starting on Day 6 and continuing on alternate days until Day 28. Hamsters reaching a mucositis severity score of 4 or higher received buprenorphine (0.5 mg/kg) SC twice a day for 48 hours or until score dropped below 4.

Dosing was scheduled as follows: for animals in Groups 1-4, animals were dosed with RRx-001 (1, 3, or 10 mg/kg) or vehicle (1:2 DMA:PEG400 vol:vol ratio) once a day (QD) on Days −4, −1, 1, 4, 7, 11, 14, 18, 21, and 25 via intraperitoneal (IP) administration; animals in Groups 5-7 were dosed QD with RRx-001 (1, 3, or 10 mg/kg) on Days −4, −1, 1, 8, 15, and 22.

| Group # | # of Animals | Radiation (Day 0) | Treatment | Dose | Route | Dose Schedule* | Mucositis Evaluation (Q2D) |
|---|---|---|---|---|---|---|---|
| 1 | 8 males | 40 Gy | Vehicle DMA-PEG (1:2 vol/vol ratio) | — | IP | QD Days −4, −1, 1, 4, 7, 11, 14, 18, 21 & 25 | Day 6-28 |
| 2* | 8 males | 40 Gy | RRx-001 | 10 mg/kg | IP | | |
| 3 | 8 males | 40 Gy | RRx-001 | 3 mg/kg | IP | | |
| 4 | 8 males | 40 Gy | RRx-001 | 1 mg/kg | IP | | |
| 5* | 8 males | 40 Gy | RRx-001 | 10 mg/kg | IP | QD Days −4, −1, 1, 8, 15, 22 | |
| 6 | 8 males | 40 Gy | RRx-001 | 3 mg/kg | IP | | |
| 7 | 8 males | 40 Gy | RRx-001 | 1 mg/kg | IP | | |

Due to the presentation of adverse side effects following administration of the highest dose of RRx-001 (10 mg/kg, Groups 2 and 5), dosing with this compound was discontinued for the remainder of the study after Day 1; however, the animals continued to be monitored and scored for the duration of the study. Dosing of all other groups continued as scheduled. Upon study conclusion, on Day 28, Animals were euthanized via $CO_2$ inhalation and death was confirmed by monitoring heartbeat in accordance with USDA guidelines. Animals steadily gained weight throughout the duration of the study, except for animals in Groups 2 and 5, which were characterized by lower weights than all other groups. For Groups 2 and 5, weight slowly recovered after cessation of dosing, and by study termination, weights had rebounded back to be in line with other groups on the study.

Figure 13A:
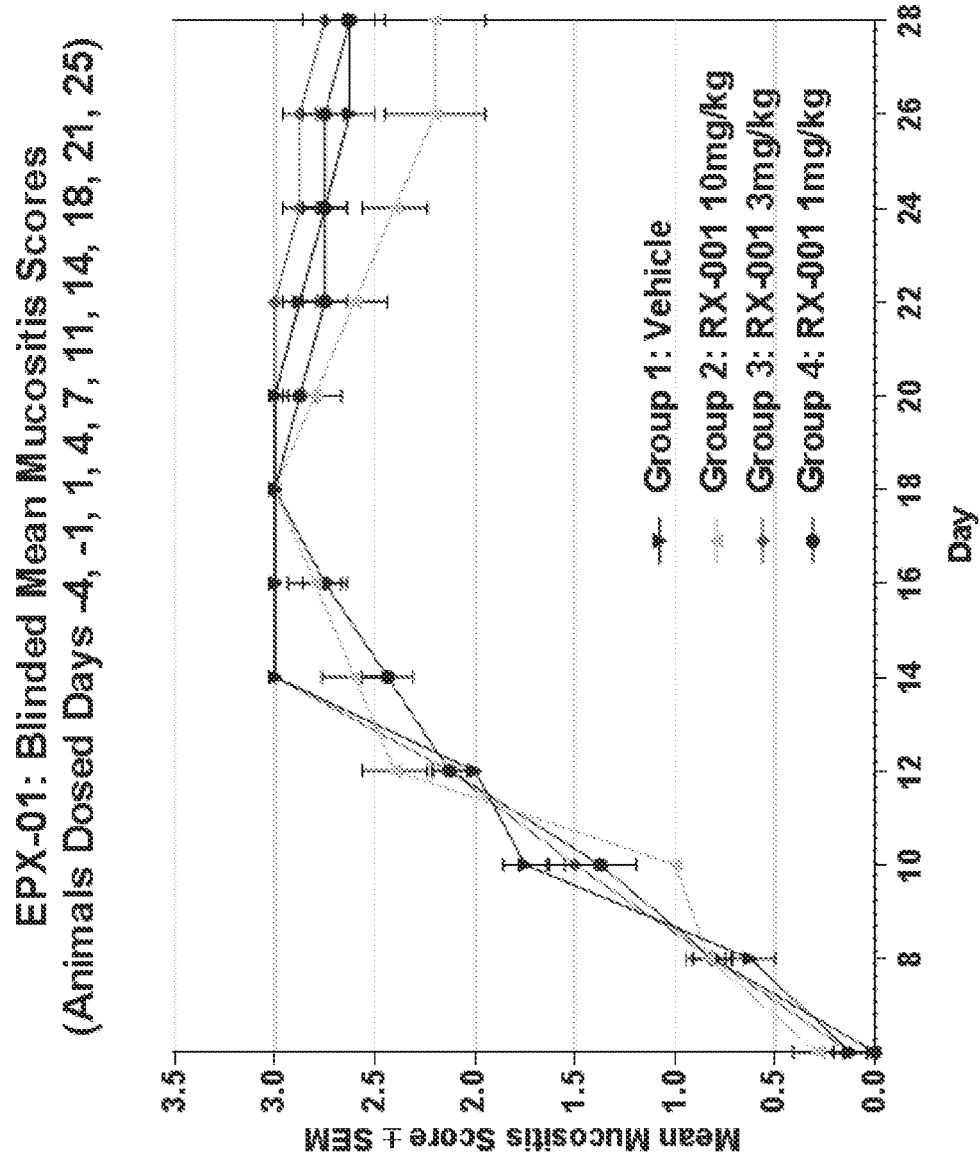
FIG. 13A provides mean daily mucositis scores for the twice per week dosing groups.
Figure 13B:
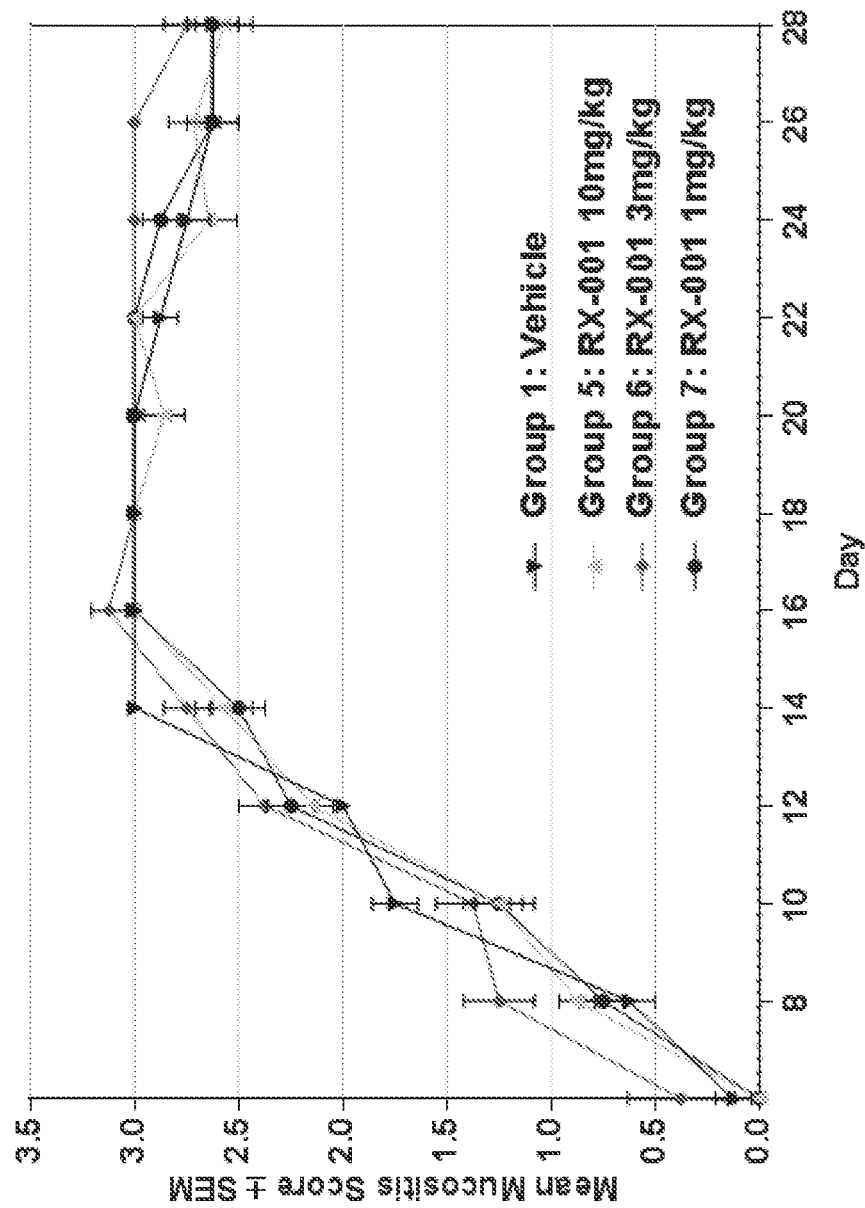
FIG. 13B provides mean daily mucositis scores for the once per week dosing groups. Mean group mucositis scores were calculated for each day of evaluation.

Mean daily mucositis scores are shown in FIG. 13. There was modest but significant enhancement of disease healing exhibited by animals treated with 10 mg/kg in Group 2, though dosing was terminated after Day 1. All other treatment groups had mucositis scores that tracked fairly close to each other, and with Vehicle dosed controls.

Figure 14A:
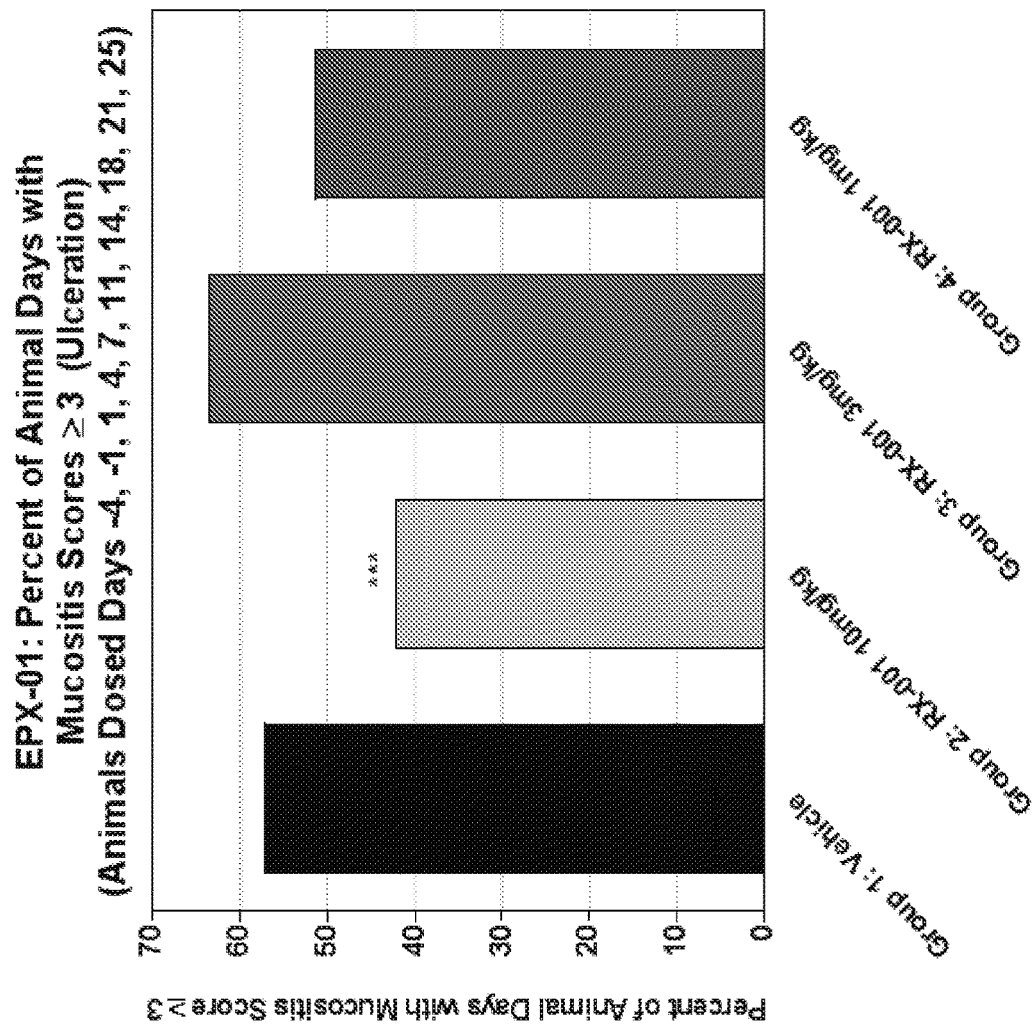
FIG. 14A provides data for percent of days with Mucositis scores≥3 for the entire study duration for the twice per week dosing groups.

The significance of differences observed between the control and treatment group was evaluated by comparing the days with mucositis scores≥3 and <3 between groups using chi-square analysis. Animals dosed with 10 mg/kg and 1 mg/kg RRx-001 displayed multiple days of significant improvement in mucositis scores compared to the Vehicle control group (FIG. 14). The percentage of animal days with a score of ≥3 in the Vehicle Group was 57.29%. The percentage of days with a score of ≥3 was statistically lower only for animals in Group 2 (dosed with 10 mg/kg on Days −4, −1, 1) in comparison to the Vehicle Group (p<0.01). There were numerous days where animals dosed with RRx-001 had percent ulceration days that were lower (which can be interpreted as ameliorative of disease severity) in comparison to vehicle-dosed animals. For the 3 and 1 mg/kg concentrations, twice weekly dosing appeared to provide more beneficial effects on percent days of ulceration than dosing one time per week (Groups 4 vs. Group 7). Interestingly, animals dosed with the 10 mg/kg concentrations in both Groups 2 and 5, which were only dosed on Days −4, −1, and 1, had the best response in decreasing percent ulceration.

An analysis of the severity of mucositis was performed using the Mann-Whitney rank sum analysis to compare the visual mucositis scores for the treatment group to the Vehicle control group on each day of evaluation. The results of this analysis are shown in Table 5 and 6. In this analysis, 2 days of significant reduction in the mucositis score are generally required before it is regarded as meaningful. Animals dosed with 10 mg/kg and 1 mg/kg RX-001 displayed multiple days of significant improvement in mucositis scores compared to the Vehicle control group. A similar effect was observed for animals dosed 1× week, as shown in FIG. 15.

The percentage of animals in each group with ulcerative mucositis at each day of evaluation is shown in FIG. 16. This evaluation was intended to clarify which days of treatment had its maximal impact on the course of ulcerative mucositis. There were numerous days where animals dosed with RRx-001 had percent ulceration days that were lower (which can be interpreted as ameliorative of disease severity) in comparison to vehicle-dosed animals. For 1 mg/kg concentrations, twice weekly dosing appeared to provide more beneficial effects on percent days of ulceration than dosing one time per week (Groups 4 vs. Group 7). Interestingly, animals dosed with the 10 mg/kg concentrations in both Groups 2 and 5, which were only dosed on Days −4, −1, and 1, had the best response in decreasing percent ulceration.

Example 5—Characterization of a Radiotherapeutic Combination of RRx-001 and Second Radioprotective Agent on Survival After Exposure to Lethal Radiation To determine the effects of systemic administration of a radiotherapeutic combination of RRx-001 and a second radioprotective agent on survival in response to a lethal dose of radiation was assayed in mice. CD2F1 male mice 9.5-11 weeks old are administered a single dose of RRx-001 alone or in combination with amifostine and optionally a cytokine, such as GM-CSF, by intraperitoneal (IP) injection 24 hours prior to a lethal radiation dose. Control mice are injected with vehicle. The mice are subjected to total body irradiation (TBI) with 9.35 Gy (LD70/30) at 0.6 Gy/min using High-level Cobalt-60.

It is expected that mice receiving the combination of RRx-001 and amifostine and/or GM-CSF exhibit increased survival compared to mice treated with vehicle or RRx-001 alone.

Example 6—Characterization of a Radiotherapeutic Combination of RRx-001 and Amifostine on Hematopoietic Protection from Radiation To determine the pathophysiological effects of a radiotherapeutic combination of RRx-001 and a second radioprotective agent on hematopoietic protection in mice, CD2F1 male mice are treated with 10 mg/kg RRx-001 alone or in combination with amifostine and optionally a cytokine, such as GM-CSF, or a vehicle control 24 hours prior to a sublethal dose of TBI (7 Gy at 0.6 Gy/min using High-level Cobalt-60) or sham irradiation (day 0).

It is expected that mice receiving the combination of RRx-001 and amifostine and/or GM-CSF exhibit increased bone marrow cellularity and white and red blood cell production compared to mice treated with vehicle or RRx-001 alone.

The entire disclosure of each of the patent documents and scientific articles referred to herein is incorporated by reference for all purposes.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting

What is claimed is:

1. A method for treating a subject in need of protection against radiation, comprising administering to the subject in need thereof (i) an effective amount of a first therapeutic agent selected from the group consisting of RRx-001 and a pharmaceutically acceptable salt thereof and (ii) an effective amount of a second therapeutic agent that reduces the effect of radiation on a subject, to thereby protect the subject against radiation.

2. The method of claim 1, wherein the administering achieves protection against radiation for a duration at least 6 hours, at least 12 hours, at least 36 hours, at least 48 hours, at least 3 days, at least 4 days, at least 5 days, at least 6 days, at least 1 week, at least 2 weeks, at least 3 weeks, at least 4 weeks or longer.

3. A method of reducing radiation-exposure damage to a subject, comprising administering to the subject in need thereof (i) an effective amount of a first therapeutic agent selected from the group consisting of RRx-001 and a pharmaceutically acceptable salt thereof and (ii) an effective amount of a second therapeutic agent that reduces the effect of radiation on a subject, to thereby reduce radiation-exposure damage to the subject.

4. The method of claim 1, wherein at least one dose of the first therapeutic agent and at least one dose of the second therapeutic agent are administered to the subject prior to or after exposure to the radiation.

5. The method of claim 1, wherein the first therapeutic agent is administered at a dosage that provides RRx-001 in an amount ranging from about 0.01 mg to about 500 mg, about 0.1 mg to about 200 mg, or about 0.5 mg to about 150 mg of RRx-001 on each day the therapeutic agent is administered to the subject.

6. The method of claim 1, wherein the first therapeutic agent and/or second therapeutic agent is administered by a route selected from the group consisting of parenteral administration, oral administration and topical administration, and wherein the first therapeutic agent and/or second therapeutic agent is administered systemically or locally.

7. The method of claim 1, wherein the first therapeutic agent and/or second therapeutic agent is administered subcutaneously to the subject via a pump device implanted in the subject that contains the therapeutic agent.

8. The method of claim 1, wherein the second therapeutic agent comprises amifostine or a pharmaceutically acceptable salt thereof, a cytokine, glutathione, N-acetyl-cysteine, iron, an iron salt, ferric oxide, a cobalt salt, a metal chelator agent, a fullerene, an agent that promotes DNA repair, a viral gene therapy that delivers Poly ADP ribose polymerase (PARP), an agent that inhibits p53 activity, an anti-TNF alpha agent, cobalt chloride, an agent that chelates iron, deferoxamine, an agent that chelates copper, an agent that chelates zinc, a polyamide, resveratrol, sodium orthovanadate, pifithrin-alpha, infliximab, etanercept, thalidomide, or pentoxifylline.

9. The method of claim 1, wherein the second therapeutic agent comprises amifostine and is administered at a dosage of from about 100 mg/m$^2$ to about 500 mg/m$^2$ or about 150 mg/m$^2$ to about 250 mg/m$^2$ amifostine on any day on which amifostine is administered to the subject.

10. The method of claim 8, wherein the cytokine is interleukin 1, interleukin 2, interferon gamma, granulocyte/macrophage colony-stimulating factor, granulocyte-colony-stimulating factor, or tumor necrosis factor alpha.

11. The method of claim 1, wherein the method further comprises, prior to administration of the therapeutic agent, administering to the subject a pain-relieving agent.

12. The method of claim 11, wherein the pain-relieving agent is aspirin, a corticosteroid, or a non-steroidal anti-inflammatory agent.

13. The method of claim 1, further comprising, prior to administration of the therapeutic agent, administering to the subject a local analgesic agent to tissue in proximity to the site of administration of the first therapeutic agent.

14. The method of claim 13, wherein the local analgesic agent is a caine analgesic, lidocaine, hydrochloride, VanPen cream, a NSAID, or acetaminophen.

15. The method of claim 1, wherein the subject is an adult human, pediatric human, animal, subject at risk of exposure to radiation from a nuclear emergency, subject receiving radiation therapy, or subject suffering from or at risk of suffering from mucositis.

16. The method of claim 1, further comprising administering a EGFR inhibitor or inorganic nitrile salt to the subject.

17. The method of claim 16, wherein the inorganic nitrite salt is an alkali metal nitrite or sodium nitrite.

18. A method of protecting biological material from the damaging effects of radiation, comprising exposing said biological material to i) an effective amount of a first therapeutic agent selected from the group consisting of RRx-001 and a pharmaceutically acceptable salt thereof and (ii) an effective amount of a second therapeutic agent that reduces the effect of radiation on a subject, to thereby protect the biological material from the damaging effects of radiation, wherein the first therapeutic agent is administered prior to or after exposure to the radiation.

19. The method of claim 1, wherein the radiation comprises α-rays, β-rays, x-rays, γ-rays, neutron radiation, ionizing radiation, ionizing radiation from sunlight, ionizing radiation from radioactive nuclei, ionizing radiation from an explosive device, or a combination thereof.

20. The method of claim 1, wherein the first therapeutic agent is RRx-001.

* * * * *